(12) United States Patent
Pero et al.

(10) Patent No.: US 9,388,179 B2
(45) Date of Patent: Jul. 12, 2016

(54) N-SUBSTITUTED INDAZOLE SULFONAMIDE COMPOUNDS WITH SELECTIVE ACTIVITY IN VOLTAGE-GATED SODIUM CHANNELS

(71) Applicant: Merck Sharp & Dohme Corp., Rahway, NJ (US)

(72) Inventors: Joseph E. Pero, Harleysville, PA (US); Hannah D. G. F. Lehman, Boyertown, PA (US); Mark E. Layton, Harleysville, PA (US); Michael A. Rossi, Middletown, DE (US); Michael J. Kelly, III, Paoli, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/437,142

(22) PCT Filed: Oct. 23, 2013

(86) PCT No.: PCT/US2013/066360
§ 371 (c)(1),
(2) Date: Apr. 20, 2015

(87) PCT Pub. No.: WO2014/066491
PCT Pub. Date: May 1, 2014

(65) Prior Publication Data
US 2015/0284389 A1 Oct. 8, 2015

Related U.S. Application Data

(60) Provisional application No. 61/719,118, filed on Oct. 26, 2012.

(51) Int. Cl.
| | |
|---|---|
| *C07D 401/12* | (2006.01) |
| *C07D 417/12* | (2006.01) |
| *A61K 31/416* | (2006.01) |
| *C07D 471/08* | (2006.01) |
| *C07D 401/14* | (2006.01) |
| *C07D 231/56* | (2006.01) |
| *C07D 417/14* | (2006.01) |

(52) U.S. Cl.
CPC ............ *C07D 471/08* (2013.01); *C07D 231/56* (2013.01); *C07D 401/12* (2013.01); *C07D 401/14* (2013.01); *C07D 417/12* (2013.01); *C07D 417/14* (2013.01)

(58) Field of Classification Search
None
See application file for complete search history.

(56) References Cited

U.S. PATENT DOCUMENTS

| | | | |
|---|---|---|---|
| 2008/0004288 A1 * | 1/2008 | Santhakumar | C07D 231/56 514/254.06 |
| 2009/0023740 A1 | 1/2009 | Fulp et al. | |
| 2011/0201607 A1 | 8/2011 | Kuduk et al. | |
| 2012/0010182 A1 | 1/2012 | Brown et al. | |

FOREIGN PATENT DOCUMENTS

WO WO2012095781 7/2012

* cited by examiner

*Primary Examiner* — Zinna Northington Davis
(74) *Attorney, Agent, or Firm* — John C. Todaro; H. Eric Fischer

(57) ABSTRACT

Disclosed are compounds of Formula $A^A$ and Formula $A^B$: wherein "Heteroaryl-1", $R^{A1}$, $R^{A2}$, $R^{B1}$, and $R^C$ are defined herein, which novel compounds have properties for blocking $Na_v$ 1.7 ion channels found in peripheral and sympathetic neurons. Also described are pharmaceutical formulations comprising the compounds of Formulae $A^A$ and $A^B$ or their salts, and methods of treating neuropathic pain disorders using the same.

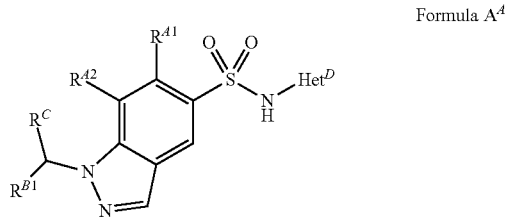

Formula $A^A$

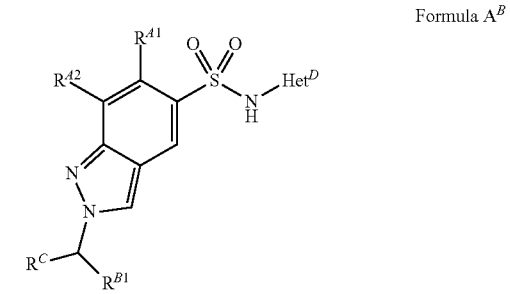

Formula $A^B$

20 Claims, No Drawings

N-SUBSTITUTED INDAZOLE SULFONAMIDE COMPOUNDS WITH SELECTIVE ACTIVITY IN VOLTAGE-GATED SODIUM CHANNELS

CONTINUING DATA

This application is a 371 of PCT/US2013/066360 filed Oct. 23, 2013 which claims benefit of 61/719,118 filed Oct. 26, 2012.

BACKGROUND

Voltage-gated sodium channels play a central role in initiating and propagating action potentials in electrically excitable cells, see for example Yu and Catterall, Genome Biology 4:207 (2003) and references therein. Voltage-gated sodium channels are multimeric complexes characterized by an Alpha-subunit which encompasses an ion-conducting aqueous pore, the site of the essential features of the channel, and at least one Beta-subunit that modifies the kinetics and voltage-dependence of the channel gating. These structures are ubiquitous in the central and peripheral nervous system and are believed to play a central role in initiation and propagation of electrical signals in the nervous system.

It has been shown in human patients as well as in animal models of neuropathic pain that damage to primary afferent sensory neurons may lead to neuroma formation and spontaneous activity, as well as evoked activity in response to normally innocuous stimuli. [Carter, G. T. and Galer, B. S., Advances in the Management of Neuropathic Pain, Physical Medicine and Rehabilitation Clinics of North America, 2001, 12(2): pp 447 to 459]. Injuries of the peripheral nervous system often result in neuropathic pain persisting long after an initial injury resolves. Examples of neuropathic pain include, for example, post herpetic neuralgia, trigeminal neuralgia, diabetic neuropathy, chronic lower back pain, phantom limb pain, pain resulting from cancer and chemotherapy, chronic pelvic pain, complex regional pain syndrome and related neuralgias. The ectopic activity of normally silent sensory neurons is thought to contribute to the generation and maintenance of neuropathic pain, which is generally assumed to be associated with an increase in sodium channel activity in the injured nerve. [Baker, M. D. and Wood, J. N., Involvement of Na Channels in Pain Pathways, TRENDS is Pharmacological Sciences, 2001, 22(1): pp 27 to 31.

Nine different Alpha-subunits have been identified and characterized in mammalian voltage-gated sodium channels. These structures are designated $Na_v$ 1.X sodium channels (X=1 to 9) in accordance with currently accepted nomenclature practice, designating their ion selectivity (Na), the physiological regulator ('v', potential, i.e. voltage), and the gene subfamily encoding them (1.X), with the number designator X (1 to 9) being assigned for the alpha subunit present in the structure (see Aoldin et al., Neuron, 28:365-368 (2000)). $Na_v$1.7 voltage-gated sodium ion channels (herein designated "Nav 1.7 channels" in some instances for convenience) are expressed primarily in sensory and sympathetic neurons. They are believed to play a role in nociception and in particular have a central role in inflammatory pain perception, (see Wood et al. J. Neurobiol. 61: pp 55-71 (2004) and Nassar et al., Proc. Nat. Acad. Sci. 101(34): pp 12706-12711 (2004)). Accordingly it is believed that identification and administration of agents which interact to block $Na_v$ 1.7 voltage-gated sodium ion channels represents a rational approach for providing treatment or therapy for nociception disorders stemming from dysfunction of $Na_v$1.7 voltage-gated sodium ion channels (see Clare et al., Drug Discovery Today, 5: pp 506-520 (2000)).

Because voltage gated sodium ion channels are ubiquitous in the central and peripheral nervous system and conservation of structures in the various Alpha-subunits characterizing voltage-gated sodium ion channels implicates the potential for producing serious side effects when utilizing therapeutic agents that target blocking voltage-gated sodium ion channels, therapeutic agents suitable for use in addressing nociception disorders require specificity in their action, for example, low activity blocking $Na_v$1.5 sodium ion channels (which channels are thought to be important in regulation of cardiac function) while displaying potent activity in blocking $Na_v$1.7 sodium ion channels (which is believed to be central in providing therapy for inflammatory nociception and disorders arising from dysfunctional $Na_v$ 1.7 sodium ion channels). It will be appreciated that in general activity selectively targeting $Na_v$ 1.7 sodium ion channels while not significantly effecting other $Na_v$1.X channels would be advantageous in developing therapeutics for such disorders.

Published international application No. WO09012242 (the '242 publication) describes compounds having the structure of Formula PA:

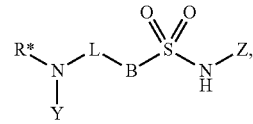

Formula PA wherein R* is a proton, alkyl or heteroalkyl, aryl, or heteroaryl group, Y is an aryl group or a 5 or 6 member-ring heteroaryl group, L is either not present or is a cyclic structure containing nitrogen or substituted with nitrogen, B is a cycloalkyl, heterocycloalkyl, aryl or heteroaryl moiety, and Z is a five or six-member ring heteroaryl moiety, and optionally R*, N, and Y form a cyclic structure which may be a heteroaryl moiety, for example, the compound of Formula PB:

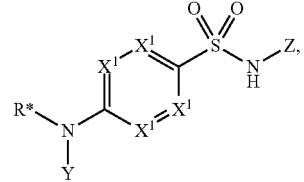

Formula PB wherein R*, Y, and Z are as defined for the compound of Formula PA, and wherein each $X^1$ is independently N or unsaturated carbon optionally substituted with hydrogen, halogen, CN, OH, alkyl or substituted alkyl. These compounds are said to have activity as Nav 1.7 channel and Nav 1.3 channel blockers but are not shown to have selectivity as specific Nav 1.7 channel blockers.

The '242 publication describes also compounds of Formula PB[A]:

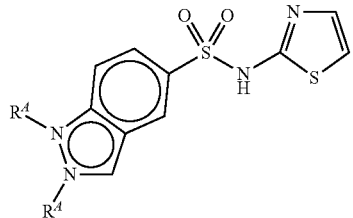

Formula PB[A]

wherein one of R[A] is a substituent appended to the nitrogen atom to which it is bonded and the other of R[A] indicates that the nitrogen atom to which it is attached is double-bonded to the carbon atom adjacent to it, and wherein, when it represents a substituent, R[A] is a benz-alkyl- or an acetophenone-alkyl-substituent which is optionally substituted by one or more alkoxy moieties. Although the '242 publication reports Nav 1.7 activity for some of the compounds described therein, selectivity relative to the Nav 1.5 receptor is not reported nor ascertainable from the '242 publication.

Compounds having $Na_v1.7$ activity described in published international applications WO 2010079443 (the '443 publication) and related WO2012004706, WO2012004714, WO2012064984, WO2013064983, and WO2013064984 have the structure of Formula PC:

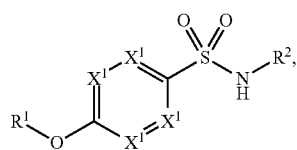

Formula PC wherein $X^1$ is N or C—$R^3$ ($R^3$ is a wide number of substituents including halogen), $R^1$ is a cycloalkyl, aryl or heteroaryl moiety and $R^2$ is a heteroaryl moiety.

Examples of these compounds include compounds of Formula PD:

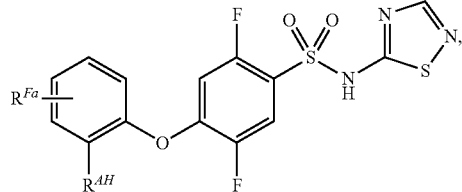

Formula PD where R[AH] is an aryl or heteroaryl moiety and R[Fa] is one or more of a wide variety of substituents, for example the hetero-substituted aryl compounds of Formula PE and Formula PF:

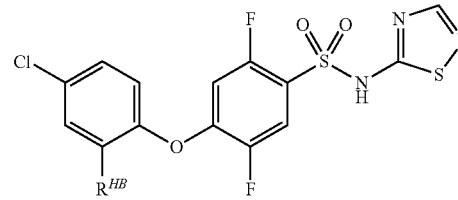

Formula PE

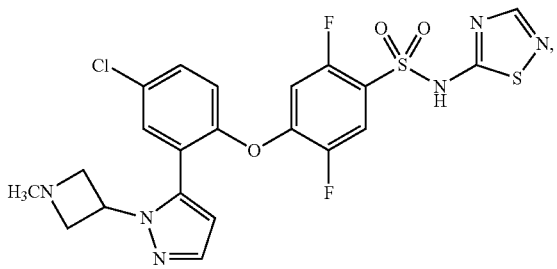

Formula PF wherein R[HB] is a heterobicyclo moiety.

An additional example of these compounds are the heterocycloalkyl-substituted compounds of Formula PG:

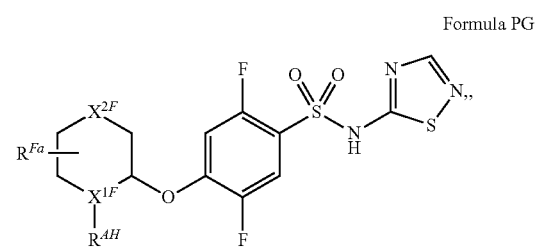

Formula PG wherein at least one of $X^{1F}$ and $X^{2F}$ are a heteroatom and the other is either a substituted carbon or CH, R[AH] is an aryl or heteroaryl moiety and R[Fa] is one or more of a wide variety of substituents. These foregoing compounds are said to have affinity for Nav 1.7 sodium channels and modest or low affinity for $Na_v1.5$ sodium channels, but do not offer much structural diversity.

Acylsulfonamide compounds have also recently been reported in, for example, published international application nos. WO2012004743, WO2012007868; WO2012007869, and WO2012007877 and US patent application publication no. US20120010207, which have the structure of Formula PH:

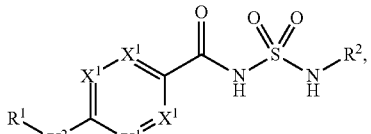

Formula PH wherein $X^1$ is N or C—$R^3$ ($R^3$ is a wide number of substituents including halogen, alkoxy, and cyano, but not alkyl), X2 is —O—, —OCH$_2$—, —CH$_2$O—, —CH$_2$—, or —S—, R1 is aryl or heteroaryl moiety and $R^2$ is an alkyl, cycloalkyl, alkaryl, alkheteroaryl, aryl or heteroaryl moiety, which compounds are reported to have activity for Nav 1.7 sodium channels.

Compounds of Formula PI are described in a series of patents assigned to American Cyanamide Co (e.g. U.S. Pat. Nos. 3,705,185; 4,243,609; 4,227,014; 4,245,097; 4,230,878; 4,205,085; 4,211,783; 4,230,628; 4,485,105; 4,136,256; 4,242,273; 4,254,138; 4,272,546; 4,309,553; 4,305,959; 4,310,545; 4,318,914; and 4,670,421):

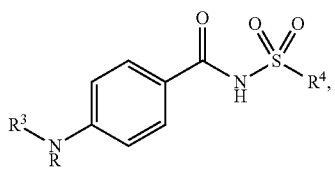

Formula PI wherein $R^3$ is, among other silylated moieties, silylated alkyl; R is H or a group which will be metabolized into H when placed in vivo; and $R^4$ is an aromatic moiety. These compounds are said to be useful and antiatherosclerotic agents, however they are not known to be Nav 1.7 active compounds.

Compounds of Formula PJ are described in U.S. Pat. No. 4,602,016 to Cross et al.:

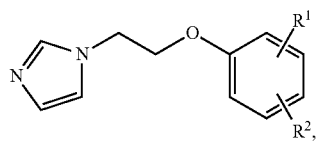

Formula PJ wherein $R^1$ can be, among other substituents, —C(O)—NH—S(O$_2$)-alkyl, and $R^2$ can be H, $C_{1-4}$-alkyl, halogen, or $C_{1-4}$-alkoxy. These compounds are reported to inhibit thromboxane synthetase enzyme but are not known to have Nav 1.7 activity.

Compounds of Formula PK are described in U.S. Pat. No. 6,414,001 to Akira et al.:

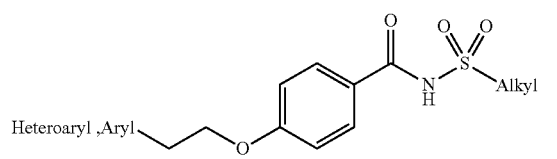

Formula PK wherein "alkyl" is a $C_{1-4}$-alkyl group, "Aryl" is an aryl group and "Heteroaryl" is a heteroaromatic moiety of 5 carbon atoms or more. These compounds are reported to have activity in enhancing insulin utilization in diabetics but are not known to have Nav 1.7 activity.

Recently, compounds described in published international applications WO 2013/025883 WO2013/086229, and WO2013/134518, having the structure of Formula PH:

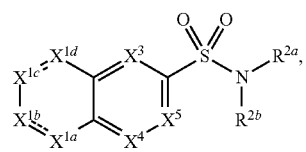

Formula PH wherein one of $R^{2a}$ or $R^{2b}$ is an aryl or heteroaryl moiety and the other is —H or alkyl, $X^3$ to $X^5$ are =N— or =CR$^5$— (where $R^5$ is a wide range of compatible substituents), $X^{1a-1d}$ are =N—, —NR$^4$— (where $R^4$ is H, alkyl, or a wide variety of other substituents compatible with N), or =CR$^3$— ($R^3$ is a wide number of substituents, including, H, alkyl, aryl and heteroaryl) and wherein $X^{1c}$ may be absent, in which case $X^{1b}$ is CH. These compounds claim activity for Nav1.7 sodium ion channels and selectivity over Nav1.5 channels.

There remains a need for additional compounds having high potency and selectivity for Na$_v$ 1.7 sodium channels, have acceptable bioavailability properties, and that offer a variety of cores to facilitate rational development of therapeutic agents for use as selective Na$_v$ 1.7 sodium ion channel blockers.

SUMMARY OF THE INVENTION

In one aspect, the invention provides compounds having selective activity as Na$_v$ 1.7 sodium ion channel blockers which have the structure of Formula A$^A$ or Formula A$^B$:

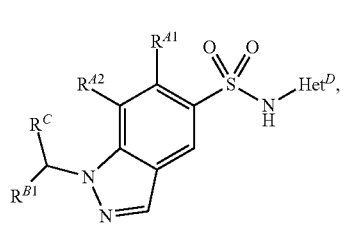

Formula A$^A$

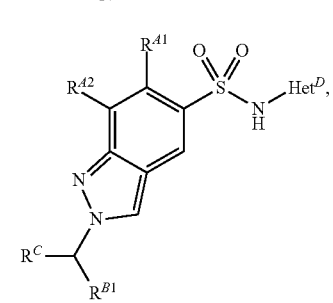

Formula A$^B$ wherein:

"Het$^D$" is an optionally-substituted heteroaryl moiety comprising from 5 to 7-ring atoms and from 1 to 3 heteroatoms which are independently for each occurrence sulfur or nitrogen, and in some embodiments, preferably Het$^D$ is thiazole or fluoropyridine. In some embodiments where Het$^D$ is optionally substituted, preferably the substituent is a halogen, more preferably —Cl or F;

one of $R^{A1}$, or "$R^{A2}$" is —H and the other is —H, $C_{1-4}$ alkyl or a halogen, and when $R^{A1}$ or $R^{A2}$ is a halogen it is preferably —F or —Cl;

$R^{B1}$ is H or $C_{1-6}$ alkyl; and
$R^C$ is:
(A) a substituent of the formula:

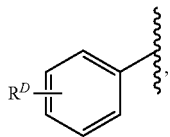

wherein $R^D$ is optionally 1 to 3 substituents which are independently:
(i) halogen, preferably —I, —F, or —Cl;
(ii) amino-alkenyl moiety of the formula [$H_2N$—$(CH_2)_n$—CH═CH—], where "n" is an integer of 1 to 4;
(iii) heterocycloalkyl of the formula:

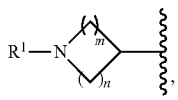

wherein: "n" and "m" are independently 1 to 4; and "$R^i$" is $C_{1-4}$-alkyl or H;
(iv) a moiety of the formula:

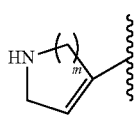

wherein "m" is 1-4;
(v) an aryl moiety which is substituted with a dialkylamino-$C_{1-3}$-alkyl-NH—C(O)— moiety, preferably where the moiety is N-(2-(dimethylamino)ethyl)benz-3-yl-carboxamide;
(vi) a heterobicyclo-moiety of the formula:

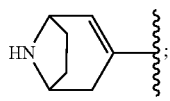

(vii) a substituent of the formula:

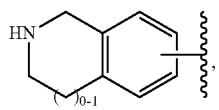

which is optionally substituted with one or more moieties which are, independently: halogen or $C_{1-4}$-alkyl;
(viii) optionally substituted $C_{1-6}$-alkyl moiety, and when selected to be unsubstituted alkyl is preferably methyl, and when selected to be substituted alkyl, preferably the substituents are one or more, independently for each occurrence: (a) halogen; or (b) —N($R^i$)$_2$, where "$R^i$" is independently —H or —$C_{1-6}$-alkyl;

(ix) optionally substituted $C_{1-6}$-alkoxy;
(x) —CN; or
(xi) $C_{1-4}$-alkynyl moiety, optionally substituted, and when selected to be substituted, preferably the substituents are one or more moieties which are independently: (a) $C_{1-6}$-alkyl, optionally substituted, and when substituted, in some embodiments the substitutents are preferably one or more: —N($R^i$)$_2$, where "$R^i$" is independently —H or —$C_{1-6}$-alkyl; (b) halogen; or (c) —N($R^i$)$_2$, where "$R^i$" is independently H or —$C_{1-6}$-alkyl;
(B) a substituent of the formula:

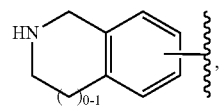

which is optionally substituted with one or more moieties which are, independently: halogen or $C_{1-4}$-alkyl; or
(C) a substituent of the formula:

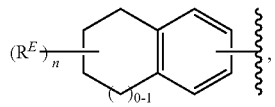

wherein "n" is an integer of from 0 to 3 and $R^E$ is: (i) N($R^i$)$_2$, where "$R^i$" is independently —H or —$C_{1-6}$-alkyl, optionally substituted with CN, OH, or -alkoxy.

In some embodiments, it is preferred for substituents of compounds having the structure of Formula $A^A$ or Formula $A^B$ to have the following substituent definitions:

"$Het^D$" is a heteroaryl moiety comprising from 5 to 7-ring atoms and from 1 to 3 heteroatoms which are independently for each occurrence sulfur or nitrogen, and in some embodiments, preferably $Het^D$ is thiazole or fluoropyridine;

one of "$R^{41}$" or "$R^{42}$" is —H and the other is —H, $C_{1-4}$ alkyl or a halogen, and when $R^{41}$ or $R^{42}$ is a halogen it is preferably —F or —Cl;

$R^{B1}$ is H or $C_{1-6}$ alkyl; and
$R^C$ is:
(A) a substituent of the formula:

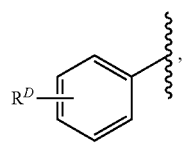

where $R^D$ is optionally 1 to 3 substituents which are:
(i) a halogen, preferably —I, —F, or —Cl;
(ii) an amino-alkenyl moiety of the formula [$H_2N$—$(CH_2)_n$—CH═CH—], where "n" is an integer of 1 to 4;

(iii) a heterocycloalkyl moiety;
(iv) a heterocycloalkenyl of the formula:

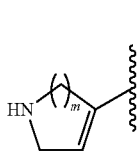

where "m" is 1-4;
(v) an aryl moiety which is substituted with a dialkylamino-$C_{1-3}$-alkyl-NH—C(O)— moiety, preferably where the moiety is N-(2-(dimethylamino)ethyl)benz-3-yl-carboxamide;
(vi) a heterobicyclo-moiety of the formula:

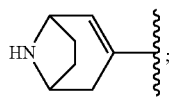

or
(vii) a substituent of the formula:

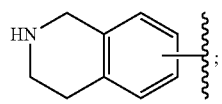

vii. a $C_{1-6}$-alkyl moiety which is preferably methyl,
viii. a $C_{1-6}$-alkoxy;
ix. —CN; or
x. a $C_{1-4}$-alkynyl moiety which is optionally substituted by one or more moieties which are independently: $C_{1-6}$-alkyl; halogen; or —N(R$^i$)$_2$, where "R$^i$" is independently —H or —$C_{1-6}$-alkyl;
(B) a substituent of the formula:

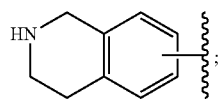

or
(C) a substituent of the formula:

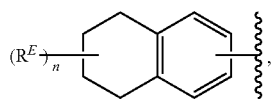

wherein:
"n" is an integer of from 1 to 4; and
R$^E$ is —N(R$^i$)$_2$, where "R$^i$" is independently —H or —$C_{1-6}$-alkyl.

In some embodiments, Het$^D$ is preferably:

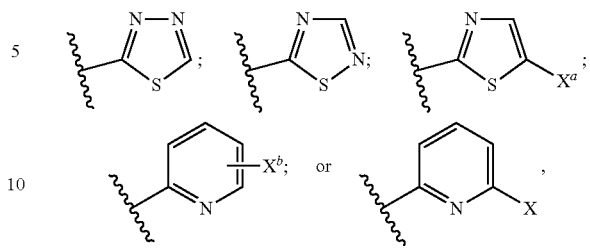

wherein: "X", "X$^a$" and "X$^b$" are independently a halogen. In some embodiments wherein "X"X$^a$" or X$^b$" are halogen, preferably they are —Cl or —F.

In some embodiments, where a compound of Formula A$^A$ or Formula A$^B$ has an R$^{B1}$ substituent which is methyl and an R$^C$ substituent which is heteroaryl or aryl (either of which is optionally substituted) it is preferred for the methyl group to be in a configuration providing the "R" enantiomer of the compound at the methylene carbon.

In one aspect the invention provides a pharmaceutical composition comprising at least one compound of Formula A$^A$ or Formula A$^B$ and at least one pharmaceutically acceptable excipient adapted for administration to a patient via oral, intravenous, subcutaneous, transcutaneous, intramuscular, intradermal, transmucosal, or intramucosal routes of administration.

This invention also provides a pharmaceutical composition comprising an effective amount of at least one compound of Formulae A$^A$ or A$^B$ and an effective amount of at least one other pharmaceutically active ingredient, preferably an opiate agonist or antagonist, a calcium channel antagonist, an NMDA receptor agonist or antagonist, a COX-2 selective inhibitor, or a non-steroidal antiinflamatory compound, and a pharmaceutically acceptable carrier.

In one aspect the invention provides a method of treatment, management, alleviation or amelioration of conditions or disease states which may be treated, managed, alleviated or ameliorated by specific blocking of Nav 1.7 channel activity, the method comprising administering to a patient in need thereof a composition comprising at least one compound of Formulae A$^A$ or A$^B$ in an amount providing a serum level of at least one said compound which sufficient to effect said treatment, management, alleviation or amelioration of the condition or disease state. Preferably the condition to be treated, managed, alleviated or ameliorated is a chronic pain disorder

DETAILED DESCRIPTION OF THE INVENTION

Compounds of the invention, which comprise the core structure of Formulae A$^A$ or A$^B$ (above), surprisingly have great potent activity for blocking Nav 1.7 channels with high specificity when evaluated using the Patch Experss® assay technique described herein. Accordingly, compounds of the invention and formulations of the invention prepared therewith are believed to be useful in providing treatment, management, alleviation or amelioration of conditions or disease states which may be treated, managed, alleviated or ameliorated by specific blocking of Nav 1.7 channel activity. Examples of disease states which may be desirably affected using such therapy may include, but are not limited to, blocking neuropathic pain, for example, postherpetic neuralgia, trigeminal neuralia, diabetic neuropathy, chronic lower back pain, phantom limb pain, pain resulting from cancer and chemotherapy, chronic pelvic pain, complex regional pain syndrome and related neuralgias.

Compounds suitable for use in formulations of the invention, comprise the core structure of Formulae $A^A$ or $A^A$ and surprisingly have potent activity for blocking Nav 1.7 channels with high specificity when evaluated using IonWorks® or PatchXpress® assay techniques described in more detail herein. Accordingly, compounds of the invention and compounds comprising formulations of the invention are believed to be useful in providing treatment, management, alleviation or amelioration of conditions or disease states which may be treated, managed, alleviated or ameliorated by specific blocking of Nav 1.7 channel activity. Examples of disease states which may be desirably affected using such therapy include, but are not limited to, chronic, visceral, inflammatory or neuropathic pain.

As used herein, unless otherwise specified, the term "$Na_v$ 1.7 (equivalently, Nav 1.7) blocker" means a compound of the invention exhibiting a potency ($IC_{50}$) of less than about 2 μM when assayed in accordance with the PatchXpress® assay described herein. Preferred compounds exhibit at least 10-fold selectivity for $Na_v$ 1.7 sodium channels over $Na_v$ 1.5 sodium channels, more preferably at least 100-fold selectivity for $Na_v$ 1.7 sodium channels over $Na_v$ 1.5 sodium channels when functional potency for each channel are compared using the PatchXpress® assay system described herein. Where the term "$Na_v$ 1.7 activity" is used herein, it refers to the ability of a compound to block activity in a $Na_v$ 1.7 sodium ion channel.

As described herein, unless otherwise indicated, the use of a compound in treatment means that an amount of the compound, generally presented as a component of a formulation that comprises other excipients, is administered in aliquots of an amount, and at time intervals, which provides and maintains at least a therapeutic serum level of at least one pharmaceutically active form of the compound over the time interval between dose administration.

Absolute stereochemistry is illustrated by the use of hashed and solid wedge bonds. As shown in Illus-I and Illus-II. Accordingly, the methyl group of Illus-I is emerging from the page of the paper and the ethyl group in Illus-II is descending into the page, where the cyclohexene ring resides within the plane of the paper. It is assumed that the hydrogen on the same carbon as the methyl group of Illus-I descends into the page and the hydrogen on the same carbon as the ethyl group of Illus-II emerges from the page. The convention is the same where both a hashed and solid rectangle are appended to the same carbon as in Illus-III, the Methyl group is emerging from the plane of the paper and the ethyl group is descending into the plane of the paper with the cyclohexene ring in the plane of the paper.

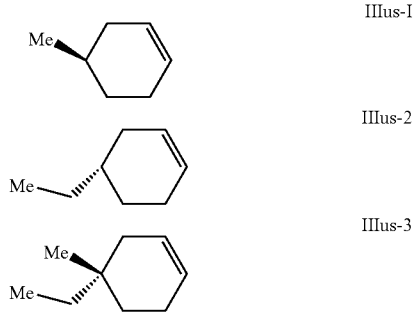

Illus-I

Illus-2

Illus-3

As is conventional, ordinary "stick" bonds or "wavy" bonds are used where there is a mixture of possible isomers present, including a racemic mixture of possible isomers. In some examples presented herein, chiral separation was carried out, for example, using supercritical fluid chromatography (SFC Chromatography) to separate isomers, but absolute configuration for each isomer was not determined. Where this has been accomplished the structure of the separated compound is described with an asterisk indicating the chiral carbon(s) involved and the enantiomers are named as follows: "Ex-#A" (R or S) and "Ex-#B" (S or R); which indicates that pure enantiomers have been separated but the absolute stereochemistry has not been determined.

As used herein, unless otherwise specified, the following terms have the following meanings:

The phrase "at least one" used in reference to the number of components comprising a composition, for example, "at least one pharmaceutical excipient" means that one member of the specified group is present in the composition, and more than one may additionally be present. Components of a composition are typically aliquots of isolated pure material added to the composition, where the purity level of the isolated material added into the composition is the normally accepted purity level of a substance appropriate for pharmaceutical use.

"at least one" used in reference to substituents on a compound or moiety appended to the core structure of a compound means that one substituent of the group of substituents specified is present, and more than one substituent may be bonded to chemically accesible bonding points of the core.

Whether used in reference to a substituent on a compound or a component of a pharmaceutical composition the phrase "one or more", means the same as "at least one";

"concurrently" and "contemporaneously" both include in their meaning (1) simultaneously in time (e.g., at the same time); and (2) at different times but within the course of a common treatment schedule;

"consecutively" means one following the other;

"sequentially" refers to a series administration of therapeutic agents that awaits a period of efficacy to transpire between administering each additional agent; this is to say that after administration of one component, the next component is administered after an effective time period after the first component; the effective time period is the amount of time given for realization of a benefit from the administration of the first component;

"effective amount" or "therapeutically effective amount" is meant to describe the provision of an amount of at least one compound of the invention or of a composition comprising at least one compound of the invention which is effective in treating or inhibiting a disease or condition described herein, and thus produce the desired therapeutic, ameliorative, inhibitory or preventative effect. For example, in treating neuropathic pain with one or more of the compounds described herein "effective amount" (or "therapeutically effective amount") means, for example, providing the amount of at least one compound of Formulae $A^A$ and/or $A^B$ that results in a therapeutic response in a patient afflicted with a neuropathic pain condition ("condition"), including a response suitable to manage, alleviate, ameliorate, or treat the condition or alleviate, ameliorate, reduce, or eradicate one or more symptoms attributed to the condition and/or long-term stabilization of the condition, for example, as may be determined by the analysis of pharmacodynamic markers or clinical evaluation of patients afflicted with the condition;

"patient" and "subject" means an animal, such as a mammal (e.g., a human being) and is preferably a human being;

"prodrug" means compounds that are rapidly transformed, for example, by hydrolysis in blood, in vivo to the parent compound, e.g., conversion of a prodrug of Formulae $A^A$ and/or $A^B$ to a compound of Formulae $A^A$ and/or $A^B$, or to a salt thereof; a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; the scope of this invention includes prodrugs of the novel compounds of this invention;

"solvate" means a physical association of a compound of this invention with one or more solvent molecules; this physical association involves varying degrees of ionic and covalent bonding, including hydrogen bonding; in certain instances the solvate will be capable of isolation, for example when one or more solvent molecules are incorporated in the crystal lattice of the crystalline solid; "solvate" encompasses both solution-phase and isolatable solvates; non-limiting examples of suitable solvates include ethanolates, methanolates, and the like; "hydrate" is a solvate wherein the solvent molecule is $H_2O$.

The term "substituted" means that one or more of the enumerated substituents (or, where a list of substituents are not specifically enumerated, the default substituents specified in this "Definitions" section for the particular type of substrate which contains variable substituents) can occupy one or more of the bonding positions on the substrate typically occupied by "—H", provided that such substitution does not exceed the normal valency rules for the atom in the bonding configuration present in the substrate, and that the substitution ultimate provides a stable compound, e.g., mutually reactive substituents are not present geminal or vicinal to each other, and wherein such a compound is sufficiently robust to survive isolation to a useful degree of purity from a reaction mixture; when the text indicates optional substitution of a moiety (e.g. "optionally substituted") the term means "if present, one or more of the enumerated (or default substituents for the specified substrate) may be present on the substrate in a bonding position normally occupied by a hydrogen atom" in accordance with the definition of "substituted" presented herein;

As used herein, unless otherwise specified, the following terms used to describe moieties, whether comprising the entire definition of a variable portion of a structural representation of a compound of the invention or a substituent appended to a variable portion of a structural representation of a group of compounds of the invention have the following meanings, and unless otherwise specified, the definitions of each term (i.e., moiety or substituent) apply when that term is used individually or as a component of another term (e.g., the definition of aryl is the same for aryl and for the aryl portion of arylalkyl, alkylaryl, arylalkynyl moieties, and the like); moieties are equivalently described herein by structure, typographical representation or chemical terminology without intending any differentiation in meaning, for example, the chemical term "acyl", defined below, is equivalently described herein by the term itself, or by typographical representations "R'—(C=O)—" or "R'—C(O)—", or by the structural representation:

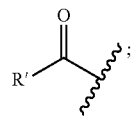

"acyl" means an R'—C(O)—, where R' is linear, branched or cyclic alkyl; linear, branched or cyclic alkenyl; or linear, branched or cyclic alkynyl moeity, each of which moieties can be substituted; wherein the acyl substituent is bonded through the carbonyl carbon to the substrate of which it is a substituent, or —NH—$SO_2$—R', where —R' is as previously defined; non-limiting examples of suitable acyl groups include formyl, acetyl, propanoyl, 2-methylpropanoyl, butanoyl and cyclohexanoyl;

"alkenyl" means an aliphatic hydrocarbon moiety which is not aromatic but includes in its structure at least one constituent of the structure (R'C=CR'$_2$) or (R'C=CR')—, where R' is a defined substituent, for example —H or -alkyl; the alkenyl moiety can be incorporated into a linear hydrocarbon chain, or incorporated into a cyclic hydrocarbon chain (termed "cycloalkenyl") and can comprise further, linear, branched, or cyclic substituents depending from the carbon atoms of the chain, preferably the chain comprises about 2 to about 15 carbon atoms; more preferably from about 2 to about 12 carbon atoms; and more preferably chains comprise from about 2 to about 6 carbon atoms;

the term "substituted alkenyl", unless specified otherwise by a recitation of specific substituents defining the term, means that the alkenyl group is substituted by one or more substituents which are independently for each occurrence: $C_{1-10}$ alkyl, $C_{3-10}$ cycloalkyl, and $C_{1-10}$ alkoxy, wherein each of these moieties are optionally substituted;

the term "substituted alkenyl", unless specified otherwise by a recitation of specific substituents defining the term, means that the alkenyl group is substituted by one or more substituents which are independently for each occurrence: halo, alkyl, aryl, cycloalkyl, cyano, alkoxy and —S(alkyl);

"alkoxy" means a moiety of the structure: alkyl-O— (i.e., the bond to the substrate moiety is through the ether oxygen), wherein the alkyl portion of the moiety is as defined below for alkyl; non-limiting examples of suitable alkoxy groups include methoxy, ethoxy, n-propoxy, isopropoxy, n-butoxy and heptoxy;

"alkoxycarbonyl" means a moiety of the structure alkyl-O—C(O)—, equivalently represented as [alkyl-O—(C=O)—] and also as R—O(C=O)—, where "R" is a defined alkyl moiety, (i.e., the bond to the parent moiety is through the carbonyl carbon) wherein the alkyoxy portion of the moiety is as previously defined; non-limiting examples of suitable alkoxycarbonyl groups include methoxycarbonyl and ethoxycarbonyl;

"alkyl" (including the alkyl portions of other moieties, such as trifluoromethyl-alkyl- and alkoxy-) means an aliphatic hydrocarbon chain comprising from about 1 to about 20 carbon atoms (that is, "$C_{1-20}$ alkyl"), preferably 1 to about 10 carbon atoms (herein "$C_{1-10}$ alkyl"), unless the term is modified by an indication that a shorter chain is contemplated, for example, an alkyl moiety of up to 8 carbon atoms (designated herein "$C_{1-8}$-alkyl"); the term "alkyl", unless specifically limited by another term, for example, "linear", "branched", or "cyclic", includes alkyl moieties which are linear (a hydrocarbon chain with no aliphatic hydrocarbon "branches" appended to it); branched (a main hydrocarbon chain comprising up to the maximum specified number of carbon atoms with a lower-alkyl chain appended to one or more carbon atoms comprising, but not terminating, the main hydrocarbon chain); and cyclic (the main hydrocarbon chain forms an cyclic aliphatic moiety of from 3 carbon atoms, the minimum number necessary to provide a cyclic moiety, up to the maximum number of specified carbon atoms), accordingly when unmodified, the term "$C_{1-X}$alkyl" refers to linear, branched, or cyclic alkyl, and the "$C_{1-X}$" designation means: for a cyclic moiety a ring comprising at minimum 3 carbon atoms up to "X" carbon atoms; for a branched moiety, a main chain of at least 3 carbon atoms up to "X" carbon atoms with at least one linear or branched alkyl moiety bonded to a carbon atom which does not terminate the chain; and for a linear alkyl, a moiety comprising one carbon atom (i.e., -methyl), up to "X" carbon atoms; when the term "alkyl" is modified by "substituted" or "optionally substituted" it means an alkyl group having substituents in accordance with the relevant definitions appearing below; where use of the terms "substituted" or "optionally substituted" modify "alkyl" and substituent moieties are not specifically enumerated, the substituents bonded to the alkyl substrate are independently for each occurrence (in accordance with definitions appearing herein): $C_{1-20}$ alkyl; halogen; -alkoxy; —OH; —CN; alkylthio-; amino, —NH(linear or branched alkyl), —NH(cycloalkyl), —N(alkyl)$_2$, —(C═O)—OH; —C(O)O-alkyl; S(alkyl); or —S(O$_2$)-alkyl; or -aryl; cycloalkyl moieties may alternatively, or in addition, be substituted with one or more, "ring-system substituents" as that term is defined herein; examples of suitable alkyl groups include, but are not limited to, methyl, ethyl, n-propyl, isopropyl, n-butyl, t-butyl, n-pentyl, heptyl, nonyl, decyl, fluoromethyl, trifluoromethyl and cyclopropylmethyl, where the term "alkyl" is indicated with two hyphens (i.e., "-alkyl-" it indicates that the alkyl moiety is bonded in a manner that the alkyl moiety connects a substrate with another moiety, for example, "-alkyl-OH" indicates an alkyl moiety connecting a hydroxyl moiety to a substrate;

"lower alkyl" means a group comprising about 1 to about 6 carbon atoms in the chain (i.e. $C_{1-6}$); non-limiting examples of suitable alkyl groups include methyl (also abbreviated in the structures as "Me-"), ethyl, n-propyl, isopropyl, cyclopropyl, n-butyl, t-butyl, cyclobutyl, n-pentyl, neopentyl, cyclopentyl, n-hexyl, cyclohexyl and the like, fluoromethyl, trifluoromethyl, cyclopropylmethyl, and the like;

"alkylaryl" (or alkaryl) means an alkyl-aryl- group (i.e., the bond to the parent moiety is through the aryl group) wherein the alkyl group is unsubstituted or substituted as defined above, and the aryl group is unsubstituted or substituted as defined below; preferred alkylaryl moieties comprise a lower alkyl group; non-limiting examples of suitable alkylaryl groups include o-tolyl, p-tolyl and xylyl;

in general, as exemplified by the term "alkyl-aryl" defined above, a substituent which is called out by the combination of terms used to define two other substituent fragments indicates that the substituent called out by the last term used is bonded to the substrate whilst the preceeding term called out is bonded in turn to the substituent fragment it preceeds, proceeding right to left to understand the order in which the various fragments are bonded to the substrate;

"alkylsulfinyl" means an alkyl-S(O)— moiety (i.e., the moiety is bonded to a substrate through the sulfur atom of the sulfinyl moiety); "alkylthio" means an alkyl-S— group (i.e., the moiety is bonded to a substrate through the sulfur atom of the moiety); "alkylsulfonyl" means an alkyl-S(O$_2$)— group (i.e., the moiety is bonded to a substrate through the sulfur atom of the sulfonyl moiety), suitable alkyl groups can be unsubstituted or substituted as previously defined; preferred groups are those in which the alkyl group is lower alkyl;

"alkynyl" means an aliphatic hydrocarbon group (chain) comprising at least one moiety of the structure:

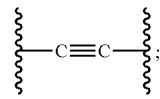

or the structure:

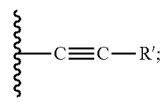

wherein R' is a defined substituent, the alkynyl moiety may be incorporated into a linear or branched hydrocarbon chain, or incorporated into a cyclic hydrocarbon chain (non-aromatic, termed "cycloalkynyl",); preferably hydrocarbon chains of an alkynyl moiety comprises about 2 to about 15 carbon atoms; more preferably alkynyl groups comprise about 2 to about 12 carbon atoms in the chain; and more preferably about 2 to about 4 carbon atoms in the chain;

"amino" means an —NR$_2$ group wherein R is selected independently for each occurrence from —H or alkyl, alkylamino means —NR'$_2$, wherein one R' is -alkyl and the other is —H or -alkyl selected independently for each occurrence, non-limiting examples of alkylamino moieties are —NH—CH$_3$ (methylamino-) and —N(CH$_3$)$_2$ (dimethylamino);

"ammonium ion" means —N$^+$R$_3$, wherein R is independently —H, alkyl, substituted alkyl, or the cationic portion of a dissociated acid capable of producing an ammonium ion from an amine; when not explicitly shown in representations herein the presence of an ammonium ion presumes that a charge-balancing anion is associated with the ammonium ion moiety, which anion is derived from the anionic portion of the acid used to provide said ammonium ion, it will be appreciated that many of the nitrogen atoms present in compounds of the invention can be converted to an ammonium ion thereby providing a salt of the parent compound, which is within the scope of the invention;

"aryl" (sometimes abbreviated "ar") means an aromatic monocyclic or multicyclic ring system comprising about 6 to about 14 carbon atoms (denoted herein also as "$C_{6-14}$-aryl"), preferably about 6 to about 10 carbon atoms ("$C_{6-10}$-aryl"); the aryl group may be optionally substituted with one or more independently selected "ring system substituents" (defined below). Non-limiting examples of suitable aryl groups include phenyl

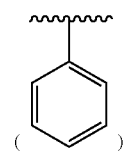

and naphthyl

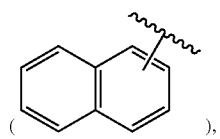

wherein bonding can be through any of the carbons in the aromatic ring, and wherein any ring carbon atoms not participating in a bond to the substrate may have bonded to it a substituent other than —H, independently selected in each instance from the list of "ring-system substituents" defined herein, or as defined in each instance where the term is used in conjunction with an enumerated list of substituents;

"aryloxy" means an aryl-O— group (i.e., the moiety is bonded to a substrate through the ether oxygen) wherein the aryl group is unsubstituted or substituted as defined above; non-limiting examples of suitable aryloxy groups include phenoxy and naphthoxy;

"aryloxycarbonyl" means an aryl-O—C(O)— group (i.e., the bond to a substrate is through the carbonyl carbon) wherein the aryl group is unsubstituted or substituted as previously defined; non-limiting examples of suitable aryloxycarbonyl groups include phenoxycarbonyl and naphthoxycarbonyl;

the term the terms "sulfinyl" means (—SO—), "sulfonyl" means (—S(O$_2$)—), and the term "thio" means (—S—), and in combination with any other substituent terms, mean the same thing, thus, for example: "arylsulfinyl" means an aryl-S(O)— group; "arylsulfonyl" means an aryl-S(O$_2$)— group; and "arylthio" means an aryl-S— group (i.e., the bond of the first-named substituent is to the substrate through the sulfur atom in each case) wherein aryl is unsubstituted or substituted as previously defined;

a "carboxylic acid" moiety means a substituent having the formula "—C(O)—OH", wherein the moiety is bonded to a substrate is through the carbonyl carbon;

"cycloalkyl", also defined above with the "alkyl" definition, means a non-aromatic mono- or multicyclic ring system comprising, unless specified at the point of use otherwise, about 3 to about 20 carbon atoms which may be substituted by a "ring-system substituent" as defined herein; the term includes multicyclic cycloalkyls, for example, 1-decalin, norbornyl, adamantyl and the like;

"halogen" means fluorine, chlorine, bromine, or iodine; preferred halogens are fluorine, chlorine and bromine, a substituent which is a halogen atom means —F, —Cl, —Br, or —I, and "halo" means fluoro, chloro, bromo, or iodo substituents bonded to the moiety defined, for example, "haloalkyl" means an alkyl, as defined above, wherein one or more of the bonding positions on the alkyl moiety typically occupied by hydrogen atoms are instead occupied by a halo group, perhaloalkyl means that all bonding positions not participating in bonding the alkyl substituent to a substrate are occupied by a halogen, for example, perfluoroalkyl, where alkyl is methyl, means —CF$_3$;

"heteroaryl" means an aromatic monocyclic or multicyclic moiety comprising about 5 to about 14 ring atoms, preferably about 5 to about 10 ring atoms, in which one or more of the ring atoms is an element other than carbon, for example nitrogen, oxygen or sulfur, alone or in combination; preferred heteroaryl moieties comprise 5 ring atoms, for example, thiazole thiadiazole, imidazole, isothiazole, oxazole, oxadiazole, or pyrazole; the "heteroaryl" may be optionally substituted at chemically available ring atoms by one or more independently selected "ring-system substituents" (defined below); the prefix aza, azo, oxa, oxo, thia or thio before the heteroaryl root name means that at least a nitrogen, oxygen or sulfur atom, respectively, is present as a ring atom, and in some embodiments 2 or more heteroatoms are present in a ring, for example, a pyrazole or a thiazole moiety; a nitrogen atom of a heteroaryl may be optionally oxidized to the corresponding N-oxide; non-limiting examples of heteroaryl moieties include: pyridyl-,

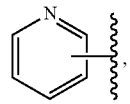

thiophenyl-

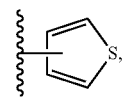

furanyl-,

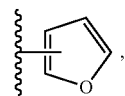

pyrazinyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, furopyridine, for example:

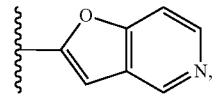

and the like (unless otherwise noted, bonded to the substrate through any available atom that results in a stable bonding arrangement);

"heteroaryl" means an aromatic substituent comprising a monocyclic or multicyclic ring of from 5 to about 14 ring atoms, preferably about 5 to about 10 ring atoms, in which one or more of the ring atoms is an element other than carbon, for example nitrogen, oxygen or sulfur, alone or in combination; preferred heteroaryl moieties comprise 5 ring atoms, for example, thiazole thiadiazole, imidazole, isothiazole, oxazole, oxadiazole, or pyrazole; the "heteroaryl" may be optionally substituted at chemically available ring atoms by one or more independently selected "ring-system substituents" (defined below); the prefix aza, azo, oxa, oxo, thia or thio before the heteroaryl root name means that at least a nitrogen, oxygen or sulfur atom, respectively, is present as a ring atom, and in some embodiments 2 or more heteroatoms are present in a ring, for example, a pyrazole or a thiazole moiety; a nitrogen atom of a heteroaryl can be optionally oxidized to the corresponding N-oxide; non-limiting examples of heteroaryl moieties include: tetrahydroquinolinyl-moiety

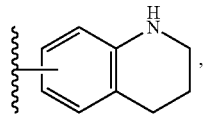

pyridyl-

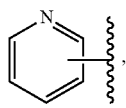

thiopenyl-

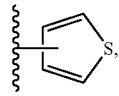

furanyl-

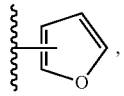

pyrazinyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, furopyridine, for example:

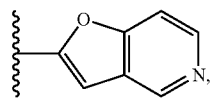

and the like (unless otherwise noted, bonded to the substrate through any available atom that results in a stable bonding arrangement);

"heterocyclyl" (or heterocycloalkyl) means a non-aromatic saturated monocyclic or multicyclic ring-system comprising about 3 to about 10 ring atoms, preferably about 5 to about 10 ring atoms, in which one or more of the atoms in the ring-system is an element other than carbon, for example nitrogen, oxygen or sulfur, alone or in combination, provided that there are no adjacent oxygen and/or sulfur atoms present in the ring system and in some embodiments, preferably, heterocyclyl moieties contain about 5 to about 6 ring atoms;

the prefix aza, oxa or thia before the heterocyclyl root name means that at least one nitrogen, oxygen or sulfur atom, respectively, is present as a ring atom;

a heterocyclyl moiety may be optionally substituted by one or more "ring-system substituents" (defined below) which are selected independently for each occurrence;

the nitrogen or sulfur atom of the heterocyclyl can be optionally oxidized to the corresponding N-oxide, S-oxide or S,S-dioxide;

non-limiting examples of suitable monocyclic heterocyclyl rings include piperidyl, pyrrolidinyl, piperazinyl, morpholinyl, (where unless otherwise noted the moiety is bonded to the substrate through any of ring carbon atoms C2, C3, C5, or C6), as carbon numbers are illustrated:

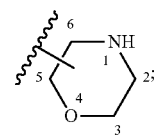

thiomorpholinyl, thiomorpholinyl dione, thiazolidinyl, 1,3-dioxolanyl, 1,4-dioxanyl, tetrahydrofuranyl, tetrahydrothiophenyl, tetrahydrothiopyranyl, and the like;

"Ring-system substituent" means a substituent attached to a carbon atom in the cyclic or heterocyclic portion of an aromatic or non-aromatic moiety that, for example, replaces a bonding position normally occupied by a hydrogen atom on the ring system. Unless modified by exclusions or additions, the term "ring-system substituent" means one or more moieties independently selected from: alkyl, aryl, heteroaryl, aralkyl, alkylaryl, aralkenyl, heteroaralkyl, alkylheteroaryl, heteroaralkenyl, hydroxy (also termed "hydroxyl" when standing alone as a substituent moiety), hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $R^{60}R^{65}N-$, $R^{60}R^{65}N$-alkyl-, $R^{60}R^{65}NC(O)-$ and $R^{60}R^{65}NSO_2-$, wherein $R^{60}$ and $R^{65}$ are each independently: hydrogen, alkyl, aryl, and aralkyl (as defined herein);

"tetrahydropyranyl" moiety means a 6-member cyclic ether of the formula:

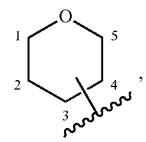

where, the bond line having an open end in the center of the structure and terminated at the other end with a wavy line indicates that the substituent is bonded to the substrate to which it is attached through any of carbon atoms 1 to 5, and wherein any of the bonding positions on carbons 1 to 5 normally occupied by a hydrogen atom, that is, the bonding positions on carbon atoms 1 to 5 which are not occupied by the bond to the substrate may optionally be occupied by specified or optional substituents;

"piperidinyl" means:

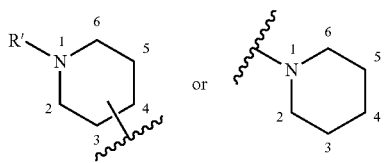

where, the open bond line terminated on one end with a wavy line indicates the ring atom through which the moiety is bonded to the substrate (i.e., any of carbon atoms 2 to 6 (left-hand structure) or the ring nitrogen atom (right-hand structure), which moiety is also optionally substituted on any of the bonding positions on the nitrogen atom or on carbon atoms 2 to 6 of the ring which are not participating in a bond to the substrate, with a "ring-system substituent" or a specified or optional substituent, and wherein R', if present, is either —H or another specified substituent;

"pyridinyl" means:

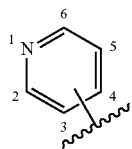

where, the bond-terminated-with-wavy-line indicates that the pyridinyl moiety is bonded to the substrate at any of carbon atoms 2 to 6, and wherein any of the bonding positions on carbons 2 to 6 normally occupied by a hydrogen atom, that is, any position on carbon 2 to 6 which is not the bond to the substrate, may optionally be occupied by a specified substituent;

"pyridinyl" means:

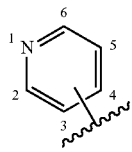

where, the bond-terminated-with-wavy-line indicates that the pyridinyl moiety is bonded to the substrate at any of carbon atoms 2 to 6, and wherein any of the bonding positions on carbons 2 to 6 normally occupied by a hydrogen atom, that is, any position on carbon 2 to 6 which is not the bond to the substrate, may optionally be occupied by a specified substituent;

"quinoline" means:

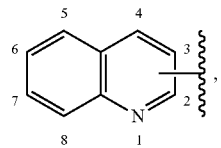

where, the bond-terminated-with-wavy-line indicates that the moiety is bonded to the substrate through any of carbon atoms 2 to 8, and wherein any of the bonding positions on carbon atoms 2 to 8 normally occupied by a hydrogen atom, that is, any bonding positions on carbon atoms 2 to 8 which are not bonded to the substrate, can optionally be occupied by one of a list of enumerated substituents;

for any of the foregoing ring-system moieties, bonding of the moiety through a specific ring carbon atom (or heteroatom) is sometimes described for convenience and "bonded through C—X to C—Y carbon atoms", where "X" and "Y" are integers referring to the carbon atoms, for example, as numbered in the examples above;

"hydroxyl moiety" and "hydroxy" means an HO— group, "hydroxyalkyl" means a substituent of the formula: "HO-alkyl-", wherein the alkyl group is bonded to the substrate and may be substituted or unsubstituted as defined above; preferred hydroxyalkyl moieties comprise a lower alkyl; Non-limiting examples of suitable hydroxyalkyl groups include hydroxymethyl and 2-hydroxyethyl; and bonding sequence is indicated by hyphens where moieties are represented in text, for example -alkyl, indicates a single bond between a substrate and an alkyl moiety, -alkyl-X, indicates that an alkyl group bonds an "X" substituent to a substrate, and in structural representation, bonding sequence is indicated by a wavy line terminating a bond representation, for example:

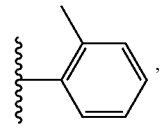

indicates that the methylphenyl moiety is bonded to a substrate through a carbon atom ortho to the methyl substituent, while a bond representation terminated with a wavy line and drawn into a structure without any particular indication of a atom to which it is bonded indicates that the moiety may be bonded to a substrate via any of the atoms in the moiety which are available for bonding, for example:

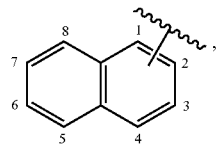

indicates that the naphthalene moiety may be bonded to the substrate through any of carbons 1 to 8.

Any carbon or heteroatom with unsatisfied valences in the text, schemes, examples, structural formulae, and any Tables herein is assumed to have a hydrogen atom or atoms of sufficient number to satisfy the valences.

One or more compounds of the invention may also exist as, or optionally be converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, and hemisolvate, including hydrates (where the solvent is water or aqueous-based) and the like are described by E. C. van Tonder et al, *AAPS PharmSciTech.*, 5(1), article 12

(2004); and A. L. Bingham et al, *Chem. Commun.*, 603-604 (2001). A typical, non-limiting, process involves dissolving the inventive compound in desired amounts of the desired solvent (for example, an organic solvent, an aqueous solvent, water or mixtures of two or more thereof) at a higher than ambient temperature, and cooling the solution, with or without an antisolvent present, at a rate sufficient to form crystals which are then isolated by standard methods. Analytical techniques such as, for example I.R. spectroscopy, show the presence of the solvent (including water) in the crystals as a solvate (or hydrate in the case where water is incorporated into the crystalline form).

The term "pharmaceutical composition" as used herein encompasses both the bulk composition and individual dosage units comprised of more than one (e.g., two) pharmaceutically active agents such as, for example, a compound of the present invention and an additional agent as described herein, along with any pharmaceutically inactive excipients. As will be appreciated by the ordinarily skilled artisan, excipients are any constituent which adapts the composition to a particular route of administration or aids the processing of a composition into a dosage form without itself exerting an active pharmaceutical effect. The bulk composition and each individual dosage unit may contain fixed amounts of the afore-said "more than one pharmaceutically active agents". The bulk composition is a pharmaceutical composition which has not yet been formed into individual dosage units.

This invention also includes the compounds of this invention in isolated and purified form obtained by routine techniques. Polymorphic forms of the compounds of Formulae $A^A$ and/or $A^B$, and of the salts, solvates and prodrugs of the compounds of Formulae $A^A$ and/or $A^B$, are intended to be included in the present invention. Certain compounds of the invention may exist in different isomeric (e.g., enantiomers, diastereoisomers, atropisomers) forms. The invention contemplates all such isomers both in pure form and in admixture, including racemic mixtures. Enol forms are also included.

All stereoisomers (for example, geometric isomers, optical isomers and the like) of the present compounds (including prodrugs of compounds of the invention as well as the salts and solvates of the inventive compounds and their prodrugs), such as those which may exist due to asymmetric carbons present in a compound of the invention, and including enantiomeric forms (which may exist even in the absence of asymmetric carbons), rotameric forms, atropisomers, and diastereomeric forms, are contemplated within the scope of this invention. Individual stereoisomers of the compounds of the invention may be isolated in a pure form, for example, substantially free of other isomers, or may be isolated as an admixture of two or more stereoisomers or as a racemate. The chiral centers of the present invention can have the S or R configuration as defined by the *IUPAC* 1974 Recommendations. The use of the terms "salt", "solvate" "prodrug" and the like, is intended to equally apply to salts, solvates and prodrugs of isolated enantiomers, stereoisomer pairs or groups, rotamers, tautomers, or racemates of the inventive compounds.

Where diasteromeric mixtures can be separated into their individual diastereomers on the basis of their physical chemical differences by methods well known to those skilled in the art, for example, by chiral chromatography and/or fractional crystallization. As is known, enantiomers may also be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individually isolated diastereomers to the corresponding enantiomers.

Where the compounds of the invention form salts by known, ordinary methods, these salts are also within the scope of this invention. Reference to a compound of the invention herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the invention contains both a basic moiety, for example, but not limited to, a nitrogen atom, for example, an amine, pyridine or imidazole, and an acidic moiety, for example, but not limited to a carboxylic acid, zwitterions ("inner salts") may be formed and are included within the term "salt(s)" as used herein. Pharmaceutically acceptable (i.e., non-toxic, physiologically acceptable salts) are preferred. Salts of the compounds of the invention may be formed, for example, by reacting a compound of the invention with an amount of acid or base, for example, an equivalent amount, in a medium in which the salt precipitates or in an aqueous medium wherein the product is obtained by lyophilization. Acids (and bases) which are generally considered suitable for the formation of pharmaceutically useful salts from basic (or acidic) pharmaceutical compounds are discussed, for example, by S. Berge et al., *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in The Orange Book (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference.

In general, pharmaceutically acceptable acid addition salts include, but are not limited to, acetates, including trifluoroacetate salts, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

In general, pharmaceutically acceptable basic salts include, but are not limited to, ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexyl-amine, choline, nitromethamine, and salts with amino acids such as arginine, lysine and the like. Basic nitrogen-containing groups may be converted to an ammonium ion or quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid and base salts are intended to be pharmaceutically acceptable salts within the scope of the invention and all acid and base salts are considered equivalent to the free forms of the corresponding compounds for purposes of the invention.

Compounds of the invention, their salts and solvates and prodrugs thereof, may exist in different tautomeric forms. All such forms are embraced and included within the scope of the invention, for example, ketone/enol tautomeric forms, imine-enamine tautomeric forms, and for example heteroaromatic forms such as the following moieties:

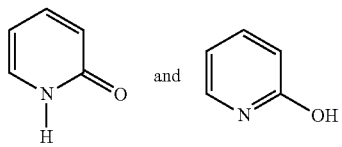 [SMILES: O=c1cccc[nH]1 ; Oc1ccccn1]

are considered equivalent in certain embodiments of this invention.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or other processes described herein or well known to the skilled artisan, and providing said compound in sufficient purity to be characterized by standard analytical techniques described herein or well known to the skilled artisan.

A functional group in a compound termed "protected" means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When a variable (e.g., aryl, heterocycl, $R^3$, etc.) appears more than once in any moiety or in any compound of the invention, the selection of moieties defining that variable for each occurrence is independent of its definition at every other occurrence unless specified otherwise in the variable definition.

As used herein, the term "composition" is intended to encompass a product comprising the specified ingredients in the specified amounts, and any product which results, directly or indirectly, from combination of the specified ingredients in the specified amounts.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. Examples of isotopes that may be preferentially incorporated into compounds of the invention include isotopes of hydrogen, carbon, nitrogen, oxygen, phosphorus, fluorine and chlorine, for example $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Additionally, the compounds of the invention may be modified to include a positron or gamma-emitting isotope, for example, $^{11}C$, $^{13}N$, $^{15}O$, $^{18}F$, $^{62}Cu$, $^{64}Cu$, $^{68}Ga$, $^{76}Br$, $^{82}Rb$, $^{125}I$, and $^{124}I$, which are useful in carrying out tomographic studies when compounds labeled with these types of isotopes are administered to study subjects.

Certain isotopically-labeled compounds of the invention (e.g., those labeled with $^{3}H$ or $^{18}F$) are useful in compound and/or substrate tissue distribution assays. Tritiated (i.e., $^{3}H$) fluorinated (i.e. $^{18}F$) isotopes are particularly preferred for their ease of preparation and detection. As will be understood, isotope substitution carried out by employing principally an isotope heavier than the prepondence normally occurring in nature, for example, replacing protium with deuterium (i.e., $^{2}H$) in certain critical positions in a compound may afford certain therapeutic advantages resulting from greater metabolic stability (e.g., increased in vivo half-life or reduced dosage requirements) and hence may be preferred in some circumstances. This type of isotopically labeled compound of the invention may generally be prepared from precursors obtained by following procedures analogous to those disclosed in the Schemes and/or in the Examples herein below, by substituting an appropriate isotopically labeled reagent for a non-isotopically labeled reagent or by using well-known schemes for the preparation of labeled compounds. In view of the foregoing, all such compounds are included also in the present invention.

In one aspect, as mentioned above, the present invention provides pharmaceutical formulations (pharmaceutical compositions) suitable for use in selectively blocking $Na_v1.7$ sodium channels found in sensory and sympathetic neurons, comprising at least one compound of Formula $A^A$ or Formula $A^B$.

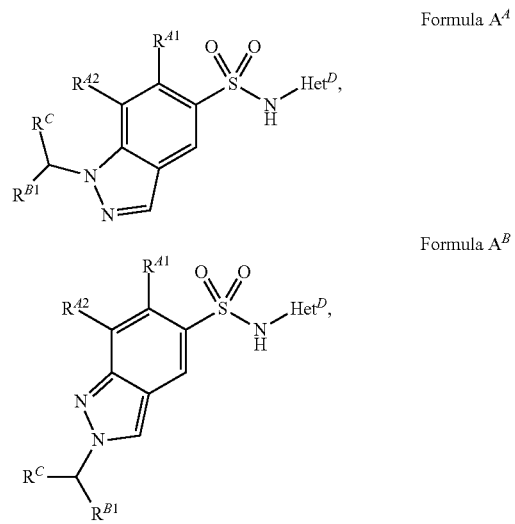

wherein ($Het^D$), ($R^{A1}$), ($R^{A2}$), ($R^{B1}$), and ($R^C$) have been defined herein, and at least one pharmaceutically acceptable carrier (described below).

It will be appreciated that pharmaceutically formulations of the invention may comprise more than one compound of Formulae $A^A$ and/or $A^B$, for example, the combination of two or three of such compounds, each of which is present in the formulation by adding to the formulation the desired amount of the compound in a pharmaceutically acceptably pure form. It will be appreciated that compositions of the invention may comprise, in addition to one or more of the compounds of Formulae $A^A$ and/or $A^B$, one or more other compounds which also have pharmacological activity, for example those described below.

While formulations of the invention may be employed in bulk form, it will be appreciated that for most applications the inventive formulations will be incorporated into a dosage form suitable for administration to a patient, each dosage form comprising an amount of the selected formulation which contains an effective amount of said one or more compounds of Formulae AA and/or AB. Examples of suitable dosage forms include, but are not limited to, dosage forms adapted for: (i) oral administration, e.g., a liquid, gel, powder, solid or semi-solid pharmaceutical composition which is loaded into a capsule or pressed into a tablet and may comprise additionally one or more coatings which modify its release properties, for example, coatings which impart delayed release or formulations which have extended release properties; (ii) a dosage form adapted for intramuscular administration (IM), for example, an injectable solution or suspension, and which may be adapted to form a depot having extended release properties; (iii) a dosage form adapted for intravenous administration (IV), for example, a solution or suspension, for example, as an IV solution or a concentrate to be injected into a saline IV bag; (iv) a dosage form adapted for administration through tissues of the oral cavity, for example, a rapidly dissolving tablet, a lozenge, a solution, a gel, a sachette or a needle array suitable for providing intramucosal administration; (v) a dosage form adapted for administration via the mucosa of the nasal or upper respiratory cavity, for example a solution, suspension or emulsion formulation for dispersion in the nose or airway; (vi) a dosage form adapted for transdermal administration, for example, a patch, cream or gel; (vii) a dosage form adapted for intradermal administration, for example, a microneedle array; and (viii) a dosage form adapted for delivery via rectal or vaginal mucosa, for example, a suppository.

For preparing pharmaceutical compositions from the compounds described by this invention, generally pharmaceutically active compounds are combined with one or more pharmaceutically inactive excipients. These pharmaceutically inactive excipients impart to the composition properties which make it easier to handle or process, for example, lubricants or pressing aids in powdered medicaments intended to be tableted, or adapt the formulation to a desired route of administration, for example, excipients which provide a formulation for oral administration, for example, via absorption from the gastrointestinal tract, transdermal or transmucosal administration, for example, via adhesive skin "patch" or buccal administration, or injection, for example, intramuscular or intravenous, routes of administration. These excipients are collectively termed herein "a carrier".

Pharmaceutical compositions may be solid, semi-solid or liquid. Solid form preparations may be adapted to a variety of modes of administration and include powders, dispersible granules, mini-tablets, beads, and the like for example, for tableting, encapsulation, or direct administration. Typically formulations may comprise up to about 95 percent active ingredient, although formulations with greater amounts may be prepared.

Liquid form preparations include solutions, suspensions and emulsions. Examples of liquid forms of medicament include, but are not limited to, water or water/surfactant mixtures, for example a water-propylene glycol solution, which may be employed in the preparation of formulations intended, for example, for parenteral injection, for example, as a solvent or as a suspending medium for the preparation of suspensions and emulsions where a medicament comprises constituents which are insoluble in water or water/surfactant mixtures. Liquid form preparations may also include solutions or suspensions for intranasal administration and may also include, for example, viscosity modifiers to adapt the formulation for application to particular mucosa tissues accessible via nasal administration.

Aerosol preparations, for example, suitable for administration via inhalation or via nasal mucosa, may include solutions and solids in powder form, which may be in combination with a pharmaceutically acceptable propellant, for example, an inert compressed gas, e.g. nitrogen. Also included are solid form preparations which are intended to be converted, shortly before use, to a suspension or a solution, for example, for oral or parenteral administration. Examples of such solid forms include freeze dried formulations and liquid formulations adsorbed into a solid absorbent medium.

The compounds of the invention may also be deliverable transdermally or transmucosally, for example, from a liquid, suppository, cream, foam, gel, or rapidly dissolving solid form. It will be appreciated that transdermal compositions may take also the form of creams, lotions, aerosols and/or emulsions and may be provided in a unit dosage form which includes a transdermal patch of any known in the art, for example, a patch which incorporates either a matrix comprising the pharmaceutically active compound or a reservoir which comprises a solid or liquid form of the pharmaceutically active compound.

Examples of pharmaceutically acceptable carriers and methods of manufacture for various compositions mentioned above may be found in A. Gennaro (ed.), Remington: The Science and Practice of Pharmacy, $20^{th}$ Edition, (2000), Lippincott Williams & Wilkins, Baltimore, Md.

Preferably, the pharmaceutical preparation is in a unit dosage form. In such form, the preparations subdivided into suitably sized unit doses containing appropriate quantities of the active component, e.g., an effective amount to achieve the desired purpose.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

In another embodiment the present invention provides for treatment, management, prevention, alleviation or amelioration of conditions or disease states which may be treated, managed, prevented, alleviated or ameliorated by specific blocking of Nav 1.7 channel activity, for example, blocking neuropathic pain, for example, post herpetic neuralgia, trigeminal neuralgia, diabetic neuropathy, chronic lower back pain, phantom limb pain, chronic pelvic pain, vulvodynia, complex regional pain syndrome and related neuralgias, pain associated with maycer and chemotherapy, pain associate with HIV, and HIV treatment-induced neuropathy, nerve injury, root avulsions, painful traumatic mononeuropathy, painful polyneuropathy, erythromyelalgia, paroxysmal extreme pain disorder, small fiber neuropathy, burning mouth syndrome, central pain syndromes (potentially caused by virtually any lesion at any level of the nervous system), postsurgical pain syndromes (e.g., post mastectomy syndrome, post thoracotomy syndrome, stump pain)), bone and joint pain (osteoarthritis), repetitive motion pain, dental pain, myofascial pain (muscular injury, fibromyalgia), perioperative pain (general surgery, gynecological), chronic pain, dysmenorhea, pain associated with angina, inflammatory pain of varied origins (e.g. osteoarthritis, rheumatoid arthritis, rheumatic disease, teno-synovitis and gout), shoulder tendonitis or bursitis, gouty arthritis, and aolymyalgia rheumatica, primary hyperalgesia, secondary hyperalgesia, primary allodynia, secondary allodynia, or other pain caused by central sensitization, complex regional pain syndrome, chronic arthritic pain and related neuralgias acute pain, migraine, migraine headache, headache pain, cluster headache, non-vascular headache, traumatic nerve injury, nerve compression or entrapment, and neuroma pain.

In another embodiment the present invention provides for treatment, management, alleviation or amelioration of conditions or disease states which may be treated, managed, alleviated or ameliorated by specific blocking of Nav 1.7 channel activity, for example, blocking neuropathic pain, for example, postherpetic neuralgia, trigeminal neuralia, diabetic neuropathy, chronic lower back pain, phantom limb pain, pain resulting from cancer and chemotherapy, chronic pelvic pain, complex regional pain syndrome and related neuralgias. In accordance with the present invention, treatment, alleviation, amelioration, or management of a disease state amenable to blocking $Na_v1.7$ channel activity, for example a state of neuropathic pain, comprises administering to a patient in need thereof an effective amount of one or more compounds of Formulae $A^A$ and/or $A^B$, or a pharmaceutically acceptable salt of one or more compounds of Formulae $A^A$ and/or $A^B$.

In some embodiments it is preferred to administer one or more compounds of Formulae $A^A$ and/or $A^B$, or a salt thereof.

In some embodiments it is preferred for the compound to be administered in the form of a pharmaceutical composition comprising the compound of Formulae $A^A$ and/or $A^B$, or a salt thereof, and at least one pharmaceutically acceptable carrier (described below). It will be appreciated that pharmaceutically formulations of the invention may comprise more than one compound of Formulae $A^A$ and/or $A^B$ or a salt thereof, for example, the combination of two or three compounds of Formulae $A^A$ and/or $A^B$, each present by adding to the formulation the desired amount of the compound or a salt thereof which has been isolated in a pharmaceutically acceptably pure form.

As mentioned above, administration of a compound of Formulae $A^A$ and/or $A^B$ in accordance with the present invention is preferably accomplished by incorporating the compound into a pharmaceutical formulation incorporated into a dosage form, for example, one of the above-described dosage forms comprising an effective amount of at least one compound of Formulae $A^A$ and/or $A^B$ (e.g., 1, 2 or 3, or 1 or 2, or 1, and usually 1 compound of Formulae $A^A$ and/or $A^B$), or a pharmaceutically acceptable salt thereof, for example. Methods for determining safe and effective administration of compounds which are pharmaceutically active, for example, a compound of Formulae $A^A$ and/or $A^B$, are known to those skilled in the art, for example, as described in the standard literature, for example, as described in the "Physicians' Desk Reference" (PDR), e.g., 1996 edition (Medical Economics Company, Montvale, N.J. 07645-1742, USA), the Physician's Desk Reference, 56$^{th}$ Edition, 2002 (published by Medical Economics company, Inc. Montvale, N.J. 07645-1742), or the Physician's Desk Reference, 57$^{th}$ Edition, 2003 (published by Thompson PDR, Montvale, N.J. 07645-1742); the disclosures of which is incorporated herein by reference thereto. The amount and frequency of administration of the compounds of the invention and/or the pharmaceutically acceptable salts thereof will be regulated according to the judgment of the attending clinician considering such factors as age, condition and size of the patient as well as severity of the symptoms being treated. Compounds of the instant invention may be administered at a total daily dosage of up to 1,000 mg, which may be administered in one daily dose or may be divided into two to four doses per day.

In general, in what ever form administered, the dosage form administered will contain an amount of at least one compound of Formulae $A^A$ and/or $A^B$, or a salt thereof, which will provide a therapeutically effective serum level of the compound in some form for a period of at least 2 hours, preferably at least four hours, and preferably longer. In general, as is known in the art, dosages of a pharmaceutical composition providing a therapeutically effective serum level of a compound of the invention, e.g., a compound of Formulae $A^A$ and/or $A^B$, may be spaced in time to provide serum level meeting or exceeding the minimum therapeutically effective serum level on a continuous basis throughout the period during which treatment is administered. As will be appreciated the dosage form administered may also be in a form providing an extended release period for the pharmaceutically active compound which will provide a therapeutic serum level for a longer period, necessitating less frequent dosage intervals. As mentioned above, a composition of the invention may incorporate additional pharmaceutically active components or be administered simultaneously, contemporaneously, or sequentially with other pharmaceutically active compositions as may be additionally needed in the course of providing treatment. Such additional therapeutic agents may include, for example, i) opiate agonists or antagonists, ii) calcium channel antagonists, iii) NMDA receptor agonists or antagonists, iv) COX-2 selective inhibitors, and v) non-steroidal anti-inflammatory drugs ("NSAID").

Those skilled in the art will appreciate that treatment protocols utilizing at least one compound of Formulae $A^A$ and/or $A^B$ may be varied according to the needs of the patient. Thus, compounds of Formulae $A^A$ and/or $A^B$ used in the methods of this invention may be administered in variations of the protocols described above. For example, the compounds of this invention may be administered discontinuously rather than continuously during the treatment cycle.

Other embodiments of this invention are directed to managing, ameliorating, alleviating or treating disease states which include, but are not limited to those described above, wherein the therapy is provided by administering one or more compounds of Formulae $A^A$ and/or $A^B$, or a pharmaceutical composition comprising one or more compounds of Formulae $A^A$ and/or $A^B$, preferably administering a compound defined in Table I, Table II, or Ex-19, presented herein.

Examples of the preparation of compounds of the invention are shown next. In each of the Examples, the identity of the compounds prepared were confirmed by a variety of techniques. In all cases the compounds were analyzed by LC/MS.

LC/MS determinations used either an Agilent YMC J'Sphere H-80 (3×50 mm) 5 μm column using mobile phase containing A: 0.1% Trifluoroacetic acid in water and B: acetonitrile with a gradient from 95:5 (A:B) to 0:100 (A:B) over 3.6 min and 0:100 (A:B) for 0.4 min at a flow rate of 1.4 mL/min, UV detection at 254 and 220 nm and Agilent 1100 quadrupole mass spectrometer or an Agilent TC-C18 (2.1×50 mm) 5 μm column using mobile phase containing A: 0.0375% Trifluoroacetic acid in water and B: 0.01875% Trifluoroacetic acid in acetonitrile with a gradient from 90:10 (A:B) for 0.4 min to 90:10 to 0:100 (A:B) over 3 min and 10:90 (A:B) for 0.6 min at a flow rate of 0.8 mL/min, UV detection at 254 and 220 nm and Agilent 6110 quadrupole mass spectrometer.

For some compounds, the identity of the compound was verified by proton NMR and high-resolution MS. Proton NMR was were acquired using a Varian Unity-Inova 400 MHz NMR spectrometer equipped with a either a Varian 400 ATB PFG 5 mm, Nalorac DBG 400-5 or a Nalorac IDG 400-5 probe in accordance with standard analytical techniques, unless specified otherwise, and results of spectral analysis are reported."

High resolving power accurate mass measurements were acquired by use of a Bruker Daltonics 7T Fourier transform ion cyclotron resonance (FTICR) mass spectrometer. Samples were dissolved in acetonitrile:water:acetic acid (50: 50:0.1% v/v), and ionized by use of electrospray ionization (ESI) yielding [M+H]+ and/or [M+Na]+. External calibration was accomplished with oligomers of polypropylene glycol (PPG, average molecular weight 1000 Da).

Next is listed the equipment and conditions used to characterize the compounds prepared in accordance with the Example which follow.

For all electrophysiology experiments, offline analysis was used to correct for current rundown and to determine percent inhibition as a function of drug concentration. $IC_{50}$ values were determined by fitting to the Hill equation.

Cell Based Assays for $Na_v$ 1.7 and $Na_v$ 1.5 Activity

Compounds were tested on human Nav1.7 and Nav1.5 channels stably expressed in HEK 293 cells. Sodium current measurements on IonWorks Quattro: An automated patch-clamp assay on the IonWorks Quattro platform (Molecular Devices) was used to measure state-dependent inhibition of human Nav1.7 and 1.5 channels. Cells were sealed on a planar substrate using the Population Patch Plate (PPC) technology. Electrical access was obtained using both nystatin and amphotericin. A double-pulse protocol was used for the determination of $IC_{50}$ values for inactivated state block. Nav1.7 and Nav1.5 expressing cells were voltage clamped at −100 mV and −110 mV, respectively. A depolarizing prepulse to −10 mV (Nav1.7) or −30 mV (Nav1.5) for 1000 ms followed by a 10 ms repolarization to −100 mV (Nav1.7) or −110 mV (Nav1.5) was given to generate fractional channel inactivation of 50%, followed by a 10 ms test pulse to −10 mV (Nav1.7) or −30 mV (Nav1.5) to measure peak current in control conditions and after compound addition. The following recording solutions were used (mM). External: 150 NaCl, 2 $CaCl_2$, 5 KCl, 1 $MgCl_2$, 10 HEPES, 12 Dextrose; internal: 120 CsF, 30 CsCl, 10 EGTA, 5 HEPES, 5 NaF, 2 $MgCl_2$.

Sodium Current Measurements on the PatchXpress 7000®:

To measure inactivated state block of sodium channels, test compounds were characterized in an automated PatchXpress® assay (Molecular Devices) using a double-pulse protocol on human Nav1.7 and Nav1.5 channels stably expressed in HEK 293 cells. Cells were held at a potential 20 mV negative to V0.5 inact. An 8000 ms pre-pulse 7 mV positive to V0.5 inact was given followed by a hyperpolarizing 2 ms pulse to −120 mV and a 20 ms test pulse to −20 mV. Protocol was applied to cells in the absence, presence of compound and after washout. The temperature of PatchXpress instruments was maintained at 22° C. The following recording solutions were used. Internal solution (mM): 30 CsCl, 5 HEPES, 10 EGTA, 120 CsF, 5 NaF, 2 $MgCl_2$. External solution (mM): 120 NMDG, 40 NaCl, 1 KCl, 0.5 MgCl2, 5 HEPES, 2.7 CaCl2.

EXAMPLES

In the examples that follow, unless otherwise noted, starting materials are articles of commerce and used in the reactions as received. Unless otherwise noted, all intermediates are used in subsequent reaction steps in the form and purity provided by the procedure related for their preparation.

Preparation of compounds of the invention is generally carried out, with Reference to Scheme I, II, and III, below, by reaction of an appropriately-substituted 1H or 2H indazole (for example, 5-bromo-1H-indazole, 5-bromo-2H-indazole or 5-bromo-6-fluoro-1H-indazole, articles of commerce) with benzyl mercaptan in the presence of an appropriate Pd catalyst and ligand to produce the corresponding 5-benzothio-indazole adduct. After reacting the benzothio-adduct indazole with an appropriate alcohol or aryl halide precursor to couple the 1H or 2H nitrogen of the indazole, to the substituent supplied by the precursor, the product indazole is converted to the thiadiazole adduct by replacing the benzothio-moiety with a thiadiazole. Alternatively, formation of 6-fluoro-1H-indazole-5-sulfonyl chloride from the 5-(benzylthio)-6-fluoro-1H-indazole followed by formation of the N-(2,4-dimethoxybenzyl)-6-fluoro-N-(aryl)-1H-indazole-5-sulfonamide using an appropriate N-(2,4-dimethoxybenzyl)-aryl-amine then Mitsunobu reaction using variety of alcohols and appropriate indazole sulfonamide core followed by trifluoroacetic acid global deprotection yielded to compounds in Example 1, 2 and 3 as well as compounds in Table I, II and III.

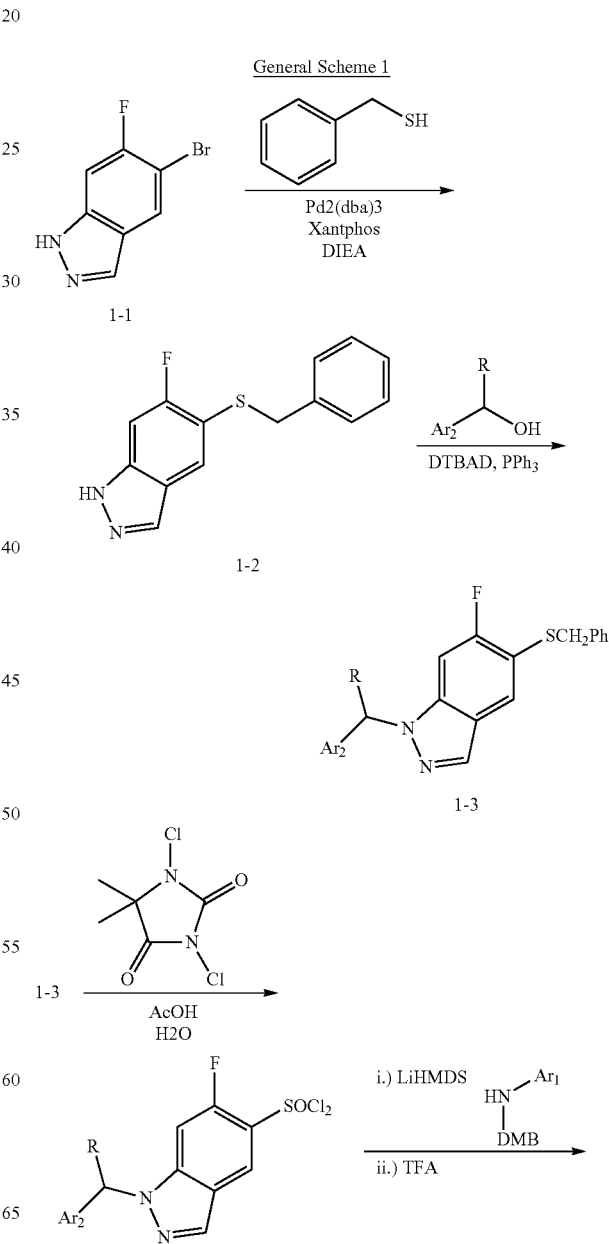

Example 1
Preparation of 6-fluoro-1-((1,2,3,4-tetrahydroisoquinolin-8-yl)methyl)-N-(1,2,4-thiadiazol-5-yl)-1H-indazole-5-sulfonamide (Ex-1) from 5-(Benzylthio)-6-fluoro-1H-indazole
SCHEME A:
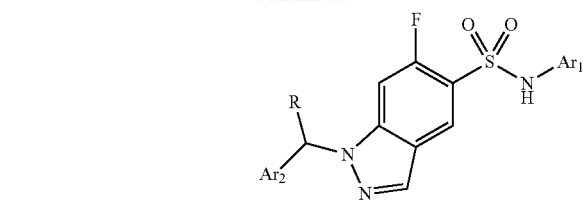
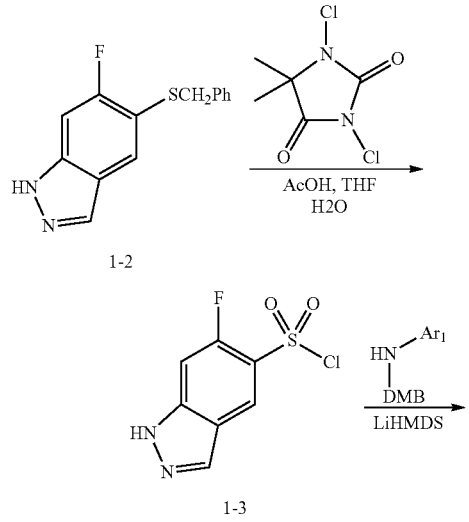
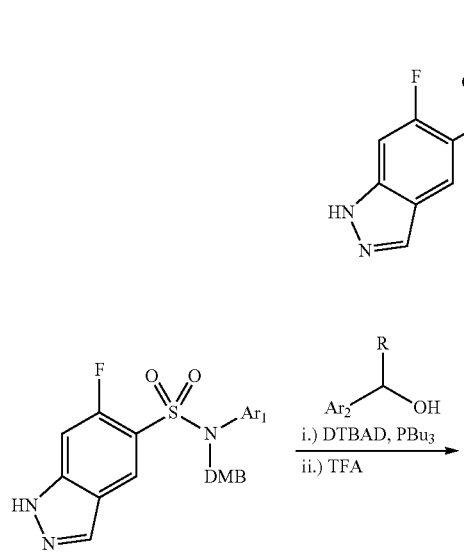
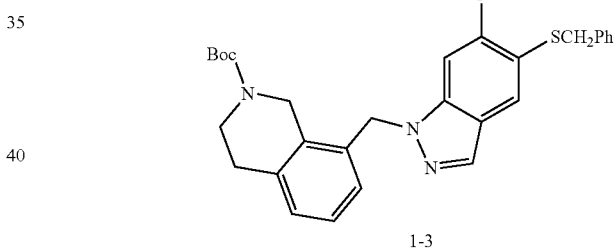
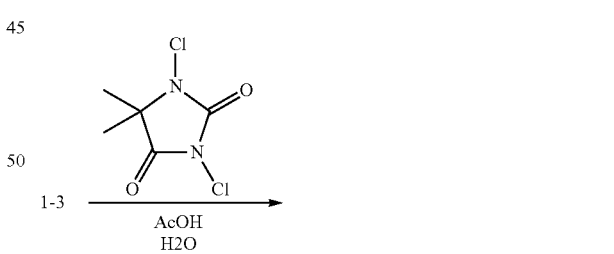
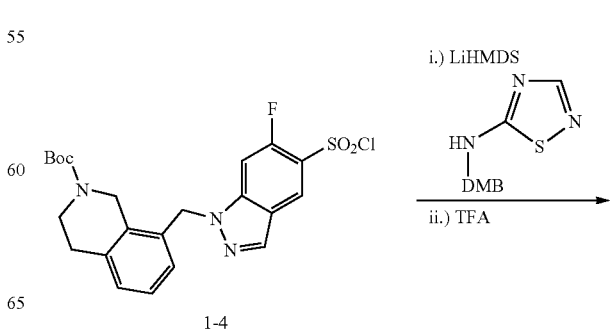

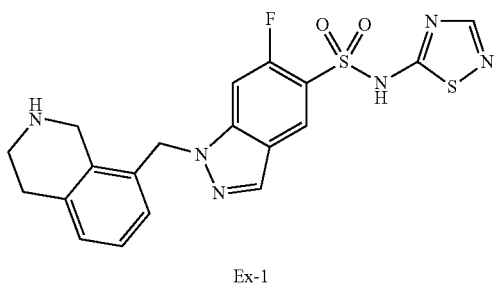

Ex-1

5-(benzylthio)-6-fluoro-1H-indazole (1-2)

A solution of 5-bromo-6-fluoro-1H-indazole (1-1, 1.0 g, 5.08 mmol, 1.0 equiv), Xantphos (0.294 g, 0.508 mmol, 0.1 equiv), and $Pd_2(dba)_3$ (0.465 g, 0.508 mmol, 0.1 equiv) was made in dioxane (25 mL) followed by the addition of DIEA (1.77 mL, 10.15 mmol, 2.0 equiv) and benzylmercaptan (0.630 mL, 5.33 mmol, 1.05 equiv) and the reaction was stirred at 120° C. overnight. The reaction mixture concentrated in vacuo and purified using normal phase chromatography. ESI+ MS $[M+H]^+$ $C_{14}H_{11}FN_2S$: 259.9 found, 259.3 required.

tert-butyl 8-((5-(benzylthio)-6-fluoro-1H-indazol-1-yl)methyl)-3,4-dihydroisoquinoline-2(1H)-carboxylate (1-3)

To a solution of 5-(benzylthio)-6-fluoro-1H-indazole (1-2, 0.35 g, 1.35 mmol, 1.0 equiv) and tert-butyl 8-(hydroxymethyl)-3,4-dihydroisoquinoline-2(1H)-carboxylate (0.53 g, 2.03 mmol, 1.5 equiv) in THF (6.77 mL) at 0° C. was added polymer supported triphenylphosphine (0.71 g, 2.71 mmol, 2.0 equiv) followed by di-tertbutylazodicarboxylate (0.62 g, 2.71 mmol, 2.0 equiv) and the reaction mixture was stirred at 0° C. for 2.5 hours. The reaction was concentrated and purified using normal phase chromatography to yield the desired regioisomer. ESI+ MS $[M+H]^+$ $C_{29}H_{30}FN_3O_2S$: 504.3 found, 504.6 required.

tert-butyl 8-((5-(chlorosulfonyl)-6-fluoro-1H-indazol-1-yl)methyl)-3,4-dihydroisoquinoline-2(1H)-carboxylate (1-4)

To a solution of tert-butyl 8-((5-(benzylthio)-6-fluoro-1H-indazol-1-yl)methyl)-3,4-dihydroisoquinoline-2(1H)-carboxylate (1-3, 0.34 g, 0.67 mmol, 1.0 equiv) in ACN (3.16 mL), AcOH (0.45 mL) and water (0.90 mL) at 0° C. was added 1,3-dichloro-5,5-dimethylimidazolidine-2,4-dione (0.40 g, 2.03 mmol, 3.0 equiv) and the reaction mixture was stirred at 0° C. After completion, the reaction was quenched with saturated sodium bicarbonate and extracted with DCM. The organic phase was dried over $Na_2SO_4$, filtered and concentrated and the residue was purified by normal phase chromatography. ESI+ MS $[M+H]^+$ $C_{22}H_{23}ClFN_3O_4S$: 480.1 found, 480.9 required.

6-fluoro-1-((1,2,3,4-tetrahydroisoquinolin-8-methyl)-N-1,2,4-thiadiazol-5-1H-indazole-5-sulfonamide (Ex-1)

To a solution of N-(2,4-dimethoxybenzyl)-1,2,4-thiadiazol-5-amine (0.10 g, 0.41 mmol, 1.1 equiv) in THF (0.93 mL) at −78° C. was added LIHMDS (0.41 mL, 0.41 mmol, 1.1 equiv) and the system was stirred for 0.5 h followed by the slow addition of tert-butyl 84(5-(chlorosulfonyl)-6-fluoro-1H-indazol-1-yl)methyl)-3,4-dihydroisoquinoline-2(1H)-carboxylate (1-4, 0.17 g, 0.37 mmol, 1.0 equiv) in THF (0.31 mL) and stirred overnight as the system approached ambient temperature. The reaction was quenched with ammonium chloride and extracted with EtOAc. The organic phase was dried over $Na_2SO_4$, filtered and concentrated and the residue was purified by normal phase chromatography. To this residue (0.05 g, 0.07 mmol, 1.0 equiv) in DCM (0.18 mL) at −78° C. was added trifluoroacetic acid (0.06 mL) and the reaction mixture was stirred at −78° C. for 1 h. The reaction was concentrated in vacuo and purified by reverse phase chromatography (10%→100% 0.1% TFA in ACN: 0.1% TFA in water) to afford compound of the invention Ex-1 as a mono TFA salt. $^1H$ NMR (400 MHz, $CDCl_3$) δ 9.15 (br s, 1H), 8.35-8.40 (m, 3H), 7.81 (d, J=8 Hz, 1H), 7.15-7.20 (m, 2H), 6.80-6.85 (m, 1H), 5.65 (s, 2H), 4.38 (s, 2H), 3.25 (t, 2H), 3.00 (t, 2H), 2.50 (s, 1H). HRMS [M+H] $C_{19}H_{17}FN_6O_2S_2$ calc'd 445.0911. found 445.0916.

Using the procedures illustrated in Scheme A, but substituting an appropriate DMB-aryl amine reagent, compounds of the Formula:

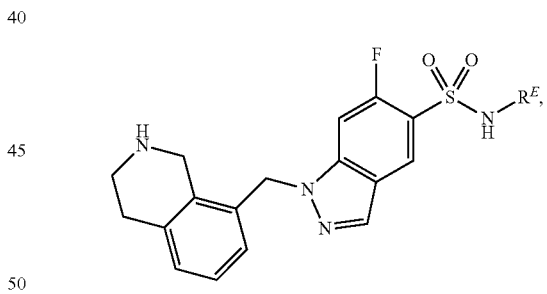

where $R^E$ is defined in Table I were prepared.

The necessary reagents are either available as articles of commerce or are readily synthesized using literature procedures from starting materials which are articles of commerce.

TABLE I

| Expl. No. | $R^E$ | Chemical Name | HRMS |
|---|---|---|---|
| Ex-2 | ![thiazol-2-yl] | 6-fluoro-1-((1,2,3,4-tetrahydroisoquinolin-8-yl)methyl)-N-(thiazol-2-yl)-1H-indazole-5-sulfonamide | C20H18FN5O2S2 [M + H] calc 444.0959 obs 444.0950 |

TABLE I-continued

| Expl. No. | R^E | Chemical Name | HRMS |
|---|---|---|---|
| Ex-3 | (5-chlorothiazol-2-yl) | N-(5-chlorothiazol-2-yl)-6-fluoro-1-((1,2,3,4-tetrahydroisoquinolin-8-yl)methyl)-1H-indazole-5-sulfonamide | $C_{20}H_{17}ClFN_5O_2S$ [M + H] calc 478.0569 obs 478.0558 |
| Ex-4 | (6-fluoropyridin-2-yl) | 6-fluoro-N-(6-fluoropyridin-2-yl)-1-((1,2,3,4-tetrahydroisoquinolin-8-yl)methyl)-1H-indazole-5-sulfonamide | $C_{22}H_{19}FN_5O_2S_2$ [M + H] calc 456.1300 obs 456.1302 |
| Ex-4b | (5-fluoropyridin-2-yl) | 6-fluoro-N-(5-fluoropyridin-2-yl)-1-(1,2,3,4-tetrahydroisoquinolin-8-ylmethyl)-1H-indazole-5-sulfonamide | $C_{22}H_{20}F_2N_5O_2S$ [M + H] Calc'd 456.1303, found 456.1296 |

Example 2

Preparation of (E)-1-(2-(3-aminoprop-1-en-1-yl)benzyl)-6-fluoro-N-(1,2,4-thiadiazol-5-yl)-1H-indazole-5-sulfonamide (Ex-5) from 5-(Benzylthio)-6-fluoro-1H-indazole The title compound was prepared in accordance with Scheme B.

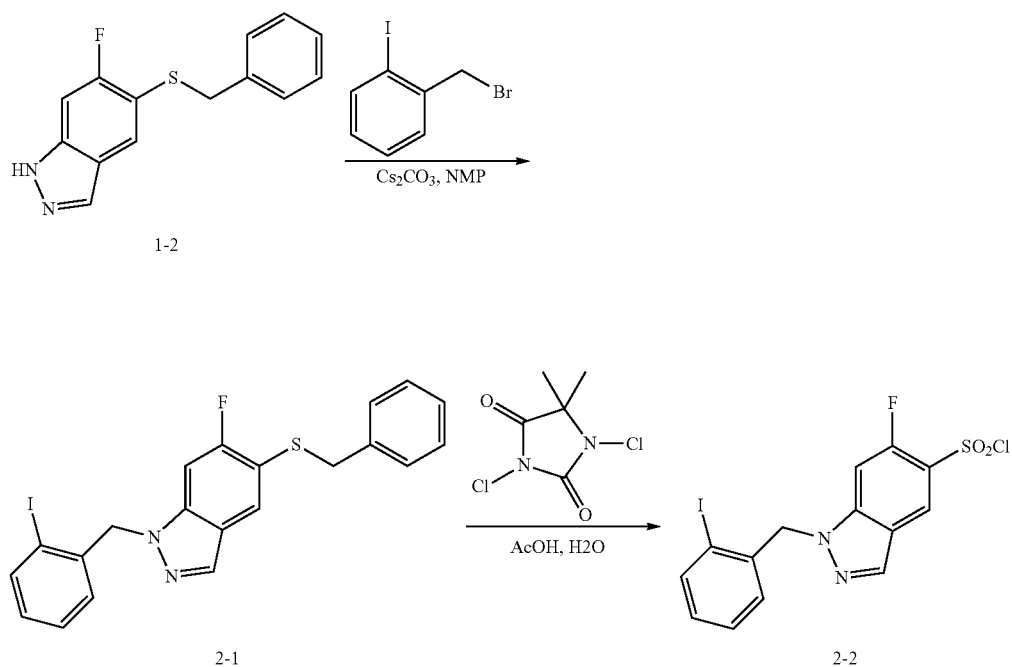

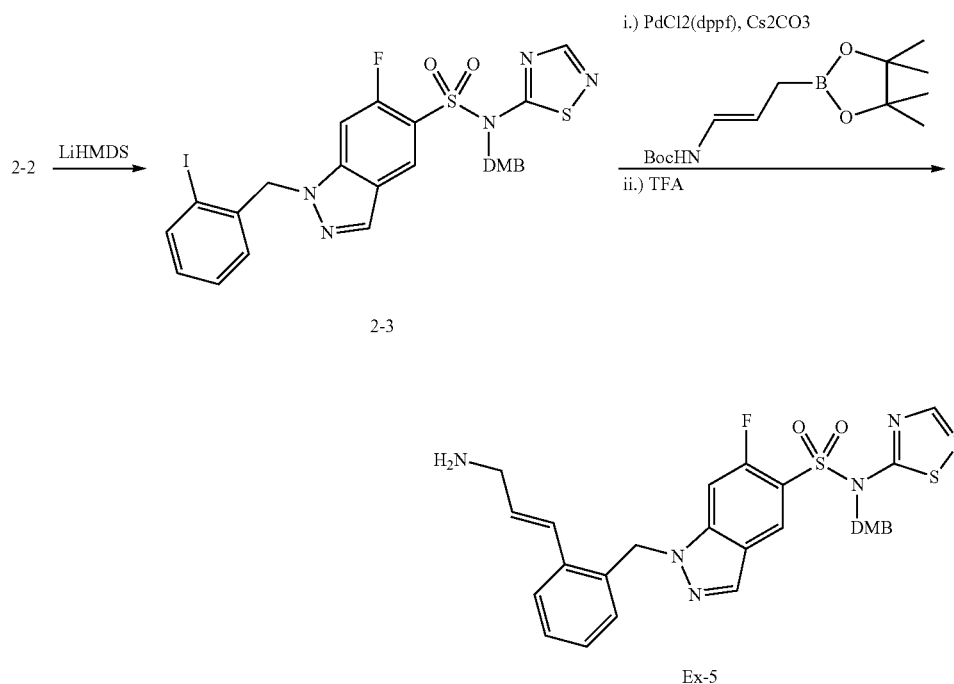

5-(benzylthio)-6-fluoro-1-(2-iodobenzyl)-1H-indazole (2-1)

To a solution of 5-(benzylthio)-6-fluoro-1H-indazole (1-2, 1.5 g, 5.81 mmol, 1.0 equiv) in NMP (29.0 mL) was added cesium carbonate (5.68 g, 17.42 mmol, 3.0 equiv) and 1-(bromomethyl)-2-iodobenzene (2.59 g, 8.71 mmol, 1.5 equiv) and the reaction mixture was stirred at ambient temperature. Upon completion, the reaction mixture was washed with water and extracted with EtOAc. The organic phase was dried over Na$_2$SO$_4$, filtered and concentrated and the residue was purified by normal phase chromatography followed by reverse phase chromatography (50%→100% 0.1% TFA in ACN: 0.1% TFA in water) to yield the desired regioisomer. ESI+ MS [M+H]$^+$ C$_{21}$H$_{16}$FIN$_2$S: 475.1 found, 475.3 required.

6-fluoro-1-(2-iodobenzyl)-1H-indazole-5-sulfonyl chloride (2-2)

To a solution of 5-(benzylthio)-6-fluoro-1-(2-iodobenzyl)-1H-indazole (2-1, 1.5 g, 3.16 mmol, 1.0 equiv) in ACN (14.76 mL), AcOH (2.10 mL) and water (4.22 mL) at −78° C. was added 1,3-dichloro-5,5-dimethylimidazolidine-2,4-dione (1.86 g, 9.49 mmol, 3.0 equiv). Upon completion, the reaction was quenched with saturated sodium bicarbonate and extracted with DCM. The organic phase was dried over Na$_2$SO$_4$, filtered and concentrated and the residue was purified by normal phase chromatography. ESI+ MS [M+H]$^+$ C$_{14}$H$_9$ClFIN$_2$O$_2$S: 451.0 found, 451.6 required.

N-(2,4-dimethoxybenzyl)-6-fluoro-1-(2-iodobenzyl)-N-(1,2,4-thiadiazol-5-yl)-1H-indazol-5-sulfonamide (2-3)

To a solution of N-(2,4-dimethoxybenzyl)-1,2,4-thiadiazol-5-amine (0.61 g, 2.44 mmol, 1.1 equiv) in THF (5.55 mL) at −78° C. was added LIHMDS (2.441 mL, 2.44 mmol, 1.1 equiv) and stirred for 0.5 h followed by the slow addition of 6-fluoro-1-(2-iodobenzyl)-1H-indazole-5-sulfonyl chloride (2-2, 1.0 g, 2.22 mmol, 1.0 equiv) in THF (1.85 mL) and stirred overnight as the system approached ambient temperature. The reaction was quenched with ammonium chloride and extracted with EtOAc. The organic phase was dried over Na$_2$SO$_4$, filtered and concentrated and the residue was purified by normal phase chromatography (0→40% EtOAc in hexanes). ESI+ MS [M+H]$^+$ C$_{25}$H$_{21}$FIN$_5$O$_4$S$_2$: 666.1 found, 666.5 required.

(E)-1-(2-(3-aminoprop-1-en-1-yl)benzyl)-6-fluoro-N-(1,2,4-thiadiazol-5-yl)-1H-indazol-5-sulfonamide (Ex-5)

To a solution of N-(2,4-dimethoxybenzyl)-6-fluoro-1-(2-iodobenzyl)-N-(1,2,4-thiadiazol-5-yl)-1H-indazole-5-sulfonamide (2-3, 0.068 g, 0.103 mmol, 1.0 equiv) in THF (0.94 mL) was added (E)-tert-butyl (3-(4,4,5,5-tetramethyl-1,3,2-dioxaborolan-2-yl)prop-1-en-1-yl)carbamate (0.088 g, 0.310 mmol, 3.0 equiv) and Pd(Cl)$_2$dppf (0.008 g, 10.34 µmol, 0.1 equiv) followed by 1M cesium carbonate (0.094 mL) and the system was irradiated at 120° C. for 10 min. The reaction contents were extracted with EtOAc and water and the organic phase was dried over Na$_2$SO$_4$, filtered and concentrated. To this residue was added DCM (0.69 mL) followed by TFA (0.17 mL) and the system was stirred at room temperature for 1 h. The reaction contents were then concentrated in vacuo and purified by reverse phase chromatography (10%→70% 0.1% TFA in ACN: 0.1% TFA in water) to yield compound Ex-5 as a mono TFA salt. $^1$H NMR (400 MHz, CDCl$_3$) δ 8.30-8.43 (m, 3H), 8.00 (br s, 2H), 7.80 (m, 1H), 7.50 (m, 1H), 7.18-7.39 (m, 3H), 6.80 (m, 1H), 6.20 (m, 1H), 5.70 (s, 2H), 2.45 (m, 3H). HRMS [M+H] C$_{19}$H$_{17}$FN$_6$O$_2$S$_2$ calc'd 445.0911. found 445.0910.

Example 3

Preparation of (R)-6-fluoro-1-(1-(1,2,3,4-tetrahydroisoquinolin-8-yl)ethyl)-N-(1,2,4-thiadiazol-5-yl)-1H-indazole-5-sulfonamide (Ex-6)

The title compound was prepared in accordance with Scheme A, below.

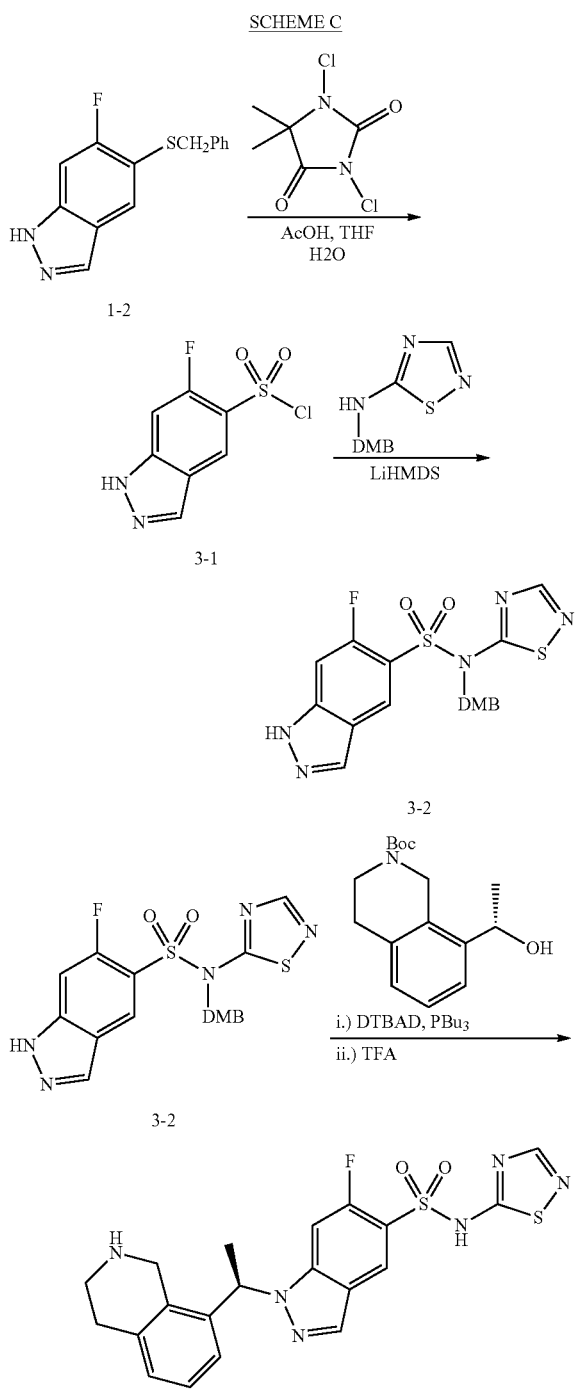

6-fluoro-1H-indazole-5-sulfonyl chloride (3-1)

To a solution of 5-(benzylthio)-6-fluoro-1H-indazole (1-2, 2.5 g, 9.68 mmol, 1.0 equiv) in THF (90 mL), AcOH (12.9 mL) and water (25.8 mL) at 0° C. was added 1,3-dichloro-5,5-dimethylimidazolidine-2,4-dione (5.72 g, 29.0 mmol, 3.0 equiv) and the reaction mixture was stirred at 0° C. The reaction was immediately quenched with saturated sodium bicarbonate and extracted with EtOAc. The organic phase was dried over $Na_2SO_4$, filtered and concentrated and the residue was purified by normal phase chromatography and used directly in the next step. ESI+ MS [M+H]$^+$ $C_7H_4ClFN_2O_2S$: 235.0 found, 235.6 required.

N-(2,4-dimethoxybenzyl)-6-fluoro-N-(1,2,4-thiadiazole-5-yl)-1H-indazole-5-sulfonamide (3-2)

To a solution of N-(2,4-dimethoxybenzyl)-1,2,4-thiadiazol-5-amine (1.6 g, 6.39 mmol, 1.5 equiv) in THF (32.0 mL) at −78° C. was added LHMDS (10.65 mL, 10.65 mmol, 2.5 equiv) and the system was stirred for 30 min followed by the slow addition of 6-fluoro-1H-indazole-5-sulfonyl chloride (1-4, 1.0 g, 4.26 mmol, 1.0 equiv) in THF (10.65 mL) and stirred overnight as the system approached ambient temperature. The reaction was quenched with ammonium chloride and extracted with EtOAc. The organic phase was dried over $Na_2SO_4$, filtered and concentrated and the residue was purified by normal phase chromatography and used directly in the next step.

6-fluoro-1-((1,2,3,4-tetrahydroisoquinolin-8-methyl)-N-(1,2,4-thiadiazol-5-1H-indazole-5-sulfonamide (Ex-6)

To a 100 mL RB flask containing THF (2.2 ml) at 0° C. was added sequentially N-(2,4-dimethoxybenzyl)-6-fluoro-N-(1,2,4-thiadiazol-5-yl)-1H-indazole-5-sulfonamide (0.10 mg, 0.22 mmol, 1.0 equiv), tri-n-butylphosphine (0.062 ml, 0.44 mmol, 2.0 equiv), di-tertbutylazodicarboxylate (0.102 g, 0.44 mmol, 2.0 equiv) and (S)-tert-butyl 8-(1-hydroxyethyl)-3,4-dihydroisoquinoline-2(1H)-carboxylate (0.123 g, 0.44 mmol, 2.0 equiv). After 1 h at 0° C., reaction was complete and was purified by normal-phase ISCO (40 g column, 0-40% EtOAc:Hex) to give a white solid. To this residue (75 mg, 0.106 mmol, 1.0 equiv) in DCM (1.69 mL) was added with trifluoroacetic acid (0.42 mL) and the reaction mixture was stirred at ambient temperature for 30 min. The reaction was concentrated in vacuo and purified by reverse phase chromatography (10%→60% 0.1% TFA in ACN: 0.1% TFA in water) to afford compound of the invention Ex-6 as a mono TFA salt. $^1$H NMR δ (ppm)(CH$_3$OH-d$_4$): 8.43 (1H, d, J=6.68 Hz), 8.27 (1H, s), 8.20 (1H, s), 7.35-7.21 (4H, m), 6.03 (1H, q, J=6.89 Hz), 4.40 (1H, d, J=15.78 Hz), 4.01 (1H, d, J=15.77 Hz), 3.48-3.38 (2H, m), 3.12 (2H, q, J=5.67 Hz), 1.96 (3H, d, J=6.88 Hz). HRMS [M+H] $C_{20}H_{19}FN_6O_2S_2$ calc'd 459.1068. found 459.1067.

Using the procedures illustrated in Scheme C, but substituting appropriate reagents, compounds of the Formula:

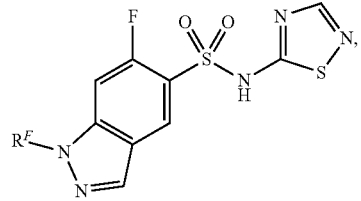

where R$^F$ is defined in Table II were prepared.

The necessary reagents are either available as articles of commerce or are readily synthesized using literature procedures from starting materials which are articles of commerce.

TABLE II

| Expl. No. | R^F | Chemical Name | HRMS |
|---|---|---|---|
| Ex-7 | 2-iodobenzyl group | 6-fluoro-1-(2-iodobenzyl)-N-1,2,4-thiadiazol-5-yl-1H-indazole-5-sulfonamide | C16H11FIN5O2S2 [M + H] calc 515.9419 obs 515.9444 |
| Ex-8 | N-[2-(dimethylamino)ethyl]biphenyl-3-carboxamide group | N-[2-(dimethylamino)ethyl]-2'-{[6-fluoro-5-(1,2,4-thiadiazol-5-ylsulfamoyl)-1H-indazol-1-yl]methyl}biphenyl-3-carboxamide | C27H26FN7O3S2 [M + H] calc 580.1597 obs 580.1580 |
| Ex-9 | (1R)-1-phenylethyl group | 6-fluoro-1-[(1R)-1-phenylethyl]-N-1,2,4-thiadiazol-5-yl-1H-indazole-5-sulfonamide | C17H14FN5O2S2 [M + H] calc 404.0649 obs 404.0654 |
| Ex-10 | 2-(1,2,3,4-tetrahydroisoquinolin-5-yl)benzyl group | 6-fluoro-1-[2-(1,2,3,4-tetrahydroisoquinolin-5-yl)benzyl]-N-1,2,4-thiadiazol-5-yl-1H-indazole-5-sulfonamide | C25H21FN6O2S2 [M + H] calc 521.1227 obs 521.1204 |
| Ex-11 | (1S)-1-phenylethyl group | 6-fluoro-1-[(1S)-1-phenylethyl]-N-1,2,4-thiadiazol-5-yl-1H-indazole-5-sulfonamide | C17H14FN5O2S2 [M + H] calc 404.0649 obs 404.0654 |
| Ex-64 | 1-(1,2,3,4-tetrahydroisoquinolin-8-yl)ethyl group | (S)-6-fluoro-1-(1-(1,2,3,4-tetrahydroisoquinolin-8-yl)ethyl)-N-(1,2,4-thiadiazol-5-yl)-1H-indazole-5-sulfonamide | C20H19FN6O2S2 [M + H] calc 459.1068 obs. 459.1067 |
| Ex-12 | benzyl group | 1-benzyl-6-fluoro-N-(1,2,4-thiadiazol-5-yl)-1H-indazole-5-sulfonamide | C16H12FN5O2S2 [M + H] calc 390.0489 obs 390.0481 |
| Ex-13A Isomer A (faster eluting) | (7-amino-5,6,7,8-tetrahydronaphthalen-1-yl)methyl group | (R or S)-1-((7-amino-5,6,7,8-tetrahydronaphthalen-1-yl)methyl)-6-fluoro-N-(1,2,4-thiadiazol-5-yl)-1H-indazole-5-sulfonamide | C20H19FN6O2S2 [[M + H] calc 459.1068 obs. 459.1057 |

TABLE II-continued

| Expl. No. | R$^F$ | Chemical Name | HRMS |
|---|---|---|---|
| Ex-13B Isomer B (slower eluting) | 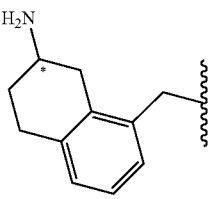 [SMILES: *Cc1cccc2c1CC(N)CC2] | (S or R)-1-((7-amino-5,6,7,8-tetrahydronaphthalen-1-yl)methyl)-6-fluoro-N-(1,2,4-thiadiazol-5-yl)-1H-indazole-5-sulfonamide | C20H19FN6O2S2 [M + H] calc 459.1068 obs. 459.1061 |

Using the procedures illustrated in Examples 1 and 2, but substituting appropriate reagents, compounds of the Formula:

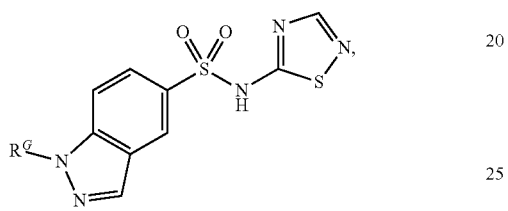

where R$^G$ is defined in Table III were prepared.

The necessary reagents are either available as articles of commerce or are readily synthesized using literature procedures from starting materials which are articles of commerce.

TABLE III

| Example | Structure | Chemical Name | HRMS/LRMS |
|---|---|---|---|
| Ex-15 | 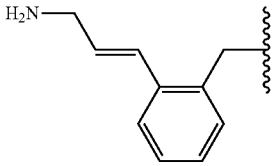 [SMILES: *Cc1ccccc1/C=C/CN] | 1-{2-[(1E)-3-aminoprop-1-en-1-yl]benzyl}-N-1,2,4-thiadiazol-5-yl-1H-indazole-5-sulfonamide | C19H18N6O2S2 [M + H] calc 427.1008 obs 427.1007 |
| Ex-16 | 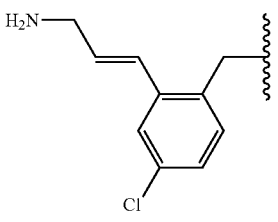 [SMILES: *Cc1ccc(Cl)cc1/C=C/CN] | 1-{2-[(1E)-3-aminoprop-1-en-1-yl]-4-chlorobenzyl}-N-1,2,4-thiadiazol-5-yl-1H-indazole-5-sulfonamide | C19H17ClN6O2S2 [M + H] calc 461.0619 obs 461.0603 |
| Ex-17 | 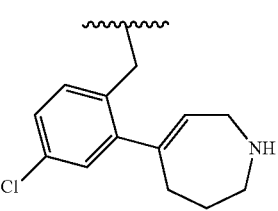 [SMILES: *Cc1ccc(Cl)cc1C1=CCNCCC1] | 1-[4-chloro-2-(2,5,6,7-tetrahydro-1H-azepin-4-yl)benzyl]-N-1,2,4-thiadiazol-5-yl-1H-indazole-5-sulfonamide | C22H21ClN6O2S2 [M + H] calc 501.0932 obs 501.0938 |

TABLE III-continued

| Example | Chemical Name | HRMS/LRMS |
|---|---|---|
| Ex-18 | 1-[4-chloro-2-(1,2,3,6-tetrahydropyridin-4-yl)benzyl]-N-1,2,4-thiadiazol-5-yl-1H-indazole-5-sulfonamide | C21H19ClN6O2S2 [M + H] calc 487.0775 obs 487.0784 |
| Ex-19 | 1-benzyl-N-1,2,4-thiadiazol-5-yl-1H-indazole-5-sulfonamide | C16H13N5O2S2 [M + H] calc 372.0587 obs 372.0595 |
| Ex-20 | 5'-chloro-N-[2-(dimethylamino)ethyl]-2'-{[5-(1,2,4-thiadiazol-5-ylsulfamoyl)-1H-indazol-1-yl]methyl}biphenyl-3-carboxamide | C27H26ClN7O3S2 [M + H] calc 596.1302 obs 596.1278 |
| Ex-21 | 1-[2-(8-azabicyclo[3.2.1]oct-2-en-3-yl)-4-chlorobenzyl]-N-1,2,4-thiadiazol-5-yl-1H-indazole-5-sulfonamide | C23H21ClN6O2S2 [M + H] calc 513.0932 obs 513.0931 |
| Ex-22 | 1-[2-(1,2,3,4-tetrahydroisoquinolin-5-yl)benzyl]-N-1,2,4-thiadiazol-5-yl-1H-indazole-5-sulfonamide | C25H22N6O2S2 [M + H] calc 503.1321 obs 503.1307 |
| Ex-23 | 1-[2-(2,5,6,7-tetrahydro-1H-azepin-4-yl)benzyl]-N-1,2,4-thiadiazol-5-yl-1H-indazole-5-sulfonamide | C22H22N6O2S2 [M + H] calc 467.1321 obs 467.1301 |
| Ex-24 | 1-[4-chloro-2-(1,2,3,4-tetrahydroisoquinolin-8-yl)benzyl]-N-1,2,4-thiadiazol-5-yl-1H-indazole-5-sulfonamide | C25H21ClN6O2S2 [M + H] calc 537.0931 obs 537.0938 |

TABLE III-continued

| Example | Structure | Chemical Name | HRMS/LRMS |
|---|---|---|---|
| Ex-25 | 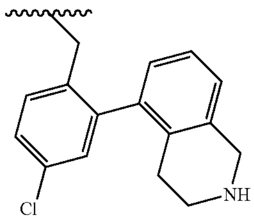 [SMILES: *Cc1ccc(Cl)cc1-c1cccc2c1CCNC2] | 1-[4-chloro-2-(1,2,3,4-tetrahydroisoquinolin-5-yl)benzyl]-N-1,2,4-thiadiazol-5-yl-1H-indazole-5-sulfonamide | C25H21ClN6O2S2 [M + H] calc 537.0931 obs 537.0905 |

Using the procedures illustrated in Scheme C, but substituting appropriate reagents, compounds of the Formula:

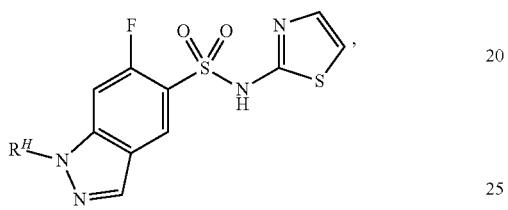

where $R^H$ is defined in Table IV were prepared.

The necessary reagents are either available as articles of commerce or are readily synthesized using literature procedures from starting materials which are articles of commerce.

TABLE IV

| Example | Structure | Chemical Name | HRMS |
|---|---|---|---|
| Ex-26 | 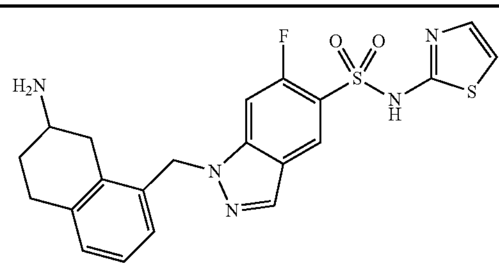 | (R or S)-1-[(7-amino-5,6,7,8-tetrahydronaphthalen-1-yl)methyl]-6-fluoro-N-1,3-thiazol-2-yl-1H-indazole-5-sulfonamide | Calc'd 458.1118, found 458.1102 |
| Ex-27 | 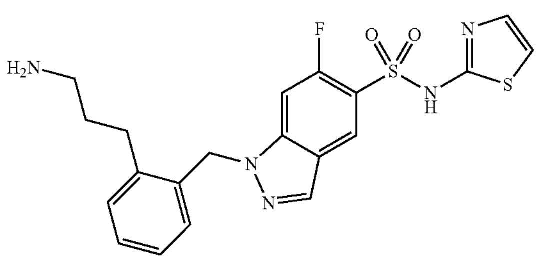 [SMILES: NCCCc1ccccc1Cn1ncc2cc(S(=O)(=O)Nc3nccs3)c(F)cc21] | 1-[2-(3-aminopropyl)benzyl]-6-fluoro-N-1,3-thiazol-2-yl-1H-indazole-5-sulfonamide | Calc'd 446.1118, found 446.1104 |
| Ex-28 | 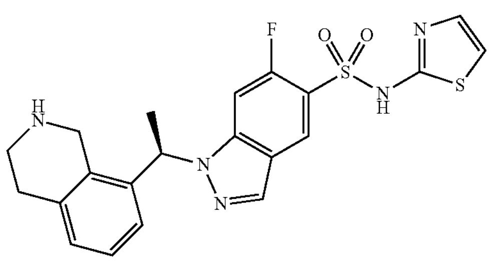 [SMILES: C[C@H](c1cccc2c1CNCC2)n1ncc2cc(S(=O)(=O)Nc3nccs3)c(F)cc21] | 6-fluoro-1-[(1R)-1-(1,2,3,4-tetrahydroisoquinolin-8-yl)ethyl]-N-1,3-thiazol-2-yl-1H-indazole-5-sulfonamide | Calc'd 458.1118, found 458.1104 |

TABLE IV-continued

| Example | Structure | Chemical Name | HRMS |
|---|---|---|---|
| Ex-29 | 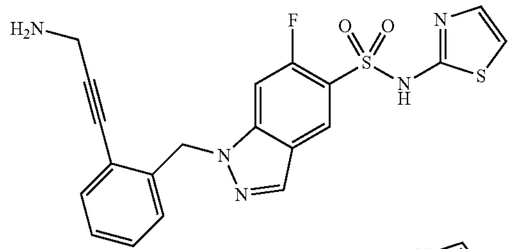 [SMILES: NCC#Cc1ccccc1Cn1ncc2cc(S(=O)(=O)Nc3nccs3)c(F)cc21] | 1-[2-(3-aminoprop-1-yn-1-yl)benzyl]-6-fluoro-N-1,3-thiazol-2-yl-1H-indazole-5-sulfonamide | Calc'd 442.0806, found 442.0791 |
| Ex-30 | 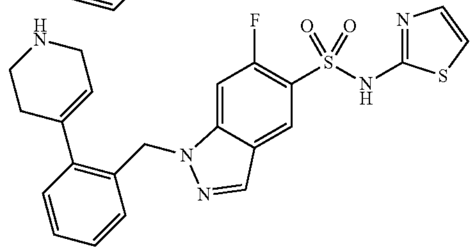 | 6-fluoro-1-[2-(1,2,3,6-tetrahydropyridin-4-yl)benzyl]-N-1,3-thiazol-2-yl-1H-indazole-5-sulfonamide | Calc'd 470.1118, found 470.1110 |

Using the procedures illustrated in Scheme C, but substituting appropriate reagents, compounds of the following formula were prepared, where $R^I$'s defined in Table V:

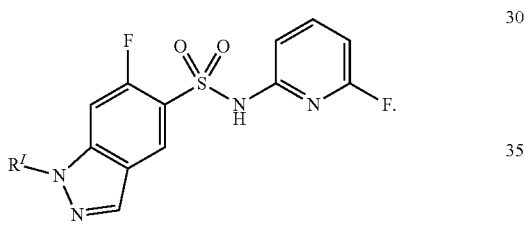

The necessary reagents are either available as articles of commerce or are readily synthesized using literature procedures from starting materials which are articles of commerce.

TABLE V

| Example | Structure | Chemical Name | HRMS/LRMS |
|---|---|---|---|
| Ex-31A Isomer A (faster eluting) | 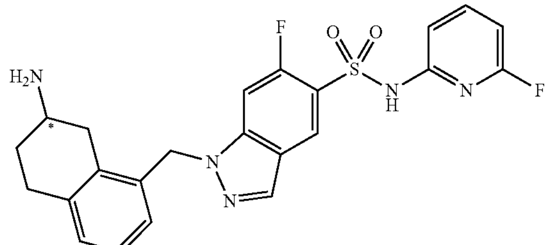 | (R or S)-1-[(7-amino-5,6,7,8-tetrahydronaphthalen-1-yl)methyl]-6-fluoro-N-(6-fluoropyridin-2-yl)-1H-indazole-5-sulfonamide | Calc'd 470.1460, found 470.1452 |
| Ex-31B Isomer B (slower eluting) | 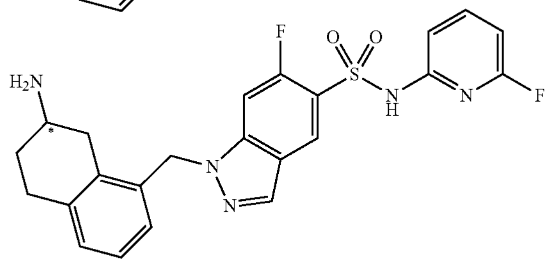 | (S or R)-1-[(7-amino-5,6,7,8-tetrahydronaphthalen-1-yl)methyl]-6-fluoro-N-(6-fluoropyridin-2-yl)-1H-indazole-5-sulfonamide | Calc'd 470.146, found 470.1448 |

TABLE V-continued

| Example | Structure | Chemical Name | HRMS/LRMS |
|---|---|---|---|
| Ex-32 | 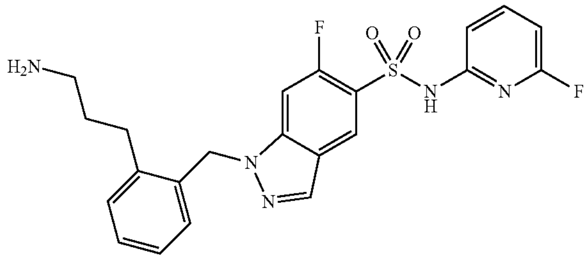 [SMILES: NCCCc1ccccc1Cn1ncc2cc(S(=O)(=O)Nc3cccc(F)n3)c(F)cc21] | 1-[2-(3-amino-propyl)benzyl]-6-fluoro-N-(6-fluoropyridin-2-yl)-1H-indazole-5-sulfonamide | Calc'd 458.146, found 458.1444 |
| Ex-33 | 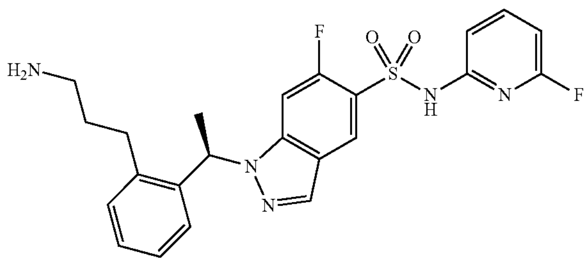 [SMILES: C[C@H](c1ccccc1CCCN)n1ncc2cc(S(=O)(=O)Nc3cccc(F)n3)c(F)cc21] | 1-{(1R)-1-[2-(3-amino-propyl)phenyl]ethyl}-6-fluoro-N-(6-fluoropyridin-2-yl)-1H-indazole-5-sulfonamide | Calc'd 472.1616, found 472.1594 |
| Ex-35 | 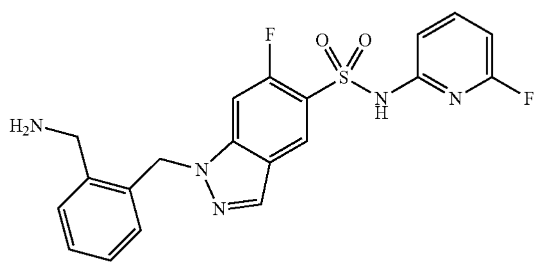 [SMILES: NCc1ccccc1Cn1ncc2cc(S(=O)(=O)Nc3cccc(F)n3)c(F)cc21] | 1-[2-(aminomethyl)benzyl]-6-fluoro-N-(6-fluoropyridin-2-yl)-1H-indazole-5-sulfonamide | Calc'd 430.1147, found 430.1140 |
| Ex-36 | 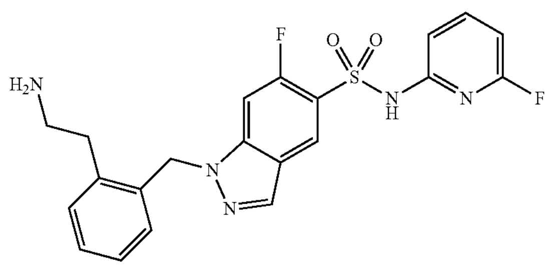 [SMILES: NCCc1ccccc1Cn1ncc2cc(S(=O)(=O)Nc3cccc(F)n3)c(F)cc21] | 1-[2-(2-aminoethyl)benzyl]-6-fluoro-N-(6-fluoropyridin-2-yl)-1H-indazole-5-sulfonamide | Calc'd 444.1 found 444.1 |
| Ex-37 | 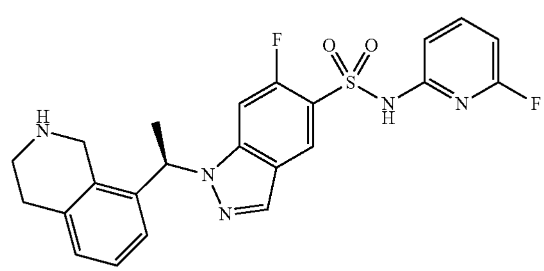 [SMILES: C[C@H](c1cccc2c1CNCC2)n1ncc2cc(S(=O)(=O)Nc3cccc(F)n3)c(F)cc21] | 6-fluoro-N-(6-fluoropyridin-2-yl)-1-[(1R)-1-(1,2,3,4-tetrahydroisoquinolin-8-yl)ethyl]-1H-indazole-5-sulfonamide | Calc'd 470.146, found 470.1451 |
| Ex-38 | 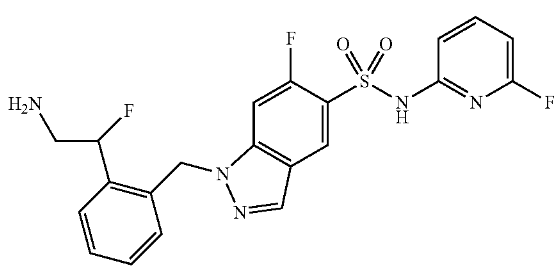 [SMILES: NCC(F)c1ccccc1Cn1ncc2cc(S(=O)(=O)Nc3cccc(F)n3)c(F)cc21] | 1-[2-(2-amino-1-fluoroethyl)benzyl]-6-fluoro-N-(6-fluoropyridin-2-yl)-1H-indazole-5-sulfonamide | Calc'd 462.1206, found 462.1199 |

TABLE V-continued

| Example | Structure | Chemical Name | HRMS/LRMS |
|---|---|---|---|
| Ex-39 | 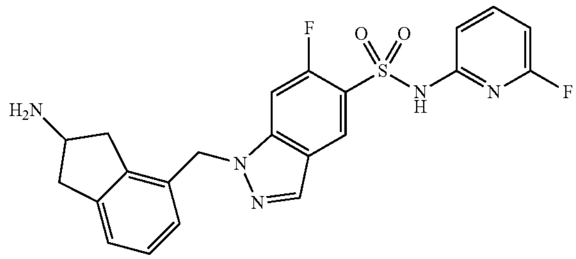 [SMILES: NC1Cc2cccc(Cn3ncc4cc(S(=O)(=O)Nc5cccc(F)n5)c(F)cc43)c2C1] | 1-[(2-amino-2,3-dihydro-1H-inden-4-yl)methyl]-6-fluoro-N-(6-fluoropyridin-2-yl)-1H-indazole-5-sulfonamide | Calc'd 456.1300, found 456.1302 |
| Ex-40 | 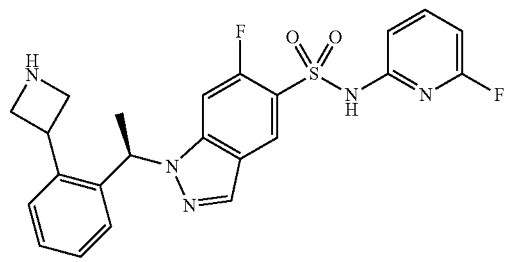 [SMILES: C[C@H](c1ccccc1C1CNC1)n1ncc2cc(S(=O)(=O)Nc3cccc(F)n3)c(F)cc21] | 1-[(1R)-1-(2-azetidin-3-ylphenyl)ethyl]-6-fluoro-N-(6-fluoropyridin-2-yl)-1H-indazole-5-sulfonamide | Calc'd 470.146, found 470.1451 |
| Ex-41 | 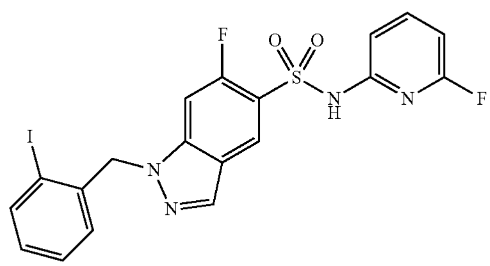 [SMILES: O=S(=O)(Nc1cccc(F)n1)c1cc2cnn(Cc3ccccc3I)c2cc1F] | 6-fluoro-N-(6-fluoropyridin-2-yl)-1-(2-iodobenzyl)-1H-indazole-5-sulfonamide | Calc'd 526.9808, found 526.9827 |
| Ex-42 | 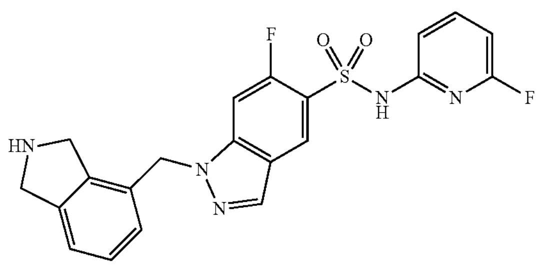 [SMILES: O=S(=O)(Nc1cccc(F)n1)c1cc2cnn(Cc3cccc4c3CNC4)c2cc1F] | 1-(2,3-dihydro-1H-isoindol-4-ylmethyl)-6-fluoro-N-(6-fluoropyridin-2-yl)-1H-indazole-5-sulfonamide | Calc'd 442.1144, found 442.1142 |
| Ex-43 | 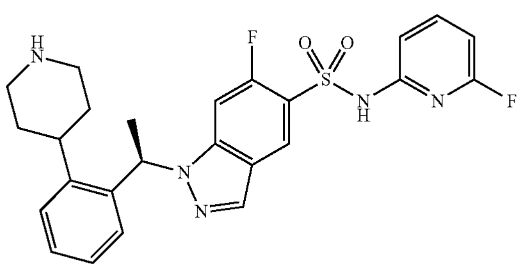 [SMILES: C[C@H](c1ccccc1C1CCNCC1)n1ncc2cc(S(=O)(=O)Nc3cccc(F)n3)c(F)cc21] | 6-fluoro-N-(6-fluoropyridin-2-yl)-1-[(1R)-1-(2-piperidin-4-ylphenyl)ethyl]-1H-indazole-5-sulfonamide | Calc'd 498.1772, found 498.1766 |
| Ex-44 | 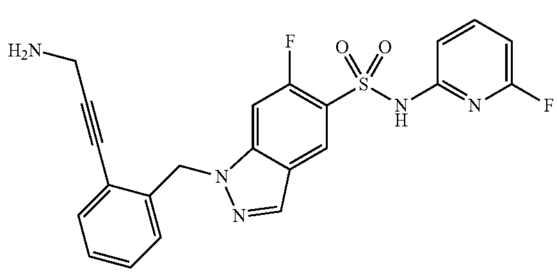 [SMILES: NCC#Cc1ccccc1Cn1ncc2cc(S(=O)(=O)Nc3cccc(F)n3)c(F)cc21] | 1-[2-(3-aminoprop-1-yn-1-yl)benzyl]-6-fluoro-N-(6-fluoropyridin-2-yl)-1H-indazole-5-sulfonamide | Calc'd 454.1 found 454.1 |

TABLE V-continued

| Example | Structure | Chemical Name | HRMS/LRMS |
|---|---|---|---|
| Ex-45 | 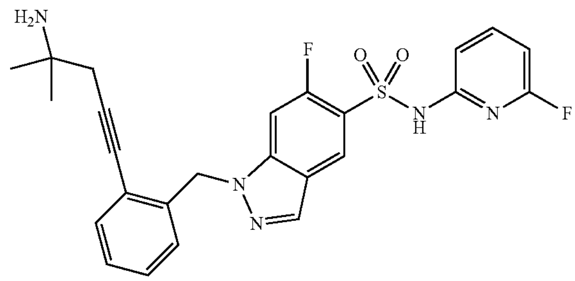 [SMILES: CC(C)(N)CC#Cc1ccccc1Cn1ncc2cc(S(=O)(=O)Nc3cccc(F)n3)c(F)cc21] | 1-[2-(4-amino-4-methylpent-1-yn-1-yl)benzyl]-6-fluoro-N-(6-fluoropyridin-2-yl)-1H-indazole-5-sulfonamide | Calc'd 496.1616, found 496.1597 |
| Ex-46 | 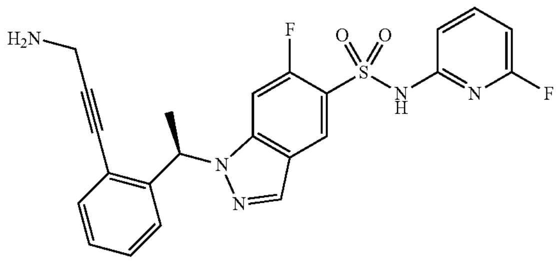 [SMILES: C[C@H](c1ccccc1C#CCN)n1ncc2cc(S(=O)(=O)Nc3cccc(F)n3)c(F)cc21] | 1-{(1R)-1-[2-(3-aminoprop-1-yn-1-yl)phenyl]ethyl}-6-fluoro-N-(6-fluoropyridin-2-yl)-1H-indazole-5-sulfonamide | Calc'd 468.1303, found 468.1288 |
| Ex-47 | 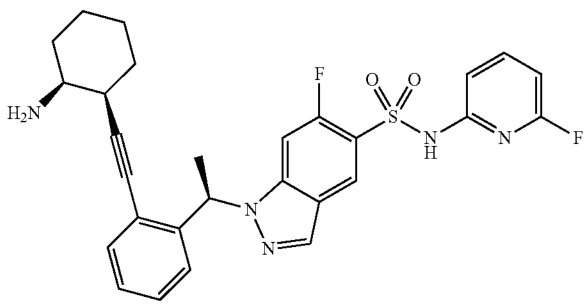 [SMILES: C[C@H](c1ccccc1C#C[C@@H]1CCCC[C@@H]1N)n1ncc2cc(S(=O)(=O)Nc3cccc(F)n3)c(F)cc21] | 1-[(1R)-1-(2-{[(1S,2S)-2-amino-cyclohexyl]ethynyl}phenyl)ethyl]-6-fluoro-N-(6-fluoropyridin-2-yl)-1H-indazole-5-sulfonamide | Calc'd 536.1929, found 536.1903 |
| Ex-48 | 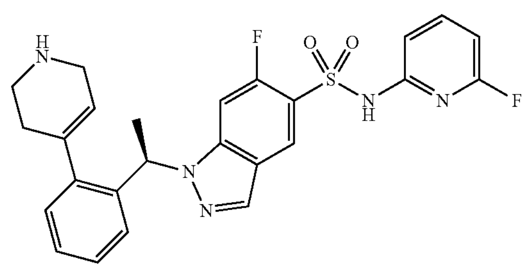 [SMILES: C[C@H](c1ccccc1C1=CCNCC1)n1ncc2cc(S(=O)(=O)Nc3cccc(F)n3)c(F)cc21] | 6-fluoro-N-(6-fluoropyridin-2-yl)-1-{(1R)-1-[2-(1,2,3,6-tetrahydropyridin-4-yl)phenyl]ethyl}-1H-indazole-5-sulfonamide | Calc'd 496.1616, found 496.1609 |
| Ex-49 | 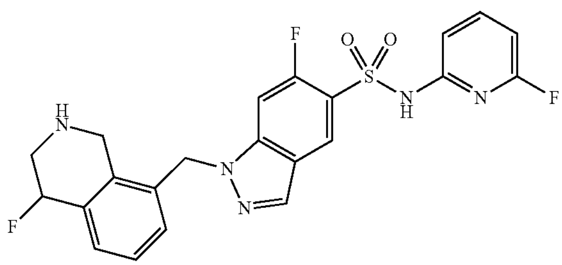 [SMILES: O=S(=O)(Nc1cccc(F)n1)c1cc2cnn(Cc3cccc4c3CNCC4F)c2cc1F] | 6-fluoro-N-(6-fluoropyridin-2-yl)-1-[(4-fluoro-1,2,3,4-tetrahydro-isoquinolin-8-yl)methyl]-1H-indazole-5-sulfonamide | Calc'd 474.1206, found 474.1197 |

TABLE V-continued

| Example | Structure | Chemical Name | HRMS/LRMS |
|---|---|---|---|
| Ex-50 | 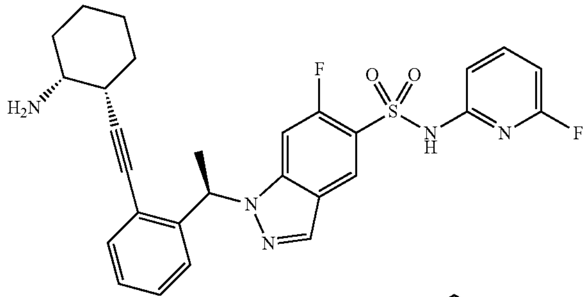 [SMILES: C[C@H](c1ccccc1C#C[C@H]1CCCC[C@H]1N)n1ncc2cc(S(=O)(=O)Nc3cccc(F)n3)c(F)cc21] | 1-[(1R)-1-(2-{[(1R,2R)-2-amino-cyclohexyl]ethynyl}phenyl)ethyl]-6-fluoro-N-(6-fluoropyridin-2-yl)-1H-indazole-5-sulfonamide | Calc'd 536.1929, found 536.1910 |
| Ex-51 | 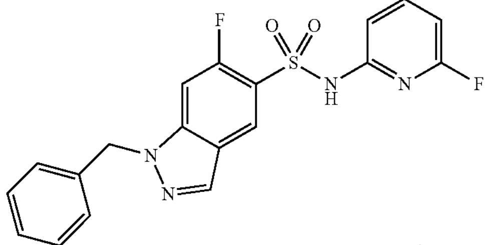 [SMILES: O=S(=O)(Nc1cccc(F)n1)c1cc2cnn(Cc3ccccc3)c2cc1F] | 1-benzyl-6-fluoro-N-(6-fluoropyridin-2-yl)-1H-indazole-5-sulfonamide | Calc'd 401.0882, found 401.0869 |
| Ex-52 | 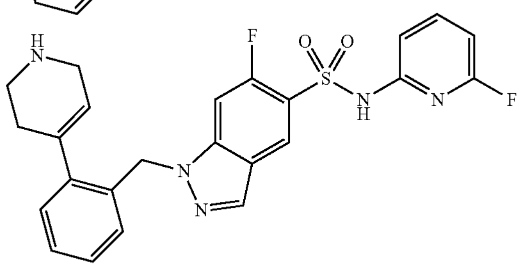 | 6-fluoro-N-(6-fluoropyridin-2-yl)-1-[2-(1,2,3,6-tetrahydropyridin-4-yl)benzyl]-1H-indazole-5-sulfonamide | Calc'd 482.146, found 482.1437 |

Using the procedures illustrated in Scheme C, but substituting appropriate reagents, compounds of the Formula:

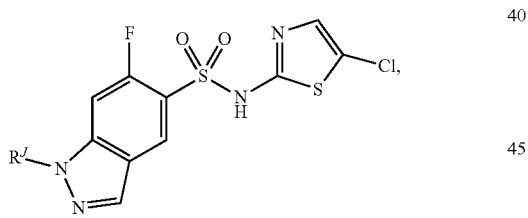

where $R^J$ is defined in Table VI were prepared.

The necessary reagents are either available as articles of commerce or are readily synthesized using literature procedures from starting materials which are articles of commerce.

TABLE VI

| Example | Structure | Chemical Name | HRMS |
|---|---|---|---|
| Ex-53 | 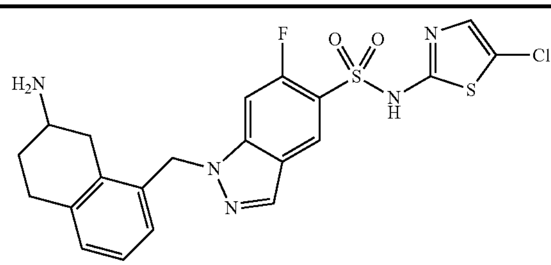 | 1-[(7-amino-5,6,7,8-tetrahydronaphthalen-1-yl)methyl]-N-(5-chloro-1,3-thiazol-2-yl)-6-fluoro-1H-indazole-5-sulfonamide | Calc'd 492.0728, found 492.0723 |

TABLE VI-continued

| Example | Structure | Chemical Name | HRMS |
|---------|-----------|---------------|------|
| Ex-54 | 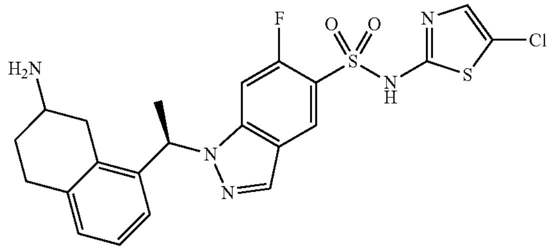 [SMILES: C[C@H](c1cccc2c1CC(N)CC2)n1ncc2cc(S(=O)(=O)Nc3ncc(Cl)s3)c(F)cc21] | N-(5-chloro-1,3-thiazol-2-yl)-6-fluoro-1-[(1R)-1-(1,2,3,4-tetrahydroisoquinolin-8-yl)ethyl]-1H-indazole-5-sulfonamide | Calc'd 492.0728, found 492.0726 |
| Ex-55 | 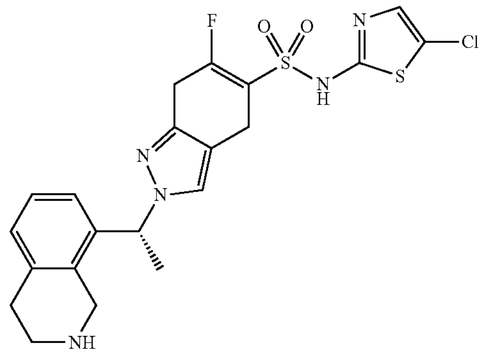 [SMILES: C[C@H](c1cccc2c1CNCC2)n1cc2c(n1)CC(F)=C(S(=O)(=O)Nc1ncc(Cl)s1)C2] | N-(5-chloro-1,3-thiazol-2-yl)-6-fluoro-2-[(1R)-1-(1,2,3,4-tetrahydroisoquinolin-8-yl)ethyl]-2H-indazole-5-sulfonamide | Calc'd 492.0728, found 492.0720 |
| Ex-56 | 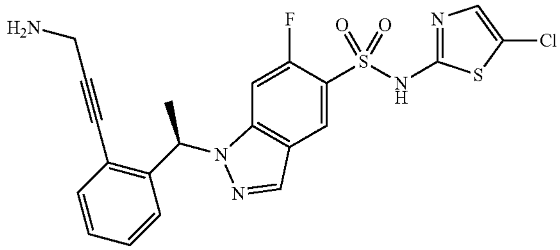 [SMILES: C[C@H](c1ccccc1C#CCN)n1ncc2cc(S(=O)(=O)Nc3ncc(Cl)s3)c(F)cc21] | 1-{(1R)-1-[2-(3-aminoprop-1-yn-1-yl)phenyl]ethyl}-N-(5-chloro-1,3-thiazol-2-yl)-6-fluoro-1H-indazole-5-sulfonamide | Calc'd 490.0572, found 490.0576 |
| Ex-57 | 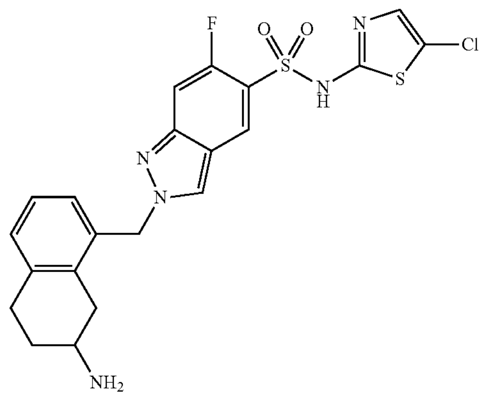 [SMILES: NC1CCc2cccc(Cn3cc4cc(S(=O)(=O)Nc5ncc(Cl)s5)c(F)cc4n3)c2C1] | 2-[(7-amino-5,6,7,8-tetrahydronaphthalen-1-yl)methyl]-N-(5-chloro-1,3-thiazol-2-yl)-6-fluoro-2H-indazole-5-sulfonamide | Calc'd 492.0728, found 492.0722 |

Using the procedures illustrated in Scheme C, but substituting appropriate reagents, compounds of the following formula were prepared, where $R^K$ is defined in Table VII:

The necessary reagents are either available as articles of commerce or are readily synthesized using literature procedures from starting materials which are articles of commerce.

TABLE VII

| Example | Structure | Chemical Name | HRMS |
|---|---|---|---|
| Ex-58 | 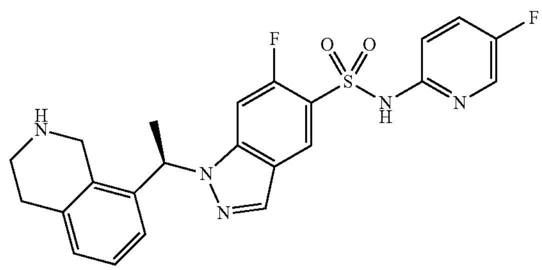 [SMILES: C[C@H](c1cccc2c1CNCC2)n1ncc2cc(S(=O)(=O)Nc3ccc(F)cn3)c(F)cc21] | 6-fluoro-N-(5-fluoropyridin-2-yl)-1-[(1R)-1-(1,2,3,4-tetrahydroiso-quinolin-8-yl)ethyl]-1H-indazole-5-sulfonamide | Calc'd 470.146, found 470.1448 |
| Ex-59 | 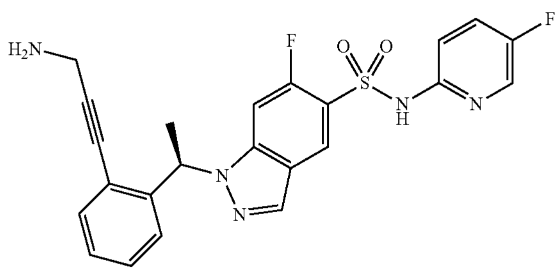 [SMILES: C[C@H](c1ccccc1C#CCN)n1ncc2cc(S(=O)(=O)Nc3ccc(F)cn3)c(F)cc21] | 1-{(1R)-1-[2-(3-aminoprop-1-yn-1-yl)phenyl]ethyl}-6-fluoro-N-(5-fluoropyridin-2-yl)-1H-indazole-5-sulfonamide | Calc'd 468.1303, found 468.1286 |

Example 4

Preparation of N-(6-fluoropyridin-2-yl)-6-methyl-1-[(1R)-1-(1,2,3,4-tetrahydroisoquinolin-8-yl)ethyl]-1H-indazole-5-sulfonamide (Ex-60)

The title compound was prepared in accordance with Scheme D, below.

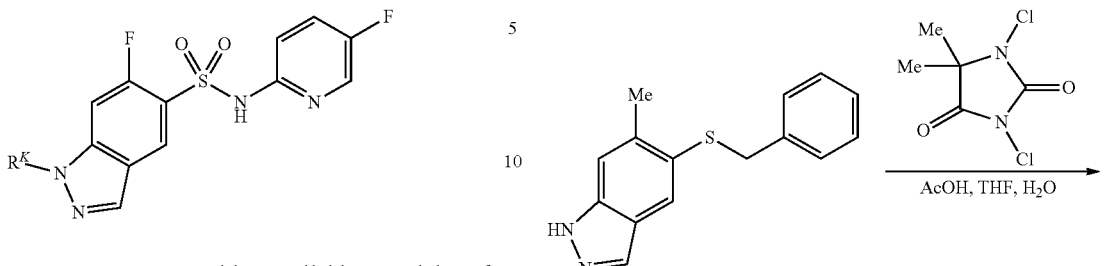

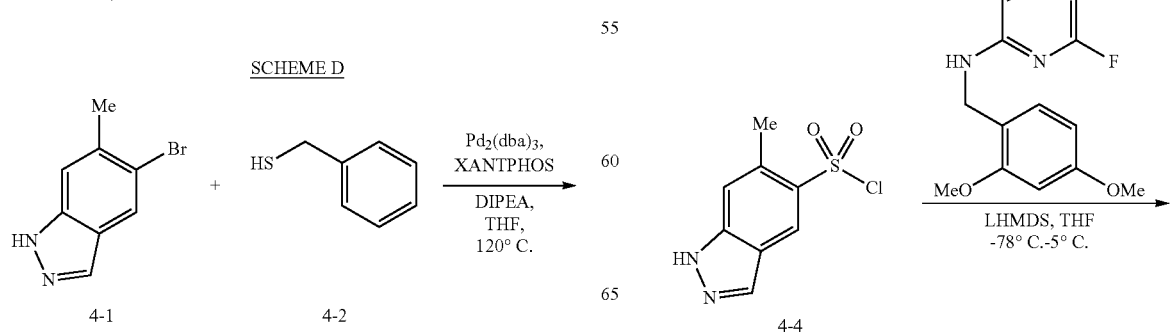

-continued

-continued

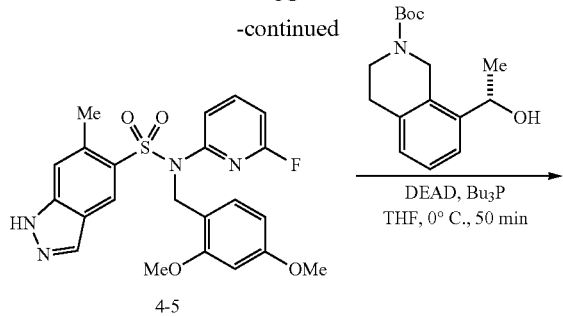

4-5

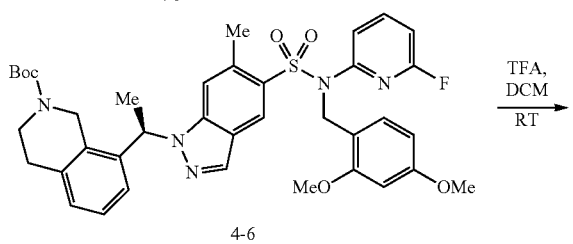

4-6

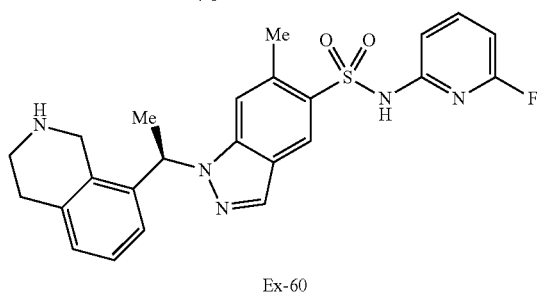

Ex-60

5-(Benzylsulfanyl)-6-methyl-1H-indazole (4-3)

5-Bromo-6-methyl-1H-indazole (4-1, 2 g, 9.48 mmol), XANTPHOS (0.548 g, 0.948 mmol), and Pd2(dba)3 (0.868 g, 0.948 mmol) were added to an oven-dried sealed tube followed by anhydrous Dioxane (31.6 ml), DIPEA (3.31 ml, 18.95 mmol) and BENZYL MERCAPTAN (1.177 ml, 9.95 mmol). Placed in 120° C. bath. After 2 h, UPLC showed >52% P1 at 1.25 min, 15% R1 at 1.07 min, 16% byproduct at 1.56 min and several minor peaks each less than 7%. After an additional 2 h, UPLC showed no change. Cooled to RT, filtered through Celite, washed with EtOAc, concentrated to give a clear, orange oil. Dissolved in 5 mL DCM, purified by normal-phase ISCO (80 g column, 0-50% EtOAc:Hex) to give 4-3 as a yellow solid.

6-Methyl-1H-indazole-5-sulfonyl chloride (4-4)

Added 5-(benzylthio)-6-methyl-1H-indazole (4-3, 1 g, 3.93 mmol) to THF (36.7 ml). Added Acetic Acid (5.24 ml) and Water (10.48 ml) and cooled to 0° C. Added 1.3 dichloro 5.5 hydantoin (2.324 g, 11.79 mmol). Immediately after reaction became homogenous (~10 sec), added to a mixture of 70 mL saturated NaHCO$_3$+70 mL EtOAc. Separated layers, pH of aqueous=7. Back-extracted aqueous with 2×20 mL EtOAc, dried over Na$_2$SO$_4$, filtered, concentrated to give a pale yellow solid. Suspended solid in DCM, filtered through Buchner funnel. Washed with DCM to afford 4-4 as a white solid.

N-(2,4-dimethoxybenzyl)-N-(6-fluoropyridin-2-yl)-6-methyl-1H-indazole-5-sulfonamide (4-5)

Added N-(2,4-dimethoxybenzyl)-6-fluoropyridin-2-amine (1.0 g, 3.87 mmol) to THF (19 mL) and cooled to −78° C. Added LHMDS (6.5 mL, 6.45 mmol), warmed to RT, stirred for 30 min, and cooled back to −78° C. Following addition of LHMDS, solution turned clear and pink in color. After warming to RT, solution became clear, yellow. At −78° C., added 6-methyl-1H-indazole-5-sulfonyl chloride (4-4, 594.8 mg, 2.58 mmol) in THF (6.5 mL) at −78° C. via syringe followed by THF rinse. Solution remained yellow in color. Allowed reaction flask to remain in bath and gradually warm to RT overnight. Following this duration, quenched with 40 mL saturated NH$_4$Cl, diluted with 20 mL EtOAc. Separated layers, back-extracted aqueous with 3×10 mL EtOAc. Dried organics over Na$_2$SO$_4$, filtered, concentrated to give an orange oil. Purified by normal-phase ISCO (40 g column, 0-50% EtOAc:Hex) to give 4-5 as a white solid.

tert-Butyl 8-[(1R)-1-{5-[(2,4-dimethoxybenzyl)(6-fluoropyridin-2-yl)sulfamoyl]-6-methyl-1H-indazol-1-yl}ethyl]-3,4-dihydroisoquinoline-2(1H)-carboxylate (4-6)

To a 100 mL RB flask containing THF (4381 µl) at 0° C. was added sequentially N-(2,4-dimethoxybenzyl)-N-(6-fluoropyridin-2-yl)-6-methyl-1H-indazole-5-sulfonamide (4-5, 200 mg, 0.438 mmol), TRI-N-BUTYLPHOSPHINE (216 µl, 0.876 mmol), DTBAD (202 mg, 0.876 mmol) and (S)-tert-butyl 8-(1-hydroxyethyl)-3,4-dihydroisoquinoline-2(1H)-carboxylate (243 mg, 0.876 mmol). After 50 min at 0° C., concentrated in vacuo. Purified by normal-phase ISCO (40 g column, 0-40% EtOAc:Hex) to give an off-white solid

N-(6-fluoropyridin-2-yl)-6-methyl-1-[(1R)-1-(1,2,3,4-tetrahydroisoquinolin-8-yl)ethyl]-1H-indazole-5-sulfonamide (Ex-60)

In a 1 dram vial, added (R)-tert-butyl 8-(1-(5-(N-(2,4-dimethoxybenzyl)-N-(6-fluoropyridin-2-yl)sulfamoyl)-6-methyl-1H-indazol-1-yl)ethyl)-3,4-dihydroisoquinoline-2 (1H)-carboxylate (4-6, 256 mg, 0.358 mmol) to DCM (1431 µl) and TFA (358 µl). After 60 min, diluted with 5 mL MeOH, filtered through disc filter, washed with MeOH. Concentrated in vacuo, dissolved in 3 mL DMSO, purified by reverse-phase HPLC (5-70% CH$_3$CN:0.1% TFA/H$_2$O) to give a Ex-60 as a white solid (TFA salt). $^1$H NMR/UPLC consistent with clean P1. $^1$H NMR δ (ppm) (DMSO-d$_6$): 1.80 (3H, s), 2.69 (3H, s), 2.99 (1H, br s), 3.01 (2H, s), 3.17 (2H, s), 4.20 (1H, d, J=15.66 Hz), 4.46 (1H, d, J=15.70 Hz), 6.13-6.10 (1H, m), 6.66 (1H, dd, J=7.98, 2.35 Hz), 6.90 (1H, d, J=8.00 Hz), 7.14 (3H, m), 7.24 (2H, t, J=7.68 Hz), 7.57 (1H, s), 7.79 (1H, q, J=8.16 Hz), 8.37 (1H, s), 8.60 (1H, s), 11.49 (1H, s); HRMS [M+H] C$_{24}$H$_{25}$FN$_5$O$_2$S calc'd 466.1708. found 466.1699.

Using the procedures illustrated in Scheme D, but substituting appropriate reagents, compounds of the following formula were prepared, where Ar$_1$ and R$^L$ are defined in Table VIII:

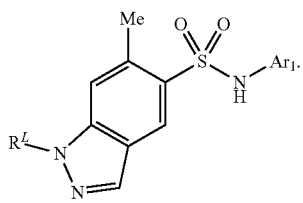

The necessary reagents are either available as articles of commerce or are readily synthesized using literature procedures from starting materials which are articles of commerce.

TABLE VIII

| Example | Structure | Chemical Name | HRMS |
|---|---|---|---|
| Ex-61 | 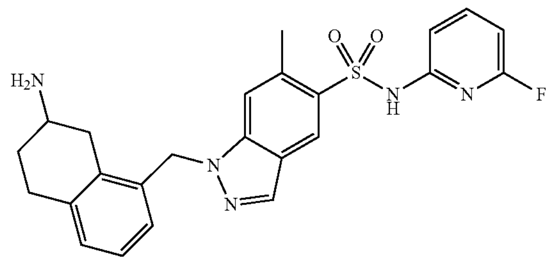 [SMILES: Cc1cc2c(cnn2Cc2cccc3c2CC(N)CC3)cc1S(=O)(=O)Nc1cccc(F)n1] | 1-[(7-amino-5,6,7,8-tetrahydronaphthalen-1-yl)methyl]-N-(6-fluoropyridin-2-yl)-6-methyl-1H-indazole-5-sulfonamide | Calc'd 466.171, found 466.170 |
| Ex-62 | 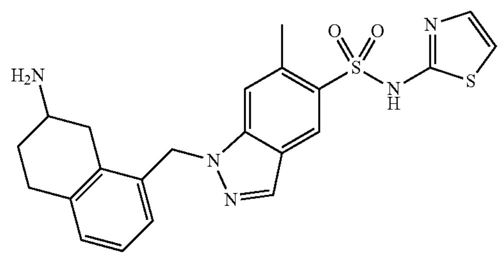 [SMILES: Cc1cc2c(cnn2Cc2cccc3c2CC(N)CC3)cc1S(=O)(=O)Nc1nccs1] | 1-[(7-amino-5,6,7,8-tetrahydronaphthalen-1-yl)methyl]-6-methyl-N-1,3-thiazol-2-yl-1H-indazole-5-sulfonamide | Calc'd 454.1368, found 454.1350 |

Using the procedures illustrated in Examples 1 and 2, but substituting appropriate reagents, compound Ex-63 was prepared:

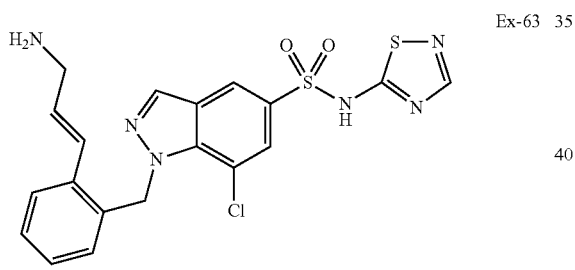

Ex-63

The identity of the compound Ex-63, (1-{2-[(1E)-3-aminoprop-1-en-1-yl]benzyl}-7-chloro-N-1,2,4-thiadiazol-5-yl-1H-indazole-5-sulfonamide), was confirmed by HRMS as described herein [$C_{19}H_{17}ClN_6O_2S_2$ [M+H] calc 461.0619. obs 461.0612].

Potency of the example compounds was assayed using Patch Express or Ion Works techniques, as reported herein. The results are reported below following each example number as follows: Ex-(no.) $Na_v$ 1.7 potency (nM) [ratio 1.5:1.7=$Na_v$ 1.5 potency (nM)/$Na_v$1.7 potency (nM)].

Selected compounds of the invention were assayed for activity for the $Na_v$ 1.7 channel and the $Na_v$ 1.5 channel using the above-described IonWorks technique, and the following results are reported.

Ex-1 $Na_v$ 1.7=106 [Ratio 1.5:1.7=311]; Ex-2 $Na_v$ 1.7=25 [Ratio 1.5:1.7=1200]; Ex-3 $Na_v$ 1.7=328 [Ratio 1.5:1.7=91]; Ex-4 $Na_v$ 1.7=519 [Ratio 1.5:1.7=58]; Ex-5 $Na_v$ 1.7=34 [Ratio 1.5:1.7=963]; Ex-6 $Na_v$ 1.7=21 [Ratio 1.5:1.7=1066]; Ex-7 $Na_v$ 1.7=340 [Ratio 1.5:1.7=19]; Ex-8 $Na_v$ 1.7=856 [Ratio 1.5:1.7=39]; Ex-9 $Na_v$ 1.7=1039 [Ratio 1.5:1.7=27]; Ex-10 $Na_v$ 1.7=1085 [Ratio 1.5:1.7=30]; Ex-11 $Na_v$ 1.7=1477 [Ratio 1.5:1.7=11]; Ex-64 $Na_v$ 1.7=777 [Ratio 1.5:1.7=42]; Ex-12 $Na_v$ 1.7=936 [Ratio 1.5:1.7=15]; Ex-13 $Na_v$ 1.7=6 [Ratio 1.5:1.7=5406]; Ex-14 $Na_v$ 1.7=24 [Ratio 1.5:1.7=1394]; Ex-15 $Na_v$ 1.7=159 [Ratio 1.5:1.7=207]; Ex-16 $Na_v$ 1.7=413 [Ratio 1.5:1.7=81]; Ex-17 $Na_v$ 1.7=559 [Ratio 1.5:1.7=59]; Ex-18 $Na_v$ 1.7=781 [Ratio 1.5:1.7=42]; Ex-19 $Na_v$ 1.7=856 [Ratio 1.5:1.7=39]; Ex-20 $Na_v$ 1.7=960 [Ratio 1.5:1.7=34]; Ex-21 $Na_v$ 1.7=1255 [Ratio 1.5:1.7=26]; Ex-22 $Na_v$ 1.7=1457 [Ratio 1.5:1.7=23]; Ex-23 $Na_v$ 1.7=1705 [Ratio 1.5:1.7=19]; Ex-25 $Na_v$ 1.7=1480 [Ratio 1.5:1.7=23]; Ex-63 $Na_v$ 1.7=1723 [Ratio 1.5:1.7=>19].

Selected compounds of the invention were assayed for activity for the $Na_v$ 1.7 receptor and the $Na_v$ 1.5 receptor using the above-described PatchXpress technique, and the following results are reported.

Ex-1 $Na_v$ 1.7=153 [Ratio 1.5:1.7=310]; Ex-2 $Na_v$ 1.7=20 [Ratio 1.5:1.7=2025]; Ex-3 $Na_v$ 1.7=52 [Ratio 1.5:1.7=636]; Ex-4 $Na_v$ 1.7=855 [Ratio 1.5:1.7=64]; Ex-5 $Na_v$ 1.7=54 [Ratio 1.5:1.7=560]; Ex-6 $Na_v$ 1.7=94 [Ratio 1.5:1.7=320]; Ex-8 $Na_v$ 1.7=1125 [Ratio 1.5:1.7=27]; Ex-9 $Na_v$ 1.7=410 [Ratio 1.5:1.7=65]; Ex-10 $Na_v$ 1.7=782 [Ratio 1.5:1.7=38]; Ex-11 $Na_v$ 1.7=343 [Ratio 1.5:1.7=32]; Ex-64 $Na_v$ 1.7=833 [Ratio 1.5:1.7=36]; Ex-12 $Na_v$ 1.7=495 [Ratio 1.5:1.7=174]; Ex-13 $Na_v$ 1.7=7 [Ratio 1.5:1.7=2275]; Ex-14 $Na_v$ 1.7=21 [Ratio 1.5:1.7=1480]; Ex-15 $Na_v$ 1.7=127 [Ratio 1.5:1.7=237]; Ex-16 $Na_v$ 1.7=939 [Ratio 1.5:1.7=32]; Ex-17 $Na_v$ 1.7=4474 [Ratio 1.5:1.7=7]; Ex-18 $Na_v$ 1.7=5210 [Ratio 1.5:1.7=6]; Ex-19 $Na_v$ 1.7=3026 [Ratio 1.5:1.7=6]; Ex-22 $Na_v$ 1.7=2905 [Ratio 1.5:1.7=>10]; Ex-23 $Na_v$ 1.7=4474 [Ratio 1.5:1.7=>7]; Ex-25 $Na_v$ 1.7=2905 [Ratio 1.5:1.7=10]; Ex-26 $Na_v$ 1.7=5 [Ratio 1.5:1.7=3231]; Ex-27 $Na_v$ 1.7=5 [Ratio 1.5:1.7=48]; Ex-28 $Na_v$ 1.7=25 [Ratio 1.5:1.7=870]; Ex-29 $Na_v$ 1.7=89 [Ratio 1.5:1.7=302]; Ex-30 $Na_v$ 1.7=82 [Ratio 1.5:1.7=326]; Ex-31 $Na_v$ 1.7=56 [Ratio 1.5:1.7=772]; Ex-32 $Na_v$ 1.7=64 [Ratio 1.5:1.7=50]; Ex-33 $Na_v$ 1.7=381 [Ratio 1.5:1.7=228]; Ex-34 $Na_v$ 1.7=77 [Ratio 1.5:1.7=345]; Ex-35 $Na_v$ 1.7=568 [Ratio 1.5:1.7=53];

Ex-37 Na$_v$ 1.7=372 [Ratio 1.5:1.7=64]; Ex-38 Na$_v$ 1.7=185 [Ratio 1.5:1.7=162]; Ex-39 Na$_v$ 1.7=232 [Ratio 1.5:1.7=129]; Ex-40 Na$_v$ 1.7=775 [Ratio 1.5:1.7=11]; Ex-41 Na$_v$ 1.7=1068 [Ratio 1.5:1.7=7]; Ex-42 Na$_v$ 1.7=825 [Ratio 1.5:1.7=36]; Ex-43 Na$_v$ 1.7=584 [Ratio 1.5:1.7=16]; Ex-44 Na$_v$ 1.7=2526 [Ratio 1.5:1.7=10]; Ex-45 Na$_v$ 1.7=2037 [Ratio 1.5:1.7=18]; Ex-46 Na$_v$ 1.7=423 [Ratio 1.5:1.7=41]; Ex-47 Na$_v$ 1.7=546 [Ratio 1.5:1.7=15]; Ex-48 Na$_v$ 1.7=1120 [Ratio 1.5:1.7=5]; Ex-49 Na$_v$ 1.7=661 [Ratio 1.5:1.7=45]; Ex-50 Na$_v$ 1.7=689 [Ratio 1.5:1.7=17]; Ex-53 Na$_v$ 1.7=8 [Ratio 1.5:1.7=1193]; Ex-54 Na$_v$ 1.7=137 [Ratio 1.5:1.7=50]; Ex-55 Na$_v$ 1.7=111 [Ratio 1.5:1.7=152]; Ex-56 Na$_v$ 1.7=244 [Ratio 1.5:1.7=39]; Ex-60 Na$_v$ 1.7=58 [Ratio 1.5:1.7=457]; Ex-61 Na$_v$ 1.7=61 [Ratio 1.5:1.7=171]; Ex-62 Na$_v$ 1.7=23 [Ratio 1.5:1.7=762].

The Compounds of Table IX were prepared using the procedures of Schemes I and II above as comparative examples:

The differences in selectivity and activity of the comparative examples and the compounds of the invention demonstrate the surprising activity and selectivity imparted to the inventive compounds by the combination of the aryl substituents of the "left-side" of the indazole "core" and the selected heteroaryl-1 moiety on the "right-side" of the indazole "core" of the inventive compounds.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound, or a pharmaceutically acceptable salt thereof, having the structure of Formula A$^A$ or Formula A$^B$:

TABLE IX

| Comp Ex | Structure | Chemical Name | Activity |
|---|---|---|---|
| CE-01 | 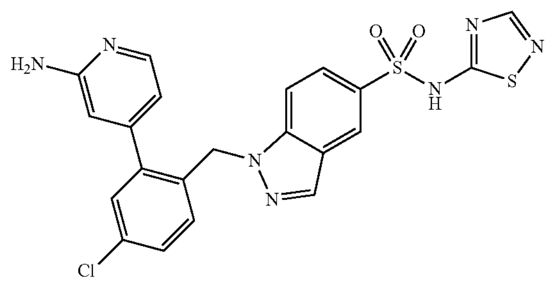 [SMILES: Nc1cc(-c2cc(Cl)ccc2Cn2ncc3cc(S(=O)(=O)Nc4ncns4)ccc32)ccn1] | 1-(2-(2-aminopyridin-4-yl)-4-chlorobenzyl)-N-(1,2,4-thiadiazol-5-yl)-1H-indazole-5-sulfonamide | CE-01 Na$_v$ 1.7 = 26,990 [Ratio 1.5:1.7 = 1] |
| CE-02 | 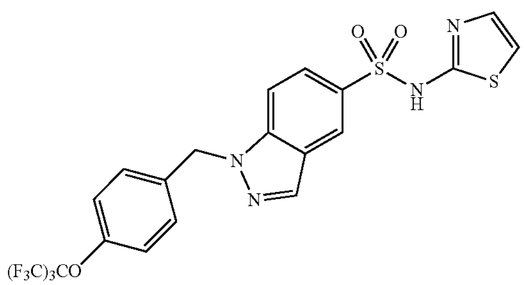 | 1-(4-(1,1,1,3,3,3-hexafluoro-2-(trifluoromethyl)propan-2-yloxy)benzyl)-N-(thiazol-2-yl)-1H-indazole-5-sulfonamide | CE-02 Na$_v$ 1.7 = 33,000 [Ratio 1.5:1.7 = 1] |
| CE-03 | 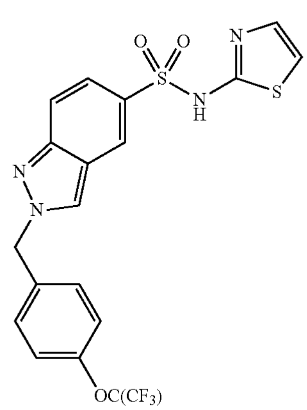 | 2-(4-(1,1,1,3,3,3-hexafluoro-2-(trifluoromethyl)propan-2-yloxy)benzyl)-N-(thiazol-2-yl)-2H-indazole-5-sulfonamide | CE-03 Na$_v$ 1.7 = 33,000 [Ratio 1.5:1.7 = 1] |

Formula A$^A$

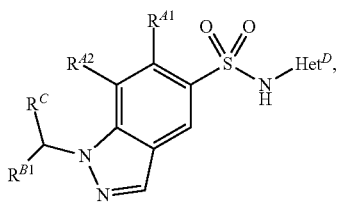

Formula A$^B$

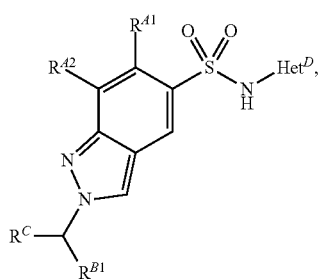

wherein:

"Het$^D$" is a heteroaryl moiety comprising from 5 to 7-ring atoms and from 1 to 3 heteroatoms which are independently for each occurrence sulfur or nitrogen, and which may be optionally substituted with alkyl, aryl, heteroaryl, aralkyl, alkylaryl, aralkenyl, heteroaralkyl, alkylheteroaryl, heteroaralkenyl, hydroxyl, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $R^{60}R^{65}N-$, $R^{60}R^{65}N$-alkyl-, $R^{60}R^{65}NC(O)-$ and $R^{60}R^{65}NSO_2-$, wherein $R^{60}$ and $R^{65}$ are each independently: hydrogen, alkyl, aryl, and aralkyl;

one of "$R^{A1}$" or "$R^{A2}$" is —H and the other is, independently: —H; $C_{1-4}$ alkyl; halogen, with the proviso that if Het$^D$ is selected to be unsubstituted thiazole, $R^{A1}$ is $C_{1-4}$-alkyl or halogen;

$R^{B1}$ is —H or $C_{1-6}$ alkyl which is optionally substituted with: $C_{1-20}$ alkyl; halogen; -alkoxy; —OH; —CN; alkylthio-; amino, —NH(linear or branched alkyl), —NH(cycloalkyl), —N(alkyl)$_2$, —(C=O)—OH; —C(O)O-alkyl; —S(alkyl); or —S(O$_2$)-alkyl; or -aryl; cycloalkyl, each of which optional substituent may itself be substituted with: alkyl, aryl, heteroaryl, aralkyl, alkylaryl, aralkenyl, heteroaralkyl, alkylheteroaryl, heteroaralkenyl, hydroxy (also termed "hydroxyl" when standing alone as a substituent moiety), hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $R^{60}R^{65}N-$, $R^{60}R^{65}N$-alkyl-, $R^{60}R^{65}NC(O)-$ and $R^{60}R^{65}NSO_2-$, wherein $R^{60}$ and $R^{65}$ are each independently: hydrogen, alkyl, aryl, and aralkyl; and $R^C$ is:

(A) a substituent of the formula:

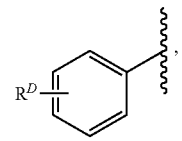

wherein $R^D$ is optionally 1 to 3 substituents which are independently:

(i) I or Cl;

(ii) amino-alkenyl moiety of the formula [H$_2$N—(CH$_2$)$_n$—CH=CH—], where "n" is an integer of 1 to 4;

(iii) heterocycloalkyl of the formula:

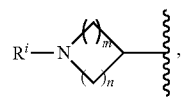

wherein: "n" and "m" are independently 1 to 4; and "$R^b$" is $C_{1-4}$-alkyl or —H;

(iv) a moiety of the formula:

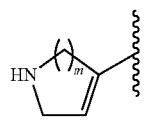

wherein "m" is 1-4;

(v) an aryl moiety which is substituted with a dialkylamino-$C_{1-3}$-alkyl-NH—C(O)— moiety;

(vi) a heterobicyclo-moiety of the formula:

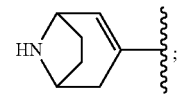

(vii) a substituent of the formula:

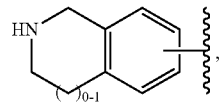

which is optionally substituted with one or more moieties which are, independently: halogen or $C_{1-4}$-alkyl;

(viii) $C_{1-6}$-alkyl moiety, which is optionally substituted with $C_{1-20}$ alkyl; halogen; -alkoxy; —OH; —CN; alkylthio-; amino, —NH(linear or branched alkyl), —NH(cycloalkyl), —N(alkyl)$_2$, —(C=O)—OH; —C(O)O-alkyl; —S(alkyl); or —S(O$_2$)-alkyl; or -aryl; cycloalkyl, each of which optional substituent may itself be substituted with: alkyl, aryl, heteroaryl, aralkyl, alkylaryl, aralkenyl, heteroaralkyl, alkylheteroaryl, heteroaralkenyl, hydroxy (also termed "hydroxyl" when standing alone as a substituent moiety), hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $R^{60}R^{65}N-$, $R^{60}R^{65}N$-alkyl-, $R^{60}R^{65}NC(O)-$ and $R^{60}R^{65}NSO_2-$, wherein $R^{60}$ and $R^{65}$ are each independently: hydrogen, alkyl, aryl;

(ix) $C_{1-6}$-alkoxy which is optionally substituted with $C_{1-20}$ alkyl; halogen; -alkoxy; —OH; —CN; alkylthio-; amino, —NH(linear or branched alkyl), —NH(cycloalkyl), —N(alkyl)$_2$, —(C=O)—OH; —C(O)O-alkyl; —S(alkyl); or —S(O$_2$)-alkyl; or -aryl; cycloalkyl, each of which optional substituent may itself be substituted with: alkyl, aryl, heteroaryl, aralkyl, alkylaryl, aralkenyl, heteroaralkyl, alkylheteroaryl, heteroaralkenyl, hydroxy (also termed "hydroxyl" when standing alone as a substituent moiety), hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $R^{60}R^{65}N-$, $R^{60}R^{65}N$-alkyl-, $R^{60}R^{65}NC(O)-$ and $R^{60}R^{65}NSO_2-$, wherein $R^{60}$ and $R^{65}$ are each independently: hydrogen, alkyl, aryl, and aralkyl;

(x) —CN; or (xi) an alkynyl moiety of up to four carbon atoms which is optionally substituted with $C_{1-20}$ alkyl; halogen; -alkoxy; —OH; —CN; alkylthio-; amino, —NH(linear or branched alkyl), —NH(cycloalkyl), —N(alkyl)$_2$, —(C=O)—OH; —C(O)O-alkyl; —S(alkyl); or —S(O$_2$)-alkyl; or -aryl; cycloalkyl, each of which optional substituent may itself be substituted with: alkyl, aryl, heteroaryl, aralkyl, alkylaryl, aralkenyl, heteroaralkyl, alkylheteroaryl, heteroaryl, heteroaralkenyl, hydroxy (also termed "hydroxyl" when standing alone as a substituent moiety), hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $R^{60}R^{65}N-$, $R^{60}R^{65}N$-alkyl-, $R^{60}R^{65}NC(O)-$ and $R^{60}R^{65}NSO_2-$, wherein $R^{60}$ and $R^{65}$ are each independently: hydrogen, alkyl, aryl, and aralkyl;

(B) a substituent of the formula:

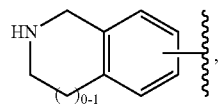

which is optionally substituted with one or more moieties which are, independently: halogen or $C_{1-4}$-alkyl; or (C) a substituent of the formula:

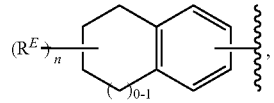

wherein n is an integer of from 0 to 3 and $R^E$ is: (i) —N(R$^i$)$_2$, where R$^i$ is independently —H or —C$_{1-6}$-alkyl, optionally substituted with —CN, OH, or -alkoxy.

2. A compound, or a pharmaceutically acceptable salt thereof, having the structure of Formula A$^A$ or Formula A$^B$:

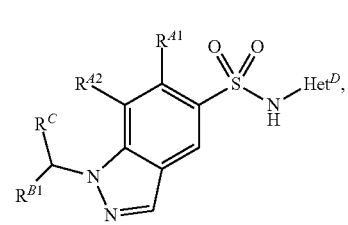

Formula A$^A$

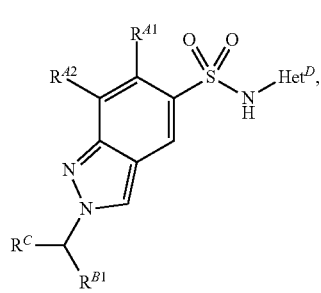

Formula A$^B$ wherein:

Het$^D$ is a heteroaryl moiety comprising from 5 to 7-ring atoms and from 1 to 3 heteroatoms which are independently for each occurrence sulfur or nitrogen and which is optionally substituted, independently for each occurrence, with —Cl or —F;

one of R$^{A1}$ and R$^{A2}$ is —H and the other is —CH$_3$, —F or —Cl;

R$^{B1}$ is —H or C$_{1-6}$ alkyl which is optionally substituted with: C$_{1-20}$ alkyl; halogen; -alkoxy; —OH; —CN; alkylthio-; amino, —NH(linear or branched alkyl), —NH(cycloalkyl), —N(alkyl)$_2$, —(C=O)—OH; —C(O)O-alkyl; —S(alkyl); or —S(O$_2$)-alkyl; or -aryl; cycloalkyl, each of which optional substituent may itself be substituted with: alkyl, aryl, heteroaryl, aralkyl, alkylaryl, aralkenyl, heteroaralkyl, alkylheteroaryl, heteroaralkenyl, hydroxy (also termed "hydroxyl" when standing alone as a substituent moiety), hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $R^{60}R^{65}N-$, $R^{60}R^{65}N$-alkyl-, $R^{60}R^{65}NC(O)-$ and $R^{60}R^{65}NSO_2$—, wherein $R^{60}$ and $R^{65}$ are each independently: hydrogen, alkyl, aryl, and aralkyl; and
$R^C$ is a substituent of the formula:

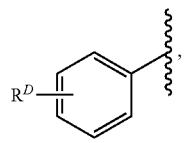

wherein $R^D$ is optionally 1 to 3 substituents which are independently:
(i) —I, —F, or —Cl;
(ii) amino-alkenyl moiety of the formula [$H_2N$—$(CH_2)_n$—CH=CH—], where "n" is an integer of 1 to 4;
(iii) heterocycloalkyl of the formula:

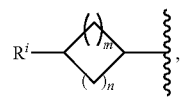

wherein: n and m are independently 1 to 4; and $R^i$ is $C_{1-4}$-alkyl or —H;
(iv) a moiety of the formula:

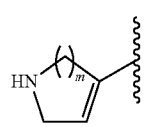

wherein m is 1-4;
(v) aryl moiety which is substituted with a dialkylamino-$C_{1-3}$-alkyl-NH—C(O)— moiety;
(vi) heterobicyclo-moiety of the formula:

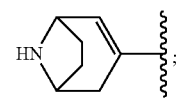

(vii) a moiety of the formula:

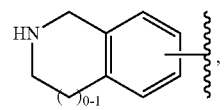

which is optionally substituted independently with one or more moieties that are halogen or $C_{1-4}$-alkyl;
(viii) methyl;
(ix) $C_{1-6}$-alkyl substituted with one or more substituents that are, independently: (a) halogen; or (b) —$N(R^i)_2$, where $R^i$ is independently —H or —$C_{1-6}$-alkyl;
(x) $C_{1-6}$-alkoxy;
(xi) —CN; or
(xii) an alkynyl moiety of up to four carbon atoms substituted by one or more moieties which are independently: (a) $C_{1-6}$-alkyl, optionally substituted with one or more: —$N(R^i)_2$, where $R^i$ is independently —H or —$C_{1-6}$-alkyl; (b) halogen; or (c) —$N(R^i)_2$, where $R^i$ is independently —H or —$C_{1-6}$-alkyl.

3. A compound of claim 1, or a salt thereof, wherein:
Het$^D$ is a heteroaryl moiety comprising from 5 to 7-ring atoms and from 1 to 3 heteroatoms which are independently for each occurrence sulfur or nitrogen and which is optionally substituted, independently for each occurrence, with —Cl or —F;
one of $R^{41}$ and $R^{42}$ is —H and the other is —$CH_3$, —F or —Cl; and
$R^C$ is a substituent of the formula:

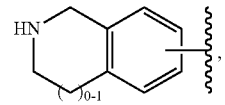

which is optionally substituted independently with one or more halogen or $C_{1-4}$-alkyl.

4. A compound of claim 1, or a salt thereof, wherein:
"Het$^D$" is a heteroaryl moiety comprising from 5 to 7-ring atoms and from 1 to 3 heteroatoms which are independently for each occurrence sulfur or nitrogen and which is optionally substituted, independently for each occurrence, with —Cl or —F;
one of "$R^{41}$" and "$R^{42}$" is —H and the other is —$CH_3$, —F or —Cl; and
$R^C$ is a substituent of the formula:

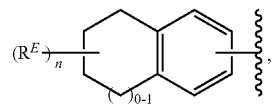

wherein "n" is an integer of from 0 to 3 and $R^E$ is: (i) —$N(R^i)_2$, where "$R^i$" is independently —H or —$C_{1-6}$-alkyl, optionally substituted with —CN, OH, or -alkoxy.

5. A compound of claim 1, or a salt thereof, wherein $R^C$ is a moiety of the Formula:

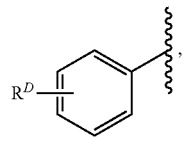

and at least one $R^D$ is —I or —Cl.

6. A compound of claim 1, or a salt thereof, wherein $R^C$ is a moiety of Formula:

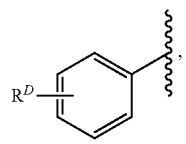

and at least on $R^D$ is N-(2-(dimethylamino)-ethyl)benz-3-yl-carboxamide.

7. A compound of claim 1, or a pharmaceutically acceptable salt thereof, wherein Het$^D$ is a thiazole or a fluoropyridine.

8. A compound of claim 1, or a pharmaceutically acceptable salt thereof, wherein Het$^D$ is:

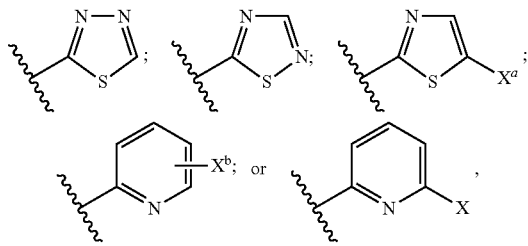

wherein: "X", "X$^a$" and "X$^b$" are independently a halogen.

9. A compound of claim 8, or a pharmaceutically acceptable salt thereof, wherein said halogen is —Cl or —F.

10. A compound or a pharmaceutically acceptable salt thereof, which is:
   6-fluoro-1-((1,2,3,4-tetrahydroisoquinolin-8-yl)methyl)-N-(1,2,4-thiadiazol-5-yl)-1H-indazole-5-sulfonamide;
   6-fluoro-1-((1,2,3,4-tetrahydroisoquinolin-8-yl)methyl)-N-(thiazol-2-yl)-1H-indazole-5-sulfonamide;
   N-(5-chlorothiazol-2-yl)-6-fluoro-1-((1,2,3,4-tetrahydroisoquinolin-8-yl)methyl)-1H-indazole-5-sulfonamide;
   6-fluoro-N-(6-fluoropyridin-2-yl)-1-((1,2,3,4-tetrahydroisoquinolin-8-yl)methyl)-1H-indazole-5-sulfonamide;
   (E)-1-(2-(3-aminoprop-1-en-1-yl)benzyl)-6-fluoro-N-(1,2,4-thiadiazol-5-yl)-1H-indazole-5-sulfonamide;
   (R)-6-fluoro-1-(1-(1,2,3,4-tetrahydroisoquinolin-8-yl)ethyl)-N-(1,2,4-thiadiazol-5-yl)-1H-indazole-5-sulfonamide;
   6-fluoro-1-(1-(1,2,3,4-tetrahydroisoquinolin-8-yl)ethyl)-N-(1,2,4-thiadiazol-5-yl)-1H-indazole-5-sulfonamide;
   6-fluoro-1-(2-iodobenzyl)-N-1,2,4-thiadiazol-5-yl-1H-indazole-5-sulfonamide;
   N-[2-(dimethylamino)ethyl]-2'-{[6-fluoro-5-(1,2,4-thiadiazol-5-ylsulfamoyl)-1H-indazol-1-yl]methyl}biphenyl-3-carboxamide;
   6-fluoro-1-[(1R)-1-phenylethyl]-N-1,2,4-thiadiazol-5-yl-1H-indazole-5-sulfonamide;
   6-fluoro-1-(1-phenylethyl)-N-1,2,4-thiadiazol-5-yl-1H-indazole-5-sulfonamide;
   6-fluoro-1-[2-(1,2,3,4-tetrahydroisoquinolin-5-yl)benzyl]-N-1,2,4-thiadiazol-5-yl-1H-indazole-5-sulfonamide;
   6-fluoro-1-[(1S)-1-phenylethyl]-N-1,2,4-thiadiazol-5-yl-1H-indazole-5-sulfonamide;
   (S)-6-fluoro-1-(1-(1,2,3,4-tetrahydroisoquinolin-8-yl)ethyl)-N-(1,2,4-thiadiazol-5-yl)-1H-indazole-5-sulfonamide;
   1-benzyl-6-fluoro-N-(1,2,4-thiadiazol-5-yl)-1H-indazole-5-sulfonamide;
   1-((7-amino-5,6,7,8-tetrahydronaphthalen-1-yl)methyl)-6-fluoro-N-(1,2,4-thiadiazol-5-yl)-1H-indazole-5-sulfonamide;
   (R)-1-((7-amino-5,6,7,8-tetrahydronaphthalen-1-yl)methyl)-6-fluoro-N-(1,2,4-thiadiazol-5-yl)-1H-indazole-5-sulfonamide;
   (S)-1-((7-amino-5,6,7,8-tetrahydronaphthalen-1-yl)methyl)-6-fluoro-N-(1,2,4-thiadiazol-5-yl)-1H-indazole-5-sulfonamide;
   1-{2-[(1E)-3-aminoprop-1-en-1-yl]benzyl}-N-1,2,4-thiadiazol-5-yl-1H-indazole-5-sulfonamide;
   1-{2-[(1E)-3-aminoprop-1-en-1-yl]-4-chlorobenzyl}-N-1,2,4-thiadiazol-5-yl-1H-indazole-5-sulfonamide;
   1-[4-chloro-2-(2,5,6,7-tetrahydro-1H-azepin-4-yl)benzyl]-N-1,2,4-thiadiazol-5-yl-1H-indazole-5-sulfonamide;
   1-[4-chloro-2-(1,2,3,6-tetrahydropyridin-4-yl)benzyl]-N-1,2,4-thiadiazol-5-yl-1H-indazole-5-sulfonamide;
   1-benzyl-N-1,2,4-thiadiazol-5-yl-1H-indazole-5-sulfonamide;
   5'-chloro-N-[2-(dimethylamino)ethyl]-2'-{[5-(1,2,4-thiadiazol-5-ylsulfamoyl)-1H-indazol-1-yl]methyl}biphenyl-3-carboxamide;
   1-[2-(8-azabicyclo[3.2.1]oct-2-en-3-yl)-4-chlorobenzyl]-N-1,2,4-thiadiazol-5-yl-1H-indazole-5-sulfonamide;
   1-[2-(1,2,3,4-tetrahydroisoquinolin-5-yl)benzyl]-N-1,2,4-thiadiazol-5-yl-1H-indazole-5-sulfonamide;
   1-[2-(2,5,6,7-tetrahydro-1H-azepin-4-yl)benzyl]-N-1,2,4-thiadiazol-5-yl-1H-indazole-5-sulfonamide;
   1-[4-chloro-2-(1,2,3,4-tetrahydroisoquinolin-8-yl)benzyl]-N-1,2,4-thiadiazol-5-yl-1H-indazole-5-sulfonamide;
   1-[4-chloro-2-(1,2,3,4-tetrahydroisoquinolin-5-yl)benzyl]-N-1,2,4-thiadiazol-5-yl-1H-indazole-5-sulfonamide; or
   1-{2-[(1E)-3-aminoprop-1-en-1-yl]benzyl}-7-chloro-N-1,2,4-thiadiazol-5-yl-1H-indazole-5-sulfonamide.

11. A compound or a pharmaceutically acceptable salt thereof, which is:
   6-fluoro-N-(5-fluoropyridin-2-yl)-1-((1,2,3,4-tetrahydroisoquinolin-8-yl)methyl)-1H-indazole-5-sulfonamide;
   1-[(7-amino-5,6,7,8-tetrahydronaphthalen-1-yl)methyl]-6-fluoro-N-1,3-thiazol-2-yl-1H-indazole-5-sulfonamide;
   (R)-1-[(7-amino-5,6,7,8-tetrahydronaphthalen-1-yl)methyl]-6-fluoro-N-1,3-thiazol-2-yl-1H-indazole-5-sulfonamide;
   (S)-1-[(7-amino-5,6,7,8-tetrahydronaphthalen-1-yl)methyl]-6-fluoro-N-1,3-thiazol-2-yl-1H-indazole-5-sulfonamide;
   1-[2-(3-aminopropyl)benzyl]-6-fluoro-N-1,3-thiazol-2-yl-1H-indazole-5-sulfonamide;
   6-fluoro-1-[(1R)-1-(1,2,3,4-tetrahydroisoquinolin-8-yl)ethyl]-N-1,3-thiazol-2-yl-1H-indazole-5-sulfonamide;
   6-fluoro-1-[1-(1,2,3,4-tetrahydroisoquinolin-8-yl)ethyl]-N-1,3-thiazol-2-yl-1H-indazole-5-sulfonamide;
   1-[2-(3-aminoprop-1-yn-1-yl)benzyl]-6-fluoro-N-1,3-thiazol-2-yl-1H-indazole-5-sulfonamide;
   6-fluoro-1-[2-(1,2,3,6-tetrahydropyridin-4-yl)benzyl]-N-1,3-thiazol-2-yl-1H-indazole-5-sulfonamide;
   1-[(7-amino-5,6,7,8-tetrahydronaphthalen-1-yl)methyl]-6-fluoro-N-(6-fluoropyridin-2-yl)-1H-indazole-5-sulfonamide;
   (R)-1-[(7-amino-5,6,7,8-tetrahydronaphthalen-1-yl)methyl]-6-fluoro-N-(6-fluoropyridin-2-yl)-1H-indazole-5-sulfonamide;
   (S)-1-[(7-amino-5,6,7,8-tetrahydronaphthalen-1-yl)methyl]-6-fluoro-N-(6-fluoropyridin-2-yl)-1H-indazole-5-sulfonamide;
   1-[2-(3-aminopropyl)benzyl]-6-fluoro-N-(6-fluoropyridin-2-yl)-1H-indazole-5-sulfonamide;
   1-{(1R)-1-[2-(3-aminopropyl)phenyl]ethyl}-6-fluoro-N-(6-fluoropyridin-2-yl)-1H-indazole-5-sulfonamide;
   1-(1-[2-(3-aminopropyl)phenyl]ethyl)-6-fluoro-N-(6-fluoropyridin-2-yl)-1H-indazole-5-sulfonamide;
   1-[2-(aminomethyl)benzyl]-6-fluoro-N-(6-fluoropyridin-2-yl)-1H-indazole-5-sulfonamide;

1-[2-(2-aminoethyl)benzyl]-6-fluoro-N-(6-fluoropyridin-2-yl)-1H-indazole-5-sulfonamide;
6-fluoro-N-(6-fluoropyridin-2-yl)-1-(1-(1,2,3,4-tetrahydroisoquinolin-8-yl)ethyl)-1H-indazole-5-sulfonamide;
6-fluoro-N-(6-fluoropyridin-2-yl)-1-[(1R)-1-(1,2,3,4-tetrahydroisoquinolin-8-yl)ethyl]-1H-indazole-5-sulfonamide;
1-[2-(2-amino-1-fluoroethyl)benzyl]-6-fluoro-N-(6-fluoropyridin-2-yl)-1H-indazole-5-sulfonamide;
1-[(2-amino-2,3-dihydro-1H-inden-4-yl)methyl]-6-fluoro-N-(6-fluoropyridin-2-yl)-1H-indazole-5-sulfonamide;
1-[(1R)-1-(2-azetidin-3-ylphenyl)ethyl]-6-fluoro-N-(6-fluoropyridin-2-yl)-1H-indazole-5-sulfonamide;
1-[1-(2-azetidin-3-ylphenyl)ethyl]-6-fluoro-N-(6-fluoropyridin-2-yl)-1H-indazole-5-sulfonamide;
6-fluoro-N-(6-fluoropyridin-2-yl)-1-(2-iodobenzyl)-1H-indazole-5-sulfonamide;
1-(2,3-dihydro-1H-isoindol-4-ylmethyl)-6-fluoro-N-(6-fluoropyridin-2-yl)-1H-indazole-5-sulfonamide;
6-fluoro-N-(6-fluoropyridin-2-yl)-1-[(1R)-1-(2-piperidin-4-ylphenyl)ethyl]-1H-indazole-5-sulfonamide;
6-fluoro-N-(6-fluoropyridin-2-yl)-1-(1-(2-piperidin-4-ylphenyl)ethyl)-1H-indazole-5-sulfonamide;
1-[2-(3-aminoprop-1-yn-1-yl)benzyl]-6-fluoro-N-(6-fluoropyridin-2-yl)-1H-indazole-5-sulfonamide;
1-[2-(4-amino-4-methylpent-1-yn-1-yl)benzyl]-6-fluoro-N-(6-fluoropyridin-2-yl)-1H-indazole-5-sulfonamide;
1-{(1R)-1-[2-(3-aminoprop-1-yn-1-yl)phenyl]ethyl}-6-fluoro-N-(6-fluoropyridin-2-yl)-1H-indazole-5-sulfonamide;
1-(1-[2-(3-aminoprop-1-yn-1-yl)phenyl]ethyl)-6-fluoro-N-(6-fluoropyridin-2-yl)-1H-indazole-5-sulfonamide;
1-[(1R)-1-(2-{[(1S,2S)-2-aminocyclohexyl]ethynyl}phenyl)ethyl]-6-fluoro-N-(6-fluoropyridin-2-yl)-1H-indazole-5-sulfonamide;
1-[(1R)-1-(2-{[(1R,2R)-2-aminocyclohexyl]ethynyl}phenyl)ethyl]-6-fluoro-N-(6-fluoropyridin-2-yl)-1H-indazole-5-sulfonamide;
1-[1-(2-{(2-aminocyclohexyl)ethynyl}phenyl)ethyl]-6-fluoro-N-(6-fluoropyridin-2-yl)-1H-indazole-5-sulfonamide;
6-fluoro-N-(6-fluoropyridin-2-yl)-1-{(1R)-1-[2-(1,2,3,6-tetrahydropyridin-4-yl)phenyl]ethyl}-1H-indazole-5-sulfonamide;
6-fluoro-N-(6-fluoropyridin-2-yl)-1-(1-[2-(1,2,3,6-tetrahydropyridin-4-yl)phenyl]ethyl)-1H-indazole-5-sulfonamide;
6-fluoro-N-(6-fluoropyridin-2-yl)-1-[(4-fluoro-1,2,3,4-tetrahydroisoquinolin-8-yl)methyl]-1H-indazole-5-sulfonamide;
1-[(1R)-1-(2-{[(1R,2R)-2-aminocyclohexyl]ethynyl}phenyl)ethyl]-6-fluoro-N-(6-fluoropyridin-2-yl)-1H-indazole-5-sulfonamide;
1-[(1R)-1-(2-{[(1S,2S)-2-aminocyclohexyl]ethynyl}phenyl)ethyl]-6-fluoro-N-(6-fluoropyridin-2-yl)-1H-indazole-5-sulfonamide;
1-(1-(2-([2-aminocyclohexyl]ethynyl)phenyl)ethyl)-6-fluoro-N-(6-fluoropyridin-2-yl)-1H-indazole-5-sulfonamide;
1-benzyl-6-fluoro-N-(6-fluoropyridin-2-yl)-1H-indazole-5-sulfonamide;
6-fluoro-N-(6-fluoropyridin-2-yl)-1-[2-(1,2,3,6-tetrahydropyridin-4-yl)benzyl]-1H-indazole-5-sulfonamide;
1-[(7-amino-5,6,7,8-tetrahydronaphthalen-1-yl)methyl]-N-(5-chloro-1,3-thiazol-2-yl)-6-fluoro-1H-indazole-5-sulfonamide;
N-(5-chloro-1,3-thiazol-2-yl)-6-fluoro-1-[(1R)-1-(1,2,3,4-tetrahydroisoquinolin-8-yl)ethyl]-1H-indazole-5-sulfonamide;
N-(5-chloro-1,3-thiazol-2-yl)-6-fluoro-1-[1-(1,2,3,4-tetrahydroisoquinolin-8-yl)ethyl]-1H-indazole-5-sulfonamide;
N-(5-chloro-1,3-thiazol-2-yl)-6-fluoro-2-[(1R)-1-(1,2,3,4-tetrahydroisoquinolin-8-yl)ethyl]-2H-indazole-5-sulfonamide;
N-(5-chloro-1,3-thiazol-2-yl)-6-fluoro-2-[1-(1,2,3,4-tetrahydroisoquinolin-8-yl)ethyl]-2H-indazole-5-sulfonamide;
1-{(1R)-1-[2-(3-aminoprop-1-yn-1-yl)phenyl]ethyl}-N-(5-chloro-1,3-thiazol-2-yl)-6-fluoro-1H-indazole-5-sulfonamide;
1-(1-[2-(3-aminoprop-1-yn-1-yl)phenyl]ethyl)-N-(5-chloro-1,3-thiazol-2-yl)-6-fluoro-1H-indazole-5-sulfonamide;
2-[(7-amino-5,6,7,8-tetrahydronaphthalen-1-yl)methyl]-N-(5-chloro-1,3-thiazol-2-yl)-6-fluoro-2H-indazole-5-sulfonamide;
6-fluoro-N-(5-fluoropyridin-2-yl)-1-[(1R)-1-(1,2,3,4-tetrahydroisoquinolin-8-yl)ethyl]-1H-indazole-5-sulfonamide;
6-fluoro-N-(5-fluoropyridin-2-yl)-1-(1-(1,2,3,4-tetrahydroisoquinolin-8-yl)ethyl)-1H-indazole-5-sulfonamide;
1-{(1R)-1-[2-(3-aminoprop-1-yn-1-yl)phenyl]ethyl}-6-fluoro-N-(5-fluoropyridin-2-yl)-1H-indazole-5-sulfonamide;
1-(1-[2-(3-aminoprop-1-yn-1-yl)phenyl]ethyl)-6-fluoro-N-(5-fluoropyridin-2-yl)-1H-indazole-5-sulfonamide;
(R)—N-(6-fluoropyridin-2-yl)-6-methyl-1-(1-(1,2,3,4-tetrahydroisoquinolin-8-yl)ethyl)-1H-indazole-5-sulfonamide;
N-(6-fluoropyridin-2-yl)-6-methyl-1-(1-(1,2,3,4-tetrahydroisoquinolin-8-yl)ethyl)-1H-indazole-5-sulfonamide;
1-[(7-amino-5,6,7,8-tetrahydronaphthalen-1-yl)methyl]-N-(6-fluoropyridin-2-yl)-6-methyl-1H-indazole-5-sulfonamide; or
1-[(7-amino-5,6,7,8-tetrahydronaphthalen-1-yl)methyl]-6-methyl-N-1,3-thiazol-2-yl-1H-indazole-5-sulfonamide.

12. A compound or a pharmaceutically acceptable salt thereof, which is:
(R)-6-fluoro-1-(1-(1,2,3,4-tetrahydroisoquinolin-8-yl)ethyl)-N-(1,2,4-thiadiazol-5-yl)-1H-indazole-5-sulfonamide;
6-fluoro-1-[(1R)-1-phenylethyl]-N-1,2,4-thiadiazol-5-yl-1H-indazole-5-sulfonamide;
(R)-1-((7-amino-5,6,7,8-tetrahydronaphthalen-1-yl)methyl)-6-fluoro-N-(1,2,4-thiadiazol-5-yl)-1H-indazole-5-sulfonamide;
6-fluoro-1-[(1R)-1-(1,2,3,4-tetrahydroisoquinolin-8-yl)ethyl]-N-1,3-thiazol-2-yl-1H-indazole-5-sulfonamide;
1-{(1R)-1-[2-(3-aminopropyl)phenyl]ethyl}-6-fluoro-N-(6-fluoropyridin-2-yl)-1H-indazole-5-sulfonamide;
6-fluoro-N-(6-fluoropyridin-2-yl)-1-[(1R)-1-(1,2,3,4-tetrahydroisoquinolin-8-yl)ethyl]-1H-indazole-5-sulfonamide;
1-[(1R)-1-(2-azetidin-3-ylphenyl)ethyl]-6-fluoro-N-(6-fluoropyridin-2-yl)-1H-indazole-5-sulfonamide;

6-fluoro-N-(6-fluoropyridin-2-yl)-1-[(1R)-1-(2-piperidin-4-ylphenyl)ethyl]-1H-indazole-5-sulfonamide;

1-{(1R)-1-[2-(3-aminoprop-1-yn-1-yl)phenyl]ethyl}-6-fluoro-N-(6-fluoropyridin-2-yl)-1H-indazole-5-sulfonamide;

1-[(1R)-1-(2-{[(1S,2S)-2-aminocyclohexyl]ethynyl}phenyl)ethyl]-6-fluoro-N-(6-fluoropyridin-2-yl)-1H-indazole-5-sulfonamide;

6-fluoro-N-(6-fluoropyridin-2-yl)-1-{(1R)-1-[2-(1,2,3,6-tetrahydropyridin-4-yl)phenyl]ethyl}-1H-indazole-5-sulfonamide;

1-[(1R)-1-(2-{[(1R,2R)-2-aminocyclohexyl]ethynyl}phenyl)ethyl]-6-fluoro-N-(6-fluoropyridin-2-yl)-1H-indazole-5-sulfonamide;

N-(5-chloro-1,3-thiazol-2-yl)-6-fluoro-1-[(1R)-1-(1,2,3,4-tetrahydroisoquinolin-8-yl)ethyl]-1H-indazole-5-sulfonamide;

N-(5-chloro-1,3-thiazol-2-yl)-6-fluoro-2-[(1R)-1-(1,2,3,4-tetrahydroisoquinolin-8-yl)ethyl]-2H-indazole-5-sulfonamide;

1-{(1R)-1-[2-(3-aminoprop-1-yn-1-yl)phenyl]ethyl}-N-(5-chloro-1,3-thiazol-2-yl)-6-fluoro-1H-indazole-5-sulfonamide;

6-fluoro-N-(5-fluoropyridin-2-yl)-1-[(1R)-1-(1,2,3,4-tetrahydroisoquinolin-8-yl)ethyl]-1H-indazole-5-sulfonamide;

1-{(1R)-1-[2-(3-aminoprop-1-yn-1-yl)phenyl]ethyl}-6-fluoro-N-(5-fluoropyridin-2-yl)-1H-indazole-5-sulfonamide; or (R)—N-(6-fluoropyridin-2-yl)-6-methyl-1-(1-(1,2,3,4-tetrahydroisoquinolin-8-yl)ethyl)-1H-indazole-5-sulfonamide.

13. A pharmaceutical composition comprising at least one compound, or a salt thereof, of claim 1 and at least one pharmaceutically acceptable excipient.

14. A pharmaceutical composition comprising at least one compound of claim 10, or a salt thereof, and at least one pharmaceutically acceptable excipient.

15. A pharmaceutical composition comprising at least one compound of claim 11, or a salt thereof, and at least one pharmaceutically acceptable excipient.

16. A pharmaceutical composition comprising at least one compound of claim 12, or a salt thereof, and at least one pharmaceutically acceptable excipient.

17. A method of treating a neuropathic pain disorder comprising administering to a patient in need thereof a therapeutically effective amount of a pharmaceutical composition of claim 13.

18. A method of treating a neuropathic pain disorder comprising administering to a patient in need thereof a therapeutically effective amount of a pharmaceutical composition of claim 14.

19. A method of treating a neuropathic pain disorder comprising administering to a patient in need thereof a therapeutically effective amount of a pharmaceutical composition of claim 15.

20. A method of treating a neuropathic pain disorder comprising administering to a patient in need thereof a therapeutically effective amount of a pharmaceutical composition of claim 16.

* * * * *